US007897341B2

(12) United States Patent
Griffiths et al.

(10) Patent No.: US 7,897,341 B2
(45) Date of Patent: *Mar. 1, 2011

(54) OPTICAL SORTING METHOD

(75) Inventors: Andrew Griffiths, Cambridge (GB); Dan Tawfik, Cambridge (GB); Armin Sepp, Cambridge (GB)

(73) Assignee: Medical Research Council, London (GB)

( * ) Notice: Subject to any disclaimer, the term of this patent is extended or adjusted under 35 U.S.C. 154(b) by 416 days.

This patent is subject to a terminal disclaimer.

(21) Appl. No.: 11/820,165

(22) Filed: Jun. 18, 2007

(65) Prior Publication Data
US 2009/0053700 A1    Feb. 26, 2009

Related U.S. Application Data

(60) Division of application No. 10/956,242, filed on Oct. 1, 2004, now abandoned, which is a division of application No. 09/896,915, filed on Jun. 29, 2001, now Pat. No. 6,808,882, which is a continuation-in-part of application No. PCT/GB00/00030, filed on Jan. 6, 2000.

(30) Foreign Application Priority Data
Jan. 7, 1999    (GB) ................................. 9900298.2

(51) Int. Cl.
*C12Q 1/68* (2006.01)
*C12P 21/06* (2006.01)
*C12P 19/34* (2006.01)
*C07H 21/02* (2006.01)

(52) U.S. Cl. .............................. 435/6; 435/3; 435/69.1; 435/91.1; 435/91.51; 536/23.1

(58) Field of Classification Search ........................ None
See application file for complete search history.

(56) References Cited

U.S. PATENT DOCUMENTS 4,675,285 A * 6/1987 Clark et al. ..................... 435/6

FOREIGN PATENT DOCUMENTS

| EP | 1522582 A2 | 4/2005 |
|---|---|---|
| WO | WO-93/03151 | 2/1993 |
| WO | WO-98/41869 | 9/1998 |
| WO | WO-99/02671 | 1/1999 |

OTHER PUBLICATIONS

Naoto Nemoto, Etsuko Miyamoto-Sato, Yzuru Husimi, Hiroshi Yanagawa "In vitro virus: Bonding of mRNA bearing puromycin at the 3'-terminal end to the C-terminal end of its encoded protein on the ribosome in vitro", *Federation of European Biochemical Societies* (Aug. 1, 1997) pp. 405-408.

Shane Atwell and James A. Wells "Selection for improved subtiligases by phage display", *Proc. Natl. Acad. Sci. USA* (Feb. 26, 1999) vol. 96 pp. 9497-9502.

Jean-Luc Jestin, Peter Dristensen, and Greg Winter, "A Method for the Selection of Catalytic Activity Using Phage Display and Proximity Coupling" *Angew.Chem.Int.* (1999) vol. 38, No. 8 pp. 1124-1127.

Patrice Soumillion, Laurent Jespers, Michele Bouchet, Jacqueline Marchand-Brynaert, Greg Winter and Jacques Fastrez "Selection of B-Lactamase on Felamentous Bacteriophage by Catalytic Activity" *Accademic Press Limited* (1994) vol. 237, pp. 415-422.

Mikael Wildersten and Bengt Mannervik "Glutathione Transferases with Novel active Sites Isolated by Phage Display from a Library of Random Mutants" *Academic Press Limited*, (1995) vol. 250, pp. 115-122.

Salvator Demartis, Adrian Huber, Francesca Viti, Luisa Lozzi, Leonardo Giovannoni, Paolo Neri, Greg Winter and Dario Neri "A Strategy for the Isolation of Catalytic Actibities from Repertoires of Enzymes Displayed on Phage" *Academic Press Limited* (1999) Article No. jmbi.1998.2476, pp. 617-633.

Steven Bass, Ronald Greene, and James A. Wells "Hormone Phage: An Enrichment Method for Variant Proteins With Altered Bindig Properties", *Wiley-Liss*, (1990), pp. 309-314.

"Filamentous Fusion Phage: Novel Expression vectors That Display cloned Antigens on the Virion Surface" *Science*, vol. 28 (Jun. 14, 1995), pp. 1315-1317.

Kim D. Janda, Lee-Chiang Lo, Chih-Hung L. Lo, Mui-Mui Sim, Ruo Wang, Chi-Huey Wong, and Richard A. Lerner "Chemical Selection for Catalysis in Combinatorial Antibody Libraries" www.sciencemag.org, vol. 275 (Feb. 14, 1997) pp. 945-948.

John McCafferty, Andrew D. Griffiths, Greg Winter, David J. Chiswell "Phage antibodies: gilamentous phage displaying antibody variable domains" *Letters to Nature*, vol. 348 (Dec. 6, 1980) pp. 552-554.

Richard W. Roberts and Jack W. Szostak "RNA-peptide fusions for the in vitro selection of peptides and proteins" *Proc.Natl.Acad.Sci. USA*, vol. 94 (Nov. 1997) pp. 12297-12302.

Millard G. Cull, Jeff F. Miller and Peter J. Schatz "Screening for receptor ligands using large libraries of peptides linked to the C terminus of the lac repressor" *Proc.Natl.Acad.Sci. USA*, vol. 89, (1992) pp. 1865-1869.

(Continued)

*Primary Examiner*—Samuel C Woolwine
(74) *Attorney, Agent, or Firm*—Edwards Angell Palmer & Dodge LLP; Kathleen Williams; Elbert Chiang

(57) ABSTRACT

The invention describes a method for isolating one or more genetic elements encoding a gene product having a desired activity, comprising the steps of: (a) compartmentalising genetic elements into microcapsules; (b) expressing the genetic elements to produce their respective gene products within the microcapsules; (c) sorting the genetic elements which produce the gene product having the desired activity using a change in the optical properties of the genetic elements. The invention enables the in vitro evolution of nucleic acids and proteins by repeated mutagenesis and iterative applications of the method of the invention.

42 Claims, 21 Drawing Sheets

OTHER PUBLICATIONS

Henrik Pedersen, Swen Holder, Daniel P. Sutherlin, Urs Schwitter, David S. King, and Peter G. Schultz "A method for directed evolution and functional cloning of enzymes" *Proc. Natl. Acad. Sci. USA*, vol. 95, (Sep. 1998), pp. 10523-10528.

Tawfik, et al., "Man-Made Cell-Like Compartments for Molecular Evolution", Nature Biotechnology (1998), V. 7, No. 16, pp. 652-656.

Anarbaev, et al., "Klenow Fragment and DNA Polymerase α-Primase Fromserva Calf Thymus in Water-in-Oil Microemulsions", Biochimica et Biophysica Acta (1998), V. 1384, No. 2, pp. 315-324.

Oberholzer, et al., "Polymerase Chain Reaction in Liposomes", Chemistry and Biology (1995), V. 2, No. 10, pp. 677-682.

Oberholzer, et al., "Enzymatic RNA Replication in Self-Reproducing Vesicles: An Approach to a Minimal Cell", Biochemical and Biophysical Research Communications (1995), V. 207, No. 1, pp. 250-257.

Walde, et al., "Oparin's Reactions Revisited: Enzymatic Synthesis of Poly (Adenylic Acid) in Micelles and Self-Reproducing Vesicles", Journal of the American Chemical Society (1994), V. 116, No. 17, pp. 7541-7547.

* cited by examiner

OPTICAL SORTING METHOD

This application is a divisional of U.S. patent application Ser. No. 10/956,242, filed Oct. 1, 2004, which is a divisional of U.S. patent application Ser. No. 09/896,915, filed Jun. 29, 2001, which is a continuation-in-part of International Patent Application No. PCT/GB00/00030, filed Jan. 6, 2000, which designated the U.S. and was published in English and which claimed the priority of Great Britain Patent Application No. GB9900298.2, filed Jan. 7, 1999. The entirety of each of these priority documents is hereby incorporated herein in its entirety.

The present invention relates to methods for use in in vitro evolution of molecular libraries. In particular, the present invention relates to methods of selecting nucleic acids encoding gene products in which the nucleic acid and the activity of the encoded gene product are linked by compartmentation.

Evolution requires the generation of genetic diversity (diversity in nucleic acid) followed by the selection of those nucleic acids which result in beneficial characteristics. Because the nucleic acid and the activity of the encoded gene product of an organism are physically linked (the nucleic acids being confined within the cells which they encode) multiple rounds of mutation and selection can result in the progressive survival of organisms with increasing fitness. Systems for rapid evolution of nucleic acids or proteins in vitro advantageously mimic this process at the molecular level in that the nucleic acid and the activity of the encoded gene product are linked and the activity of the gene product is selectable.

Recent advances in molecular biology have allowed some molecules to be co-selected according to their properties along with the nucleic acids that encode them. The selected nucleic acids can subsequently be cloned for further analysis or use, or subjected to additional rounds of mutation and selection.

Common to these methods is the establishment of large libraries of nucleic acids. Molecules having the desired characteristics (activity) can be isolated through selection regimes that select for the desired activity of the encoded gene product, such as a desired biochemical or biological activity, for example binding activity.

Phage display technology has been highly successful as providing a vehicle that allows for the selection of a displayed protein by providing the essential link between nucleic acid and the activity of the encoded gene product (Smith, 1985; Bass et al., 1990; McCafferty et al., 1990; for review see Clackson and Wells, 1994). Filamentous phage particles act as genetic display packages with proteins on the outside and the genetic elements which encode them on the inside. The tight linkage between nucleic acid and the activity of the encoded gene product is a result of the assembly of the phage within bacteria. As individual bacteria are rarely multiply infected, in most cases all the phage produced from an individual bacterium will carry the same genetic element and display the same protein.

However, phage display relies upon the creation of nucleic acid libraries in vivo in bacteria. Thus, the practical limitation on library size allowed by phage display technology is of the order of $10^7$ to $10^{11}$, even taking advantage of λ phage vectors with excisable filamentous phage replicons. The technique has mainly been applied to selection of molecules with binding activity. A small number of proteins with catalytic activity have also been isolated using this technique, however, selection was not directly for the desired catalytic activity, but either for binding to a transition-state analogue (Widersten and Mannervik, 1995) or reaction with a suicide inhibitor (Soumillion et al., 1994; Janda et al., 1997). More recently there have been some examples of enzymes selected using phage-display by product formation (Atwell & Wells, 1999; Demartis et al., 1999; Jestin et al., 1999; Pederson, et al., 1998), but in all these cases selection was not for multiple turnover.

Specific peptide ligands have been selected for binding to receptors by affinity selection using large libraries of peptides linked to the C terminus of the lac repressor LacI (Cull et al., 1992). When expressed in *E. coli* the repressor protein physically links the ligand to the encoding plasmid by binding to a lac operator sequence on the plasmid.

An entirely in vitro polysome display system has also been reported (Mattheakis et al., 1994; Hanes and Pluckthun, 1997) in which nascent peptides are physically attached via the ribosome to the RNA which encodes them. An alternative, entirely in vitro system for linking genotype to phenotype by making RNA-peptide fusions (Roberts and Szostak, 1997; Nemoto et al., 1997) has also been described.

However, the scope of the above systems is limited to the selection of proteins and furthermore does not allow direct selection for activities other than binding, for example catalytic or regulatory activity.

In vitro RNA selection and evolution (Ellington and Szostak, 1990), sometimes referred to as SELEX (systematic evolution of ligands by exponential enrichment) (Tuerk and Gold, 1990) allows for selection for both binding and chemical activity, but only for nucleic acids. When selection is for binding, a pool of nucleic acids is incubated with immobilised substrate. Non-binders are washed away, then the binders are released, amplified and the whole process is repeated in iterative steps to enrich for better binding sequences. This method can also be adapted to allow isolation of catalytic RNA and DNA (Green and Szostak, 1992; for reviews see Chapman and Szostak, 1994; Joyce, 1994; Gold et al., 1995; Moore, 1995).

However, selection for "catalytic" or binding activity using SELEX is only possible because the same molecule performs the dual role of carrying the genetic information and being the catalyst or binding molecule (aptamer). When selection is for "auto-catalysis" the same molecule must also perform the third role of being a substrate. Since the genetic element must play the role of both the substrate and the catalyst, selection is only possible for single turnover events. Because the "catalyst" is in this process itself modified, it is by definition not a true catalyst. Additionally, proteins may not be selected using the SELEX procedure. The range of catalysts, substrates and reactions which can be selected is therefore severely limited.

Those of the above methods that allow for iterative rounds of mutation and selection are mimicking in vitro mechanisms usually ascribed to the process of evolution: iterative variation, progressive selection for a desired the activity and replication. However, none of the methods so far developed have provided molecules of comparable diversity and functional efficacy to those that are found naturally. Additionally, there are no man-made "evolution" systems which can evolve both nucleic acids and proteins to effect the full range of biochemical and biological activities (for example, binding, catalytic and regulatory activities) and that can combine several processes leading to a desired product or activity.

There is thus a great need for an in vitro system that overcomes the limitations discussed above.

In Tawfik and Griffiths (1998), and in International patent application PCT/GB98/01889, we describe a system for in vitro evolution that overcomes many of the limitations described above by using compartmentalisation in microcapsules to link genotype and phenotype at the molecular level.

In Tawfik and Griffiths (1998), and in several embodiments of International patent application PCT/GB98/01889, the desired activity of a gene product results in a modification of the genetic element which encoded it (and is present in the same microcapsule). The modified genetic element can then be selected in a subsequent step.

Here we describe a further invention in which the modification of the genetic element causes a change in the optical properties of the element itself, and which has many advantages over the methods described previously.

BRIEF DESCRIPTION OF THE INVENTION

According to a first aspect of the present invention, there is provided a method for isolating one or more genetic elements encoding a gene product having a desired activity the expression of which may result, directly or indirectly, in the modification of an optical property of a genetic element encoding the gene product, comprising the steps of:
(a) compartmentalising genetic elements into microcapsules;
(b) expressing the genetic elements to produce their respective gene products within the microcapsules;
(c) sorting the genetic elements which produce the gene product(s) having the desired activity according to the changed optical properties of the genetic elements.

The microcapsules according to the present invention compartmentalise genetic elements and gene products such that they remain physically linked together.

As used herein, a genetic element is a molecule or molecular construct comprising a nucleic acid. The genetic elements of the present invention may comprise any nucleic acid (for example, DNA, RNA or any analogue, natural or artificial, thereof). The nucleic acid component of the genetic element may moreover be linked, covalently or non-covalently, to one or more molecules or strictures, including proteins, chemical entities and groups, and solid-phase supports such as beads (including nonmagnetic, magnetic and paramagnetic beads), and the like. In the method of the invention, these structures or molecules can be designed to assist in the sorting and/or isolation of the genetic element encoding a gene product with the desired activity.

Expression, as used herein, is used in its broadest meaning, to signify that a nucleic acid contained in the genetic element is converted into its gene product. Thus, where the nucleic acid is DNA, expression refers to the transcription of the DNA into RNA; where this RNA codes for protein, expression may also refer to the translation of the RNA into protein. Where the nucleic acid is RNA, expression may refer to the replication of this RNA into further RNA copies, the reverse transcription of the RNA into DNA and optionally the transcription of this DNA into further RNA molecule(s), as well as optionally the translation of any of the RNA species produced into protein. Preferably, therefore, expression is performed by one or more processes selected from the group consisting of transcription, reverse transcription, replication and translation.

Expression of the genetic element may thus be directed into either DNA, RNA or protein, or a nucleic acid or protein containing unnatural bases or amino acids (the gene product) within the microcapsule of the invention, so that the gene product is confined within the same microcapsule as the genetic element.

The genetic element and the gene product thereby encoded are linked by confining each genetic element and the respective gene product encoded by the genetic element within the same microcapsule. In this way the gene product in one microcapsule cannot cause a change in any other microcapsules. In addition, further linking means may be employed to link gene products to the genetic elements encoding them, as set forth below.

The term "microcapsule" is used herein in accordance with the meaning normally assigned thereto in the art and further described hereinbelow. In essence, however, a microcapsule is an artificial compartment whose delimiting borders restrict the exchange of the components of the molecular mechanisms described herein which allow the sorting of the genetic elements according to the function of the gene products which they encode.

Preferably, the microcapsules used in the method of the present invention will be capable of being produced in very large numbers, and thereby to compartmentalise a library of genetic elements which encodes a repertoire of gene products.

As used herein, a change in optical properties of the genetic elements refers to a change greater than 10% in absorption or emission of electromagnetic radiation, including changes in absorbance, luminescence, phosphorescence or fluorescence, relative to the optical property measured before expression of a genetic element. All such properties are included in the term "optical". Genetic elements can be sorted, for example, by luminescence, fluorescence or phosphorescence activated sorting. In a preferred embodiment, flow cytometry is employed to sort genetic elements, for example, light scattering (Kerker, 1983) and fluorescence polarisation (Rolland et al., 1985) can be used to trigger flow sorting. In a highly preferred embodiment genetic elements are sorted using a fluorescence activated cell sorter (FACS) sorter (Norman, 1980; Mackenzie and Pinder, 1986).

Changes in optical properties may be direct or indirect. Thus, the change may result in the alteration of an optical property in the genetic element itself, or may lead indirectly to such a change. For example, modification of a genetic element may alter (i.e., change by at least 10%) its ability to bind an optically active ligand, thus indirectly altering its optical properties.

Alternatively, imaging techniques can be used to screen thin films of genetic elements to allow enrichment for a genetic element with desirable properties, for example by physical isolation of the region where a genetic element with desirable properties is situated, or ablation of non-desired genetic elements. The genetic elements can be detected by luminescence, phosphorescence or fluorescence.

According to a preferred embodiment of the first aspect of the present invention, the sorting of genetic elements may be performed in one of essentially two techniques.

(I) In a first embodiment, the genetic elements are sorted following pooling of the microcapsules into one or more common compartments. In this embodiment, a gene product having the desired activity modifies the genetic element which encoded it (and which resides in the same microcapsule) so as to make it selectable as a result of its modified optical properties in a subsequent step. The reactions are stopped and the microcapsules are then broken so that all the contents of the individual microcapsules are pooled. The modification of the genetic element in the microcapsule may result directly in the modification of the optical properties of the genetic element. Alternatively, the modification may allow the genetic elements to be further modified outside the microcapsules so as to induce a change in their optical properties. Selection for the genetic elements with modified optical properties enables enrichment of the genetic elements encoding the gene product(s) having the desired activity. Accordingly, the invention provides a method according to the first aspect of the invention, wherein in step (b) the gene product having the desired activity modifies the genetic element encoding it to enable the isolation of the genetic element as a result in a change in the optical properties of the genetic element. It is to be understood, of course, that modification may be direct, in that it is caused by the direct action of the gene product on the genetic element, or indirect, in which a series of reactions, one or more of which involve the gene product having the desired activity, leads to modification of the genetic element.

(II) In a second embodiment, the genetic elements may be sorted by a multi-step procedure, which involves at least two steps, for example, in order to allow the exposure of the genetic elements to conditions which permit at least two separate reactions to occur. As will be apparent to persons skilled in the art, the first microencapsulation step of the invention advantageously results in conditions which permit the expression of the genetic elements—be it transcription, transcription and/or translation; replication or the like. Under these conditions, it may not be possible to select for a particular gene product activity, for example because the gene product may not be active under these conditions, or because the expression system contains an interfering activity. The invention therefore provides a method according to the first aspect of the present invention, wherein step (b) comprises expressing the genetic elements to produce their respective gene products within the microcapsules, linking the gene products to the genetic elements encoding them and isolating the complexes thereby formed. This allows for the genetic elements and their associated gene products to be isolated from the capsules before sorting according to gene product activity takes place. In a preferred embodiment, the complexes are subjected to a further compartmentalisation step prior to isolating the genetic elements encoding a gene product having the desired activity. This further compartmentalisation step, which advantageously takes place in microcapsules, permits the performance of further reactions, under different conditions, in an environment where the genetic elements and their respective gene products are physically linked. Eventual sorting of genetic elements may be performed according to embodiment (I) above.

The "secondary encapsulation" may also be performed with genetic elements linked to gene products by other means, such as by phage display, polysome display, RNA-peptide fusion or lac repressor peptide fusion.

The selected genetic element(s) may also be subjected to subsequent, optionally more stringent rounds of sorting in iteratively repeated steps, reapplying the method of the invention either in its entirety or in selected steps only. By tailoring the conditions appropriately, genetic elements encoding gene products having a better optimised activity may be isolated after each round of selection.

Additionally, the genetic elements isolated after a first round of sorting may be subjected to mutagenesis before repeating the sorting by iterative repetition of the steps of the method of the invention as set out above. After each round of mutagenesis, some genetic elements will have been modified in such a way that the activity of the gene products is enhanced (i.e., measurable activity increased by at least 10% relative to wild-type).

Moreover, the selected genetic elements can be cloned into an expression vector to allow further characterisation of the genetic elements and their products.

In a second aspect, the invention provides a product when selected according to the first aspect of the invention. As used in this context, a "product" may refer to a gene product, selectable according to the invention, or the genetic element (or genetic information comprised therein).

In a third aspect, the invention provides a method for preparing a gene product, the expression of which may result, directly or indirectly, in the modification the optical properties of a genetic element encoding it, comprising the steps of:
(a) preparing a genetic element encoding the gene product;
(b) compartmentalising genetic elements into microcapsules;
(c) expressing the genetic elements to produce their respective gene products within the microcapsules;
(d) sorting the genetic elements which produce the gene product(s) having the desired activity using the changed optical properties of the genetic elements; and
(e) expressing the gene product having the desired activity.

In accordance with the third aspect, step (a) preferably comprises preparing a repertoire of genetic elements, wherein each genetic element encodes a potentially differing gene product. Repertoires may be generated by conventional techniques, such as those employed for the generation of libraries intended for selection by methods such as phage display. Gene products having the desired activity may be selected from the repertoire, according to the present invention, according to their ability to modify the optical properties of the genetic elements in a manner which differs (i.e., by at least 10% in at least one optical property) from that of other gene products. For example, desired gene products may modify the optical properties to a greater extent than other gene products, or to a lesser extent, including not at all.

In a fourth aspect, the invention provides a method for screening a compound or compounds capable of modulation the activity of a gene product, the expression of which may result, directly or indirectly, in the modification of the optical properties of a genetic element encoding it, comprising the steps of:
(a) preparing a repertoire of genetic elements encoding gene product;
(b) compartmentalising genetic elements into microcapsules;
(c) expressing the genetic elements to produce their respective gene products within the microcapsules;
(d) sorting the genetic elements which produce the gene product(s) having the desired activity using the changed optical properties of the genetic elements; and
(e) contacting a gene product having the desired activity with the compound or compounds and monitoring the modulation of an activity of the gene product by the compound or compounds.

Advantageously, the method further comprises the step of:
(g) identifying the compound or compounds capable of modulating the activity of the gene product and synthesising said compound or compounds.

This selection system can be configured to select for RNA, DNA or protein molecules with catalytic, regulatory or binding activity.

Panel A: light scattering characteristics of beads and gate for single beads (R1). Panel B: fluorescence from microbeads (gated through R1) from reactions with CDNB. Panel C: fluorescence from microbeads (gated through R1) from reactions with CNB. Signals from microbeads from reactions with and without GST M2-2 are annotated +enz and −enz respectively. Signals from microbeads from reactions which were UV irradiated and those which were not are annotated +UV and −UV respectively.

Figure 10:
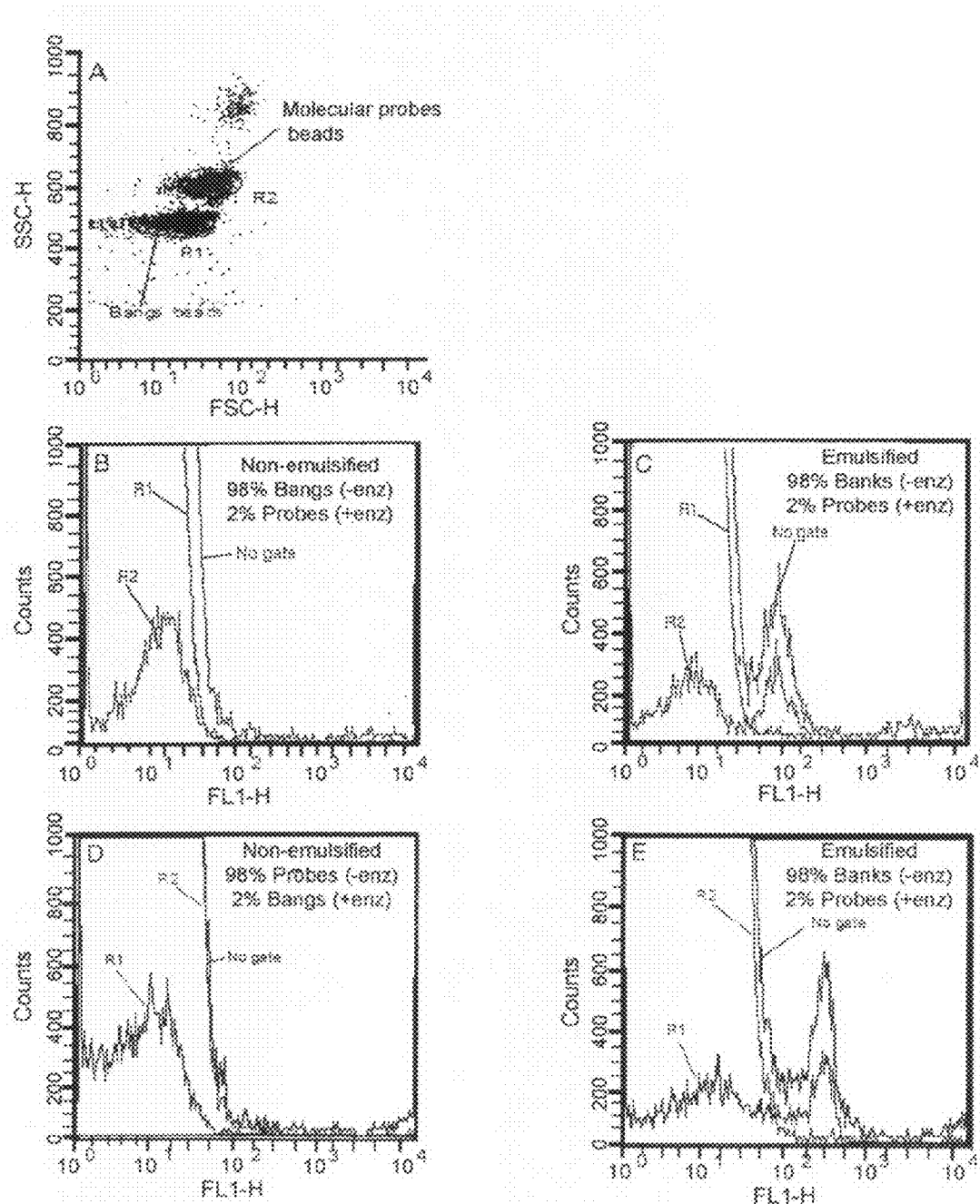

FIG. 10. Flow cytometry can be used to distinguish beads from aqueous compartments of an emulsion containing GST M2-2 from beads from compartments without GST M2-2 by using caged-biotinylated-βAla-GSH and CNB as substrates.

Panel A: light scattering characteristics of a mixture of a mixture of 1.0 μm diameter nonfluorescent neutravidin labelled microspheres (Molecular Probes, F-8777) or 0.93 μm diameter streptavidin-coated polystyrene beads (Bangs Laboratories) and gates set for single Bangs beads (R1) and single Molecular Probes beads (R2). Panel B: fluorescence from microbeads taken from a non-emulsified mixture of 98% Bangs beads (without GST) and 2% Molecular Probes beads (with GST). Panel C: fluorescence from microbeads taken from a mixture of two emulsions in a ratio of 98% emulsion containing Bangs beads (without GST) and an emulsion containing 2% Molecular Probes beads (with GST). Panel D: fluorescence from microbeads taken from a non-emulsified mixture of 98% Molecular Probes beads (without GST) and 2% Bangs beads (with GST). Panel E: fluorescence from microbeads taken from a mixture of two emulsions in a ratio of 98% emulsion containing Molecular Probes beads (without GST) and an emulsion containing 2% Bangs beads (with GST). Fluorescence of ungated beads (No gate), beads gated through R1 (R1) and beads gated through R2 (R2) are overlayed.

Figure 11:
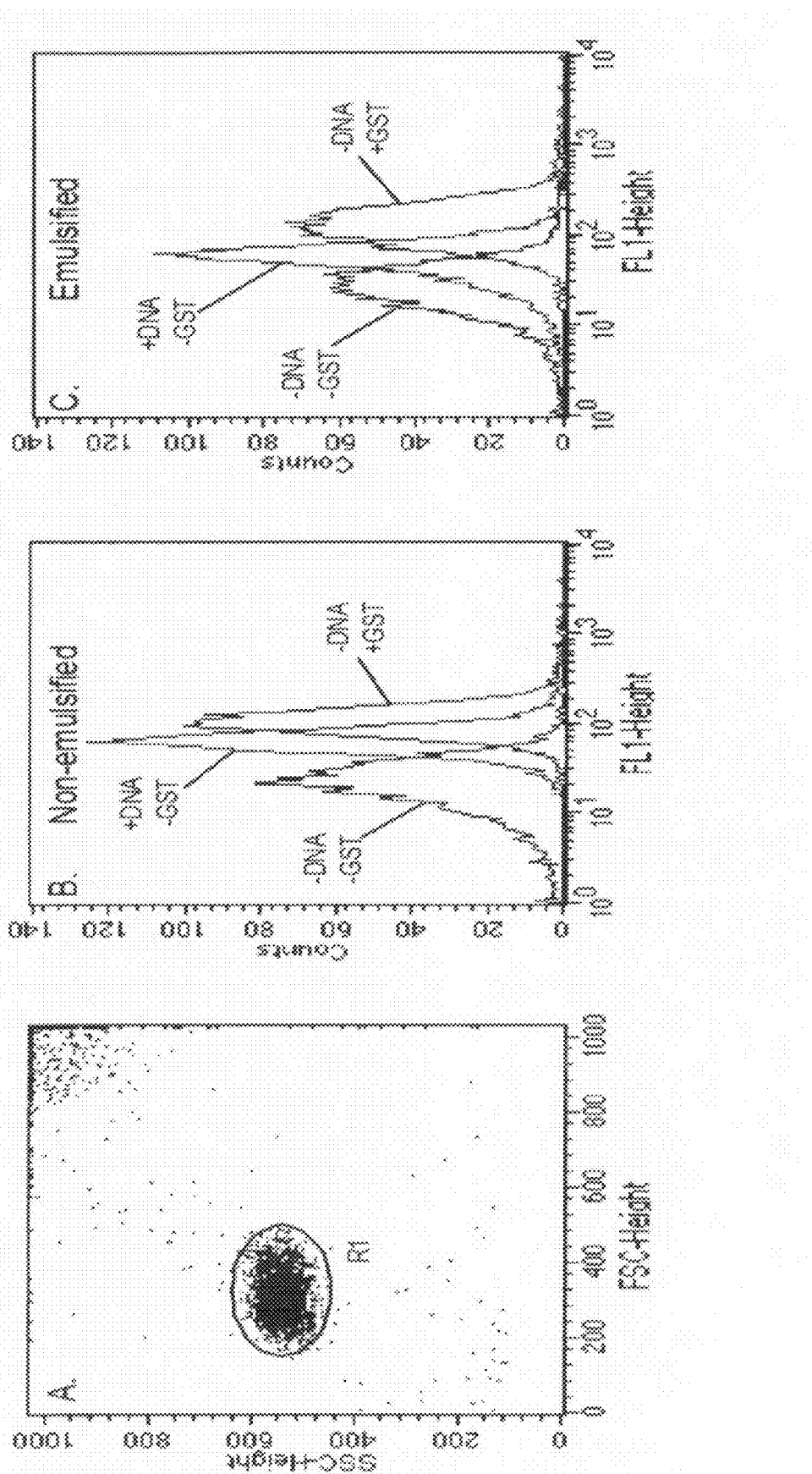

FIG. 11. Human GST M2-2 transcribed and translated in vitro in the aqueous compartments of a water-in oil emulsion catalyses a reaction which gives rise to a change in the fluorescence properties of co-compartmentalised microspheres.

Panel A: light scattering characteristics of beads and gate for single beads (R1). Panel B: fluorescence from microbeads (gated through R1) from non-emulsified reactions. Panel C: fluorescence from microbeads (gated through R1) emulsified reactions. Signals from microbeads from reactions with and without GSTM2-2.LMB2-3 DNA are annotated +DNA and −DNA respectively. Signals from microbeads from reactions with and without recombinant GST M2-2 are annotated +GST and −GST respectively.

Figure 12:
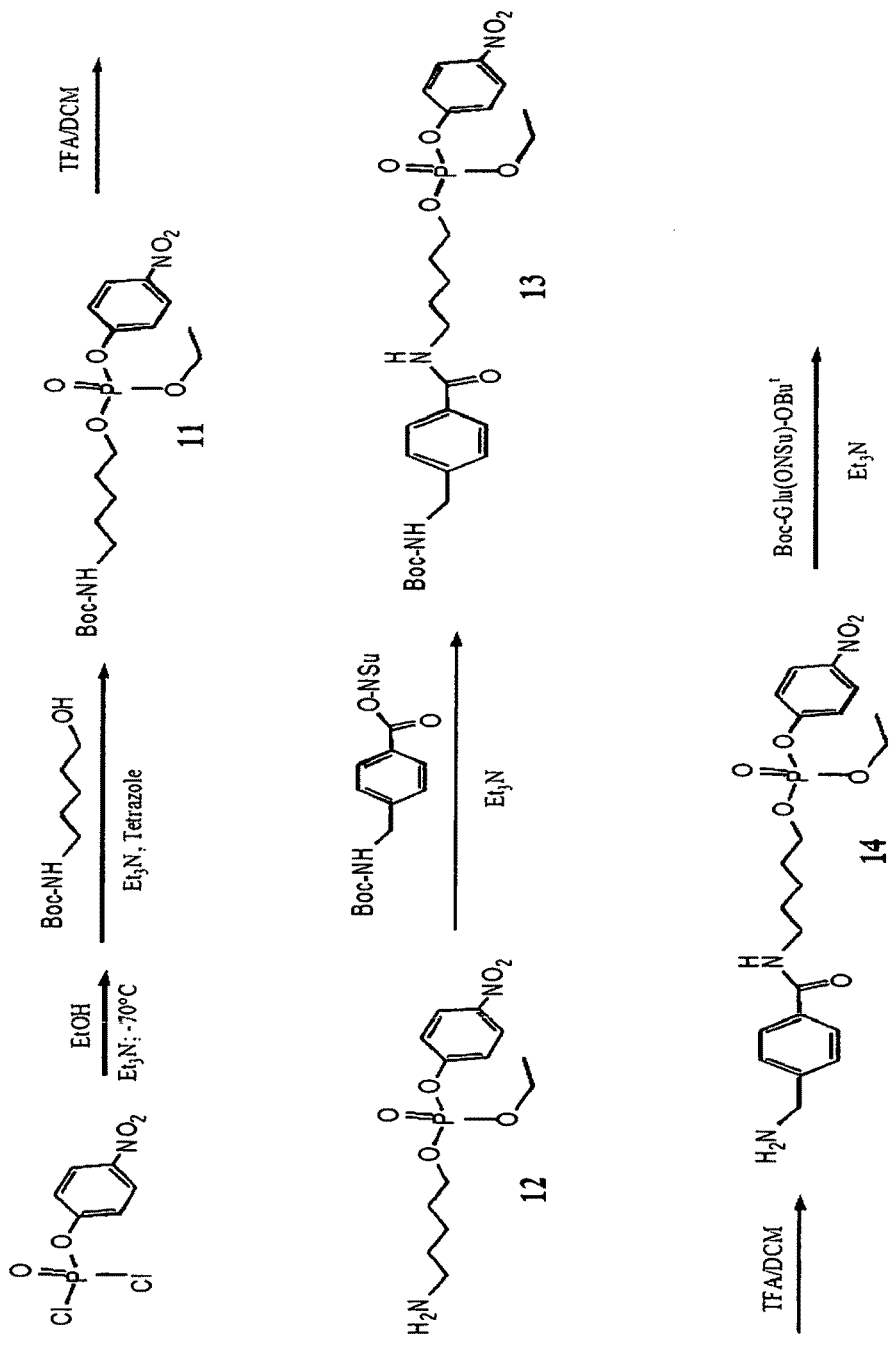
Figure 12:
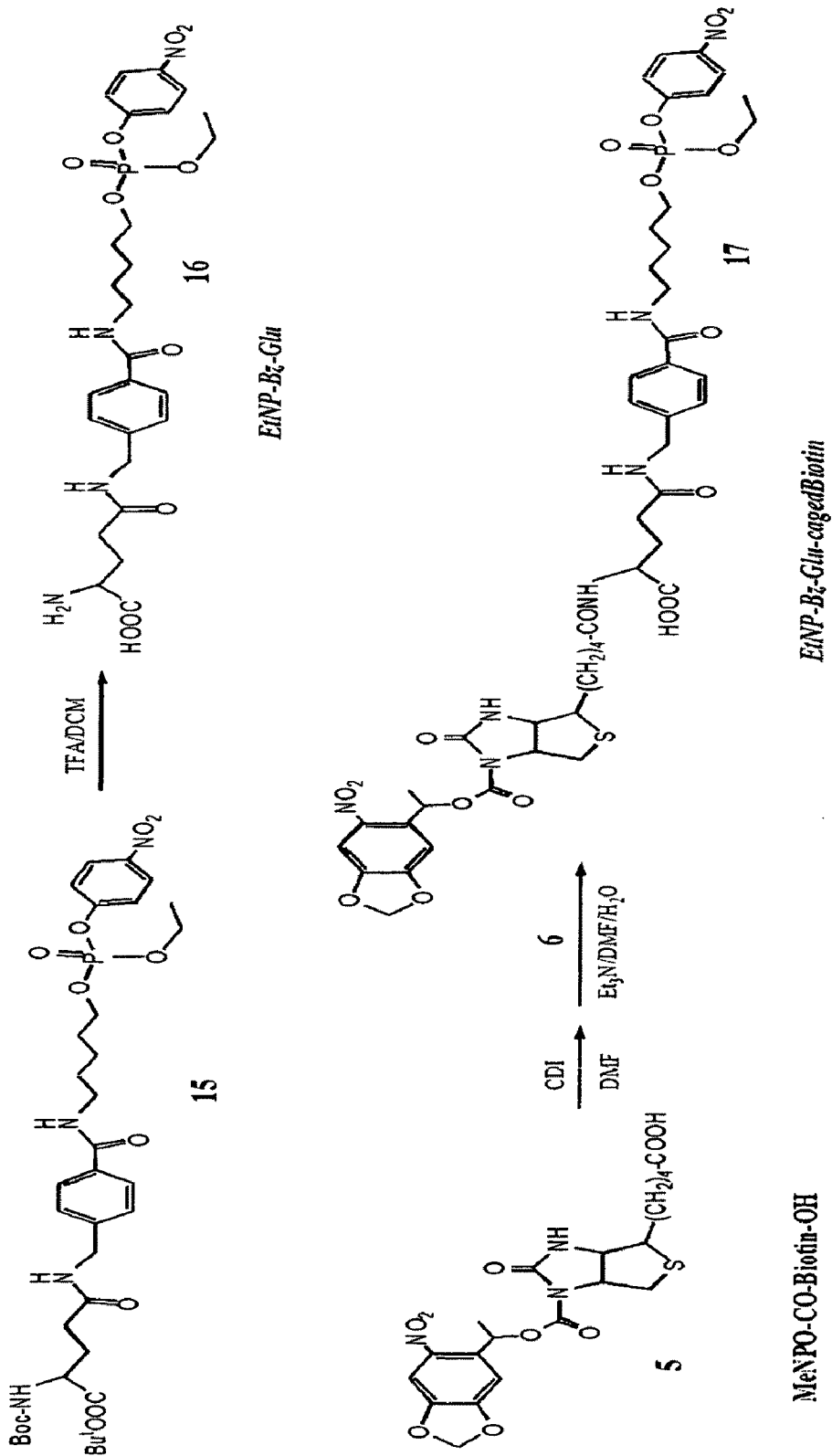

FIG. 12. Synthesis of the caged-biotinylated substrate EtNP-BzGlu-cagedBiotin (17).

Figure 13:
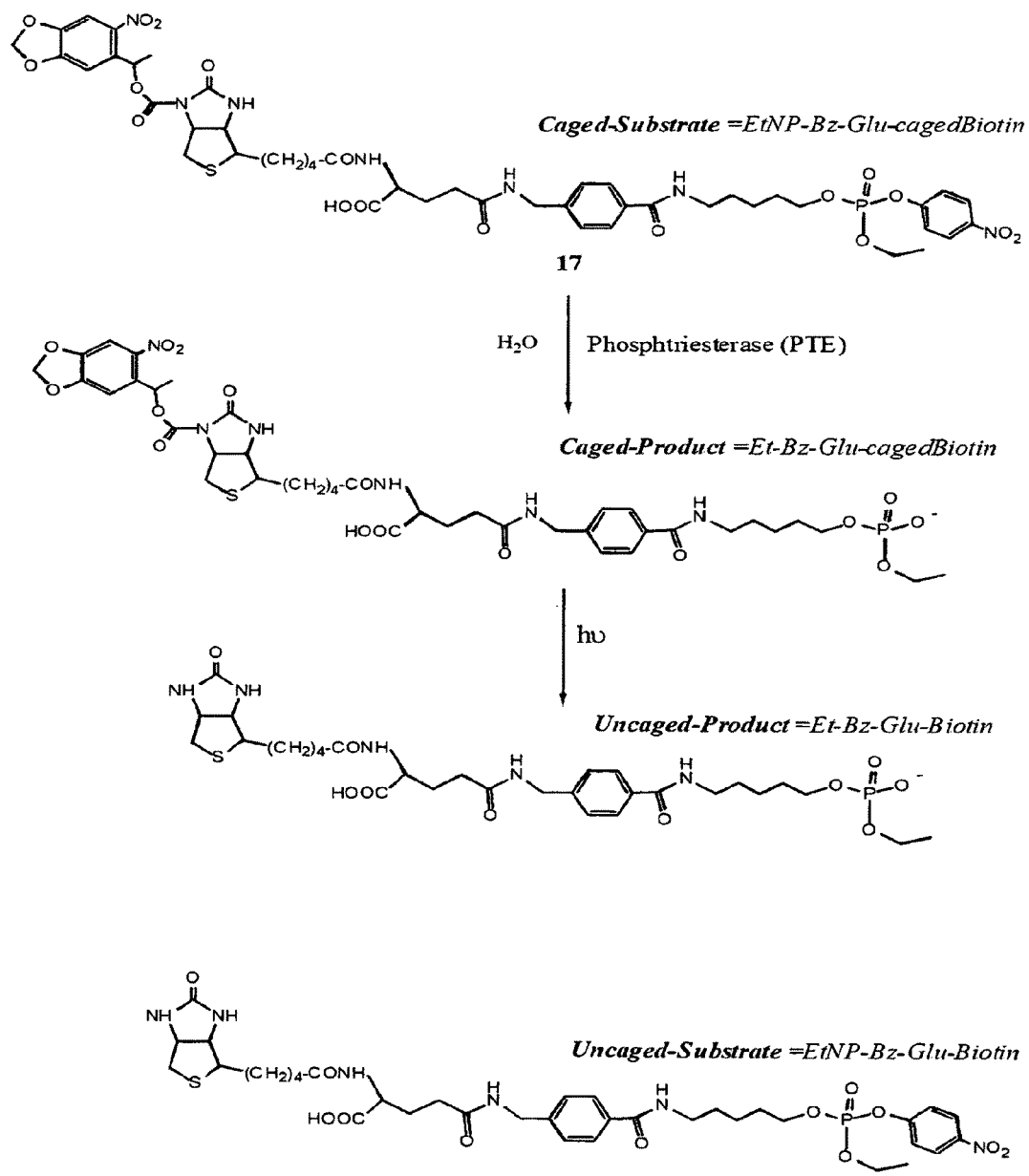

FIG. 13. Hydrolysis of the PTE substrate EtNP-Bz-Glu-cagedBiotin (17) to yield the product Et-Bz-Glu-cagedBiotin, and uncaging of both substrate and product to yield the corresponding biotinylated substrate (EtNP-Bz-Glu-Biotin) and product (EtNP-Bz-Glu-Biotin)

Figure 14:
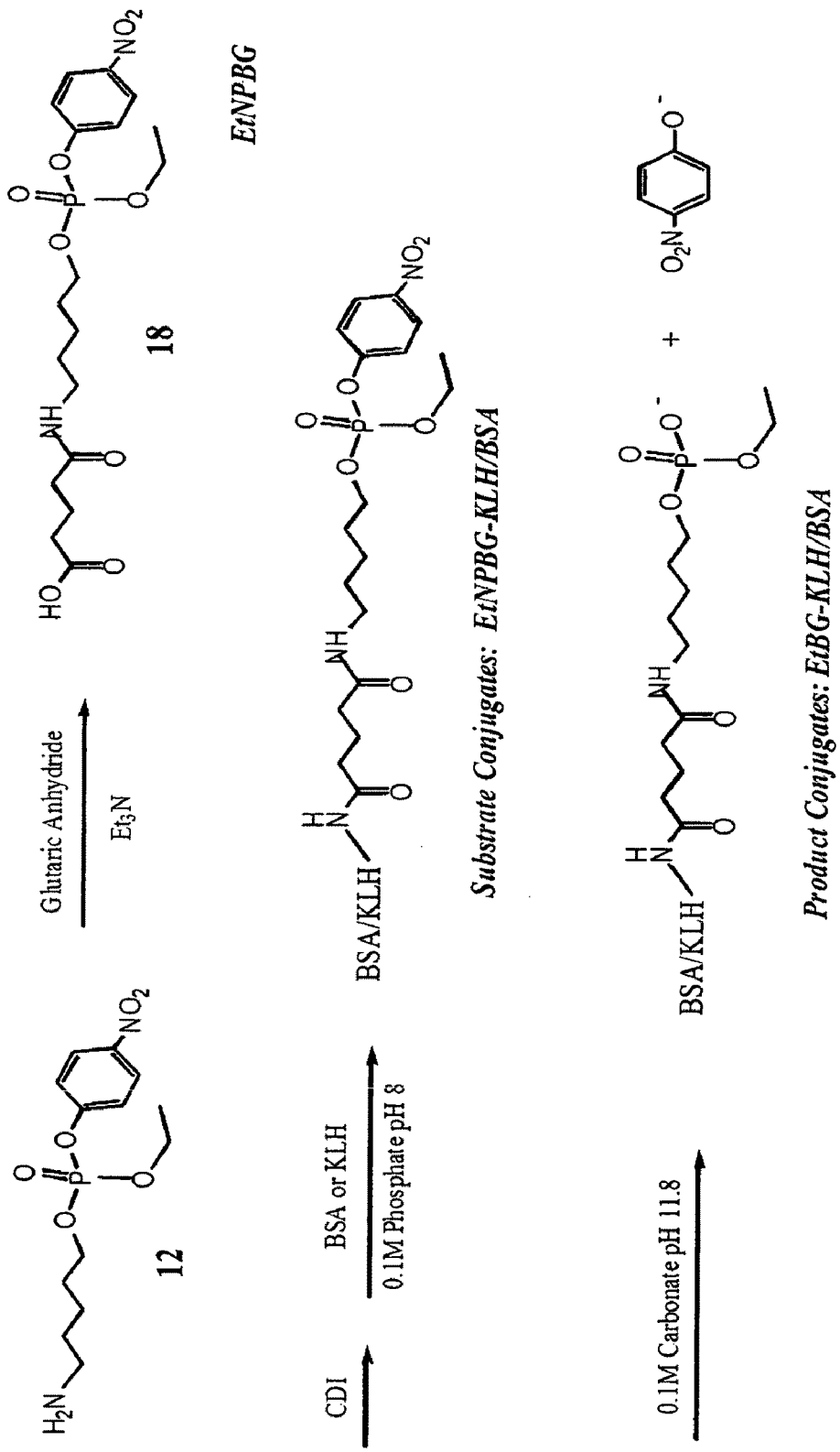

FIG. 14. Preparation of protein conjugates of a PTE substrate and product for immunisation and ELISA.

Figure 15:
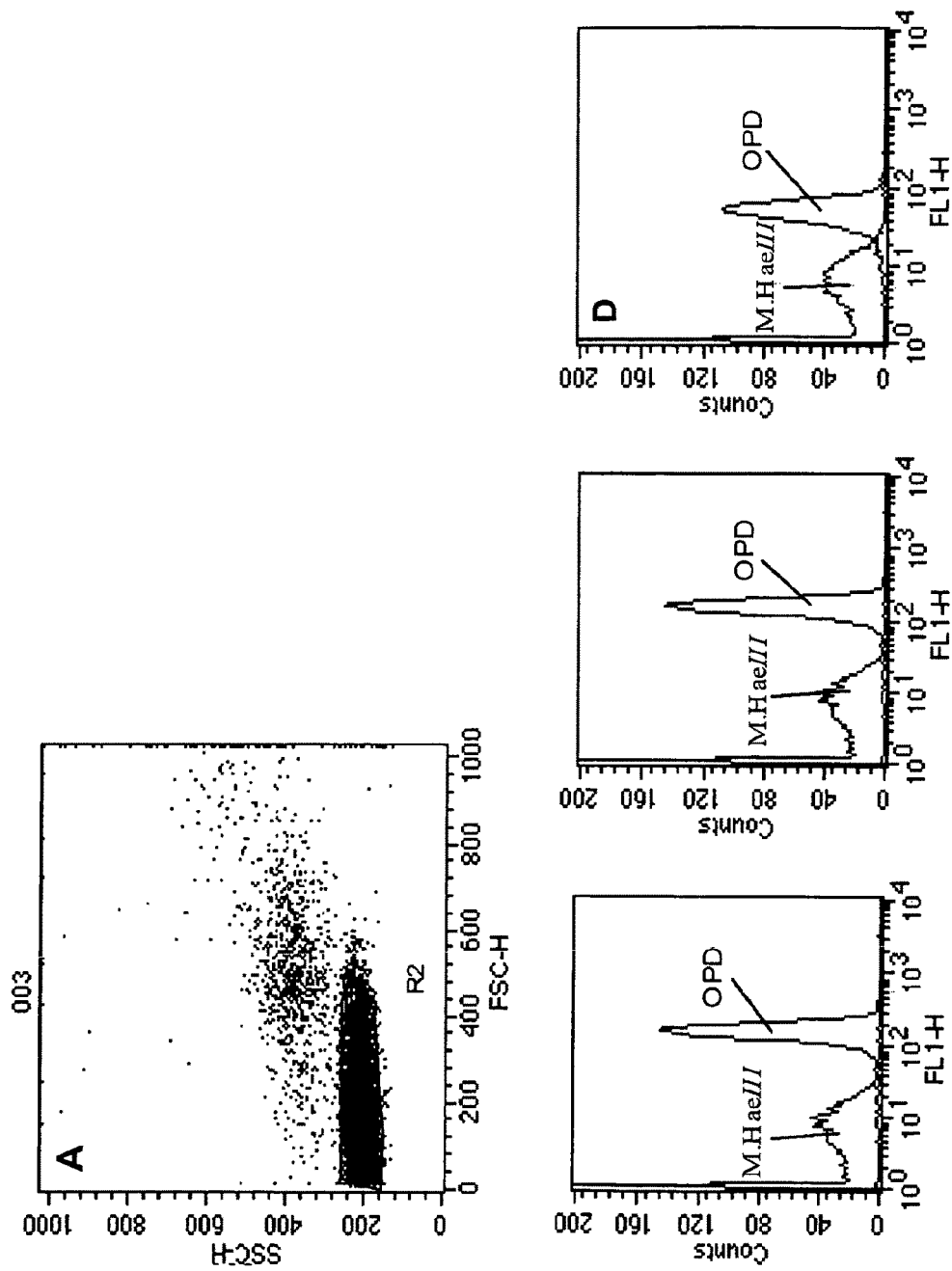

FIG. 15. PTE catalyses the reaction of EtNP-Bz-Glu-cagedBiotin in the presence of streptavidin-coated beads, and the reaction products uncaged by UV irradiation, are captured on beads and detected using fluorescently labelled anti-product antibodies and flow cytometry.

Panel A: light scattering characteristics of the beads and gate selected for single beads (R2). Panel B: fluorescence from beads (gated through R2) from reactions with 10 μM EtNP-Bz-Glu-cagedBiotin in the presence of in vitro translated OPD.LMB3-2biotin DNA fragments (OPD) or M.HaeIII.LMB3-2biotin DNA fragments (M.HaeIII). Panel C: As B but with 20 μM EtNP-Bz-Glu-cagedBiotin. Panel D: As B but with 50 μM EtNP-Bz-Glu-cagedBiotin.

Figure 16:
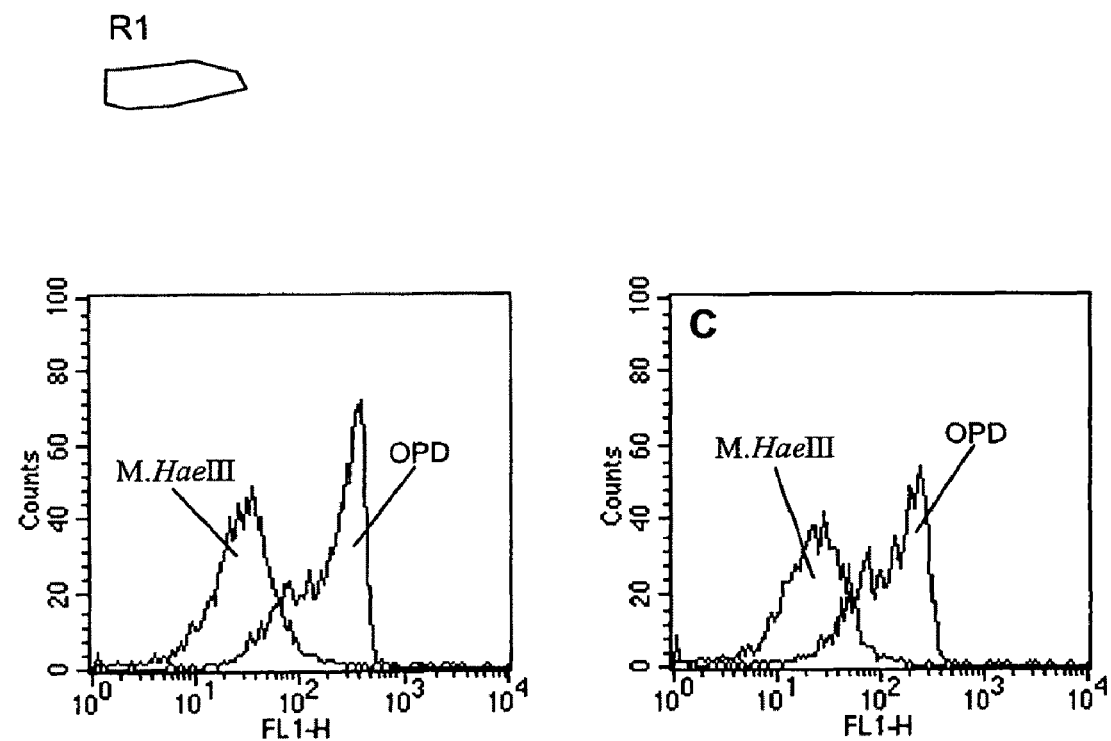

FIG. 16. Reaction of EtNP-Bz-Glu-cagedBiotin in the presence of beads to which genetic elements encoding the phosphotriesterase tagged with the Flag peptide (N-Flag-OPD.LMB3-2biotin) or another enzyme (N-Flag-MHaeII-I.LMB3-2biotin) were attached alongside with an antibody that binds the Flag peptide. The beads were reacted and subsequently analysed by flow-cytometry as described in the text.

Panel A: light scattering characteristics of beads and gate for single beads (R1). Panel B: fluorescence from microbeads (gated through R1) to which were attached N-Flag-OP- D.LMB3-2biotin DNA fragments (OPD) or M.HaeII-I.LMB3-2biotin DNA fragments (M.HaeIII) from reactions with 12.5 µM EtNP-Bz-Glu-cagedBiotin. Panel C: As B but with 25 µM EtNP-Bz-Glu-caged-Biotin.

Figure 17:
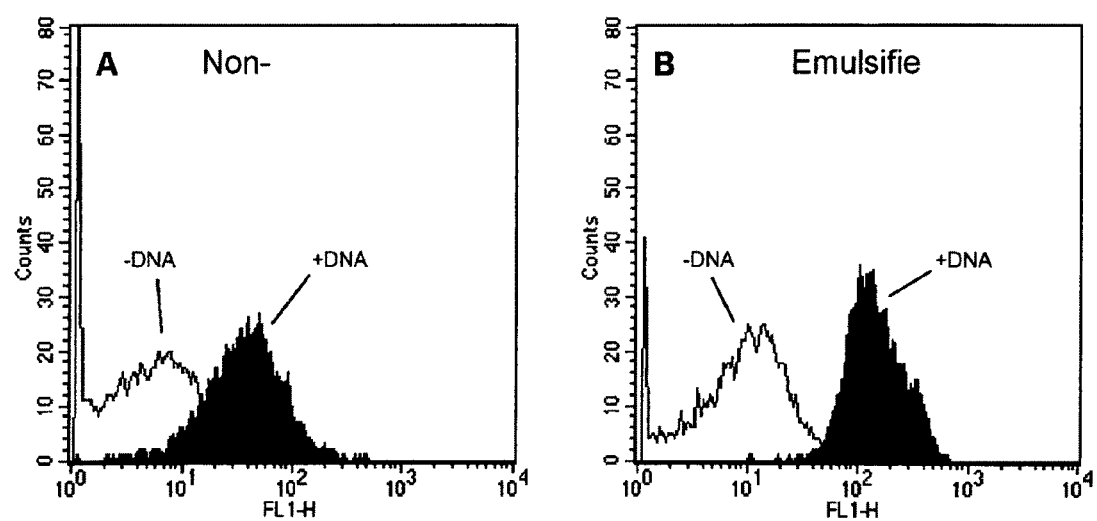

FIG. 17. *E. coli* BirA transcribed and translated in vitro catalyses a reaction which gives rise to a change in the fluorescence properties of substrate-labelled microspheres in the aqueous compartments of a water-in oil emulsion and in bulk solution.

Figure 18:
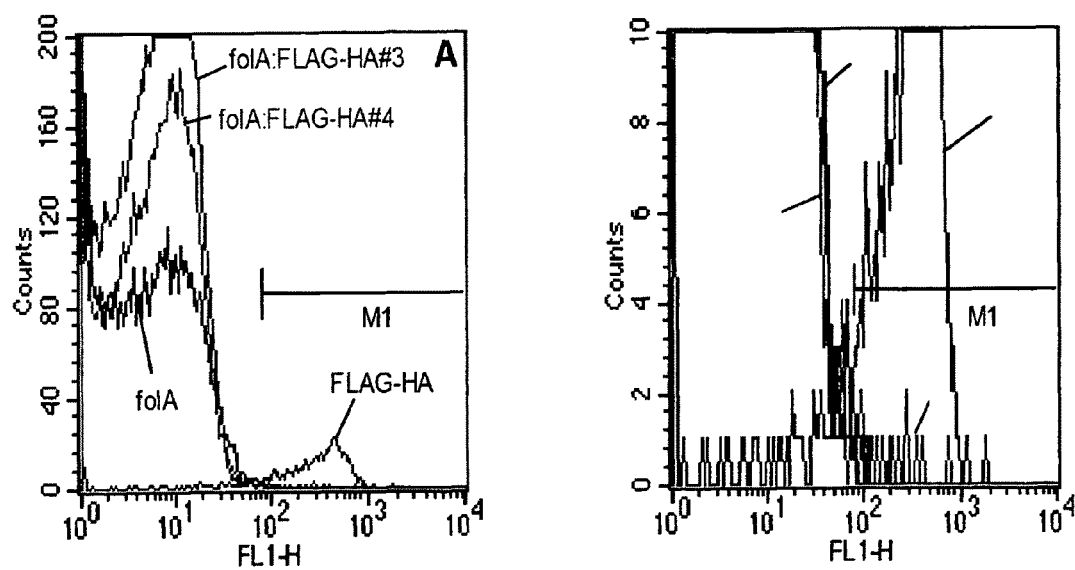

FIG. 18. Flow cytometric analysis of samples prepared for the sorting experiment.

Figure 19:
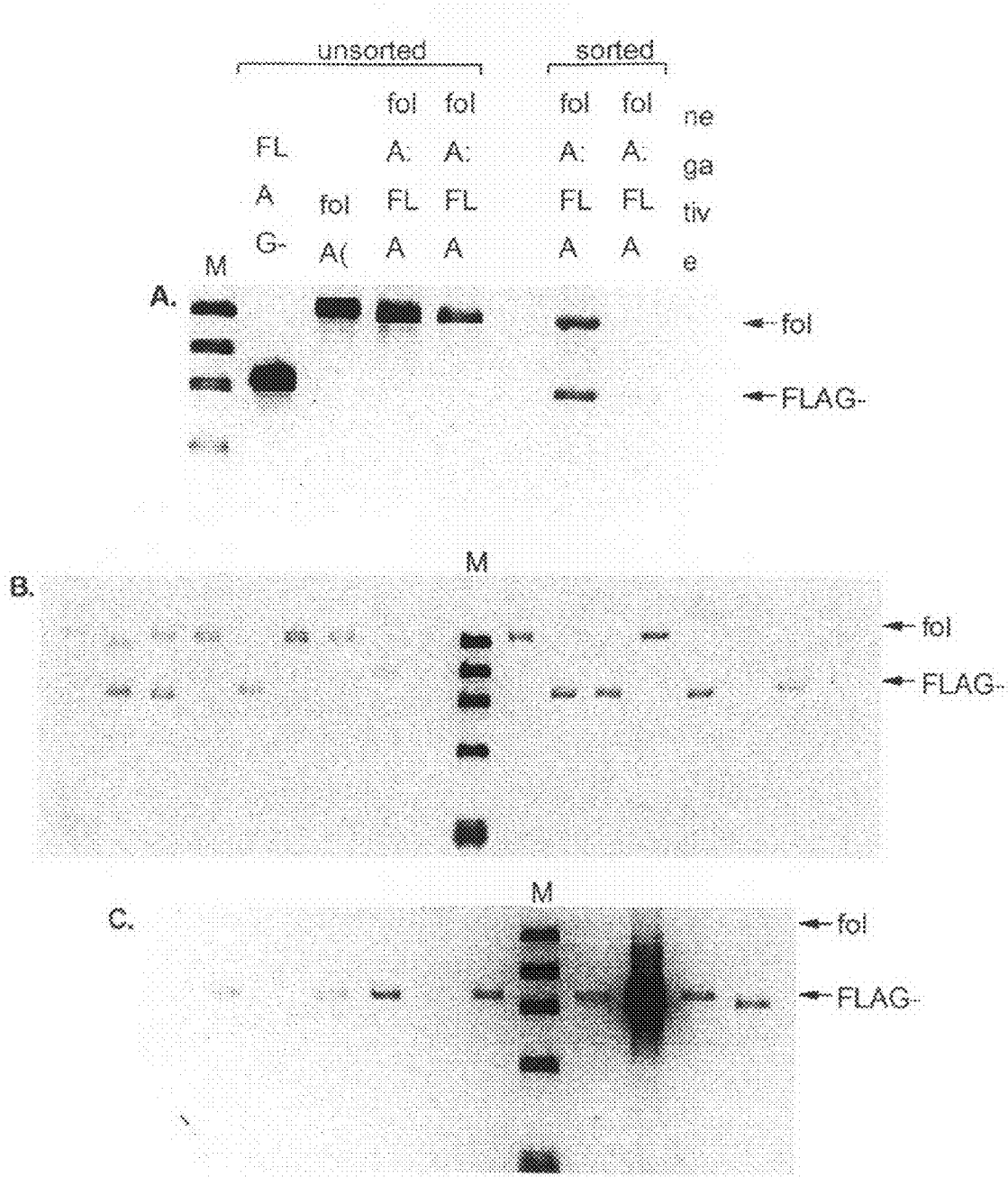

FIG. 19. Fluorescence-activated flow cytometric sorting of the genetic elements.

Panel A: Samples #1 to #4 before sorting and after sorting. Panel B: Genes recovered from individual beads sorted from sample #3 sorted into a 96-well plate. Panel C: Genes recovered from individual beads sorted from sample #4 sorted into a 96-well plate. DNA markers (M) are φX174-HaeIII digest.

(A) GENERAL DESCRIPTION

The microcapsules of the present invention require appropriate physical properties to allow the working of the invention.

First, to ensure that the genetic elements and gene products may not diffuse between microcapsules, the contents of each microcapsule are preferably isolated from the contents of the surrounding microcapsules, so that there is no or little exchange of the genetic elements and gene products between the microcapsules over the timescale of the experiment.

Second, the method of the present invention requires that there are only a limited number of genetic elements per microcapsule. This ensures that the gene product of an individual genetic element will be isolated from other genetic elements. Thus, coupling between genetic element and gene product will be highly specific. The enrichment factor is greatest with on average one or fewer genetic elements per microcapsule, the linkage between nucleic acid and the activity of the encoded gene product being as tight as is possible, since the gene product of an individual genetic element will be isolated from the products of all other genetic elements. However, even if the theoretically optimal situation of, on average, a single genetic element or less per microcapsule is not used, a ratio of 5, 10, 50, 100 or 1000 or more genetic elements per microcapsule may prove beneficial in sorting a large library. Subsequent rounds of sorting, including renewed encapsulation with differing genetic element distribution, will permit more stringent sorting of the genetic elements. Preferably, there is a single genetic element, or fewer, per microcapsule.

Third, the formation and the composition of the microcapsules advantageously does not abolish the function of the machinery the expression of the genetic elements and the activity of the gene products.

The appropriate system(s) may vary depending on the precise nature of the requirements in each application of the invention, as will be apparent to the skilled person.

A wide variety of microencapsulation procedures are available (see Benita, 1996) and may be used to create the microcapsules used in accordance with the present invention. Indeed, more than 200 microencapsulation methods have been identified in the literature (Finch, 1993).

These include membrane enveloped aqueous vesicles such as lipid vesicles (liposomes) (New, 1990) and non-ionic surfactant vesicles (van Hal et al., 1996). These are closed-membranous capsules of single or multiple bilayers of non-covalently assembled molecules, with each bilayer separated from its neighbour by an aqueous compartment. In the case of liposomes the membrane is composed of lipid molecules; these are usually phospholipids but sterols such as cholesterol may also be incorporated into the membranes (New, 1990). A variety of enzyme-catalysed biochemical reactions, including RNA and DNA polymerisation, can be performed within liposomes (Chakrabarti et al., 1994; Oberholzer et al., 1995a; Oberholzer et al., 1995b; Walde et al., 1994; Wick & Luisi, 1996).

With a membrane-enveloped vesicle system much of the aqueous phase is outside the vesicles and is therefore non-compartmentalised. This continuous, aqueous phase is removed or the biological systems in it inhibited or destroyed (for example, by digestion of nucleic acids with DNase or RNase) in order that the reactions are limited to the microcapsules (Luisi et al., 1987).

Enzyme-catalysed biochemical reactions have also been demonstrated in microcapsules generated by a variety of other methods. Many enzymes are active in reverse micellar solutions (Bru & Walde, 1991; Bru & Walde, 1993; Creagh et al., 1993; Haber et al., 1993; Kumar et al., 1989; Luisi & B., 1987; Mao & Walde, 1991; Mao et al., 1992; Perez et al., 1992; Walde et al., 1994; Walde et al., 1993; Walde et al., 1988) such as the AOT-isooctane-water system (Menger & Yamada, 1979).

Microcapsules can also be generated by interfacial polymerisation and interfacial complexation (Whateley, 1996). Microcapsules of this sort can have rigid, nonpermeable membranes, or semipermeable membranes. Semipermeable microcapsules bordered by cellulose nitrate membranes, polyamide membranes and lipid-polyamide membranes can all support biochemical reactions, including multienzyme systems (Chang, 1987; Chang, 1992; Lim, 1984). Alginate/polylysine microcapsules (Lim & Sun, 1980), which can be formed under very mild conditions, have also proven to be very biocompatible, providing, for example, an effective method of encapsulating living cells and tissues (Chang, 1992; Sun et al., 1992).

Non-membranous microencapsulation systems based on phase partitioning of an aqueous environment in a colloidal system, such as an emulsion, may also be used.

Preferably, the microcapsules of the present invention are formed from emulsions; heterogeneous systems of two immiscible liquid phases with one of the phases dispersed in the other as droplets of microscopic or colloidal size (Becher, 1957; Sherman, 1968; Lissant, 1974; Lissant, 1984).

Emulsions may be produced from any suitable combination of immiscible liquids. Preferably the emulsion of the present invention has water (containing the biochemical components) as the phase present in the form of finely divided droplets (the disperse, internal or discontinuous phase) and a hydrophobic, immiscible liquid (an oil') as the matrix in which these droplets are suspended (the nondisperse, continuous or external phase). Such emulsions are termed "water-in-oil" (W/O). This has the advantage that the entire aqueous phase containing the biochemical components is compartmentalised in discreet droplets (the internal phase). The external phase, being a hydrophobic oil, generally contains none of the biochemical components and hence is inert.

The emulsion may be stabilised by addition of one or more surface-active agents (surfactants). These surfactants are termed emulsifying agents and act at the water/oil interface to prevent (or at least delay) separation of the phases. Many oils and many emulsifiers can be used for the generation of water-in-oil emulsions; a recent compilation listed over 16,000 surfactants, many of which are used as emulsifying agents (Ash and Ash, 1993). Suitable oils include light white mineral oil and non-ionic surfactants (Schick, 1966) such as sorbitan monooleate (Span™80; ICI) and polyoxyethylenesorbitan monooleate (Tween™80; ICI).

The use of anionic surfactants may also be beneficial. Suitable surfactants include sodium cholate and sodium taurocholate. Particularly preferred is sodium deoxycholate, preferably at a concentration of 0.5% w/v, or below. Inclusion of such surfactants can in some cases increase the expression of the genetic elements and/or the activity of the gene products. Addition of some anionic surfactants to a non-emulsified reaction mixture completely abolishes translation. During emulsification, however, the surfactant is transferred from the aqueous phase into the interface and activity is restored. Addition of an anionic surfactant to the mixtures to be emulsified ensures that reactions proceed only after compartmentalisation.

Creation of an emulsion generally requires the application of mechanical energy to force the phases together. There are a variety of flays of doing this which utilise a variety of mechanical devices, including stirrers (such as magnetic stirbars, propeller and turbine stirrers, paddle devices and whisks), homogenisers (including rotor-stator homogenisers, high-pressure valve homogenisers and jet homogenisers), colloid mills, ultrasound and 'membrane emulsification' devices (Becher, 1957; Dickinson, 1994).

Aqueous microcapsules formed in water-in-oil emulsions are generally stable with little if any exchange of genetic elements or gene products between microcapsules. Additionally, we have demonstrated that several biochemical reactions proceed in emulsion microcapsules. Moreover, complicated biochemical processes, notably gene transcription and translation are also active in emulsion microcapsules. The technology exists to create emulsions with volumes all the way up to industrial scales of thousands of litres (Becher, 1957; Sherman, 1968; Lissant, 1974; Lissant, 1984).

The preferred microcapsule size will vary depending upon the precise requirements of any individual selection process that is to be performed according to the present invention. In all cases, there will be an optimal balance between gene library size, the required enrichment and the required concentration of components in the individual microcapsules to achieve efficient expression and reactivity of the gene products.

The processes of expression occurs within each individual microcapsule provided by the present invention. Both in vitro transcription and coupled transcription-translation become less efficient at sub-nanomolar DNA concentrations. Because of the requirement for only a limited number of DNA molecules to be present in each microcapsule, this therefore sets a practical upper limit on the possible microcapsule size. Preferably, the mean volume of the microcapsules is less that $5.2 \times 10^{-16}$ m$^3$, (corresponding to a spherical microcapsule of diameter less than 10 µm, more preferably less than $6.5 \times 10^{-17}$ m$^3$ (5 µm diameter), more preferably about $4.2 \times 10^{-18}$ m$^3$ (2 µm diameter) and ideally about $9 \times 10^{-18}$ m$^3$ (2.6 µm diameter).

The effective DNA or RNA concentration in the microcapsules may be artificially increased by various methods that will be well-known to those versed in the art. These include, for example, the addition of volume excluding chemicals such as polyethylene glycols (PEG) and a variety of gene amplification techniques, including transcription using RNA polymerases including those from bacteria such as *E. coli* (Roberts, 1969; Blattner and Dahlberg, 1972; Roberts et al. 1975; Rosenberg et al., 1975), eukaryotes e.g. (Weil et al., 1979; Manley et al., 1983) and bacteriophage such as T7, T3 and SP6 (Melton et al., 1984); the polymerase chain reaction (PCR) (Saiki et al., 1988); Qb replicase amplification (Miele et al., 1983; Cahill et al., 1991; Chetverin and Spirin, 1995; Katanaev et al., 1995); the ligase chain reaction (LCR) (Landegren et al., 1988; Barany, 1991); and self-sustained sequence replication system (Fahy et al., 1991) and strand displacement amplification (Walker et al., 1992). Gene amplification techniques requiring thermal cycling such as PCR and LCR may be used if the emulsions and the in vitro transcription or coupled transcription-translation systems are thermostable (for example, the coupled transcription-translation systems can be made from a thermostable organism such as *Thermus aquaticus*).

Increasing the effective local nucleic acid concentration enables larger microcapsules to be used effectively. This allows a preferred practical upper limit to the microcapsule volume of about $5.2 \times 10^6$ m$^3$ (corresponding to a sphere of diameter 10 µm).

The microcapsule size is preferably sufficiently large to accommodate all of the required components of the biochemical reactions that are needed to occur within the microcapsule. For example, in vitro, both transcription reactions and coupled transcription-translation reactions require a total nucleoside triphosphate concentration of about 2 mM.

For example, in order to transcribe a gene to a single short RNA molecule of 500 bases in length, this would require a minimum of 500 molecules of nucleoside triphosphate per microcapsule ($8.33 \times 10^{-22}$ moles). In order to constitute a 2 mM solution, this number of molecules is contained within a microcapsule of volume $4.17 \times 10^{-19}$ litres ($4.17 \times 10^{-22}$ m$^3$ which if spherical would have a diameter of 93 nm.

Furthermore, particularly in the case of reactions involving translation, it is to be noted that the ribosomes necessary for the translation to occur are themselves approximately 20 nm in diameter. Hence, the preferred lower limit for microcapsules is a diameter of approximately 0.1 µm (100 nm).

Therefore, the microcapsule volume is preferably of the order of between $5.2 \times 10^{-22}$ m$^3$ and $5.2 \times 10^{-16}$ m$^3$ corresponding to a sphere of diameter between 0.1 µm and 10 µm, more preferably of between about $5.2 \times 10^{-19}$ m3 and $6.5 \times 10^{-17}$ m$^3$ (1 µm and 5 µm). Sphere diameters of about 2.6 µm are most advantageous.

It is no coincidence that the preferred dimensions of the compartments (droplets of 2.6 µm mean diameter) closely resemble those of bacteria, for example, *Escherichia* are 1.1-1.5×2.0-6.0 µm rods and *Azotobacter* are 1.5-2.0 µm diameter ovoid cells. In its simplest form, Darwinian evolution is based on a 'one genotype one phenotype' mechanism. The concentration of a single compartmentalised gene, or genome, drops from 0.4 nM in a compartment of 2 µm diameter, to 25 pM in a compartment of 5 µm diameter. The prokaryotic transcription/translation machinery has evolved to operate in compartments of ~1-2 µm diameter, where single genes are at approximately nanomolar concentrations. A single gene, in a compartment of 2.6 µm diameter is at a concentration of 0.2 nM. This gene concentration is high enough for efficient translation. Compartmentalisation in such a volume also ensures that even if only a single molecule of the gene product is formed it is present at about 0.2 nM, which is important if the gene product is to have a modifying activity of the genetic element itself. The volume of the microcapsule is thus selected bearing in mind not only the requirements for transcription and translation of the genetic element, but also the modifying activity required of the gene product in the method of the invention.

The size of emulsion microcapsules may be varied simply by tailoring the emulsion conditions used to form the emulsion according to requirements of the selection system. The larger the microcapsule size, the larger is the volume that will be required to encapsulate a given genetic element library, since the ultimately limiting factor will be the size of the microcapsule and thus the number of microcapsules possible per unit volume.

The size of the microcapsules is selected not only having regard to the requirements of the transcription/translation system, but also those of the selection system employed for the genetic element. Thus, the components of the selection system, such as a chemical modification system, may require reaction volumes and/or reagent concentrations which are not optimal for transcription/translation. As set forth herein, such requirements may be accommodated by a secondary re-encapsulation step; moreover, they may be accommodated by selecting the microcapsule size in order to maximise transcription/translation and selection as a whole. Empirical determination of optimal microcapsule volume and reagent concentration, for example as set forth herein, is preferred.

A "genetic element" in accordance with the present invention is as described above. Preferably, a genetic element is a molecule or construct selected from the group consisting of a DNA molecule, an RNA molecule, a partially or wholly artificial nucleic acid molecule consisting of exclusively synthetic or a mixture of naturally-occurring and synthetic bases, any one of the foregoing linked to a polypeptide, and any one of the foregoing linked to any other molecular group or construct. Advantageously, the other molecular group or construct may be selected from the group consisting of nucleic acids, polymeric substances, particularly beads, for example polystyrene beads, and magnetic or paramagnetic substances such as magnetic or paramagnetic beads.

The nucleic acid portion of the genetic element may comprise suitable regulatory sequences, such as those required for efficient expression of the gene product, for example promoters, enhancers, translational initiation sequences, polyadenylation sequences, splice sites and the like.

As will be apparent from the following, in many cases the polypeptide or other molecular group or construct is a ligand or a substrate which directly or indirectly binds to or reacts with the gene product in order to alter the optical properties of the genetic element. This allows the sorting of the genetic element on the basis of the activity of the gene product. The ligand or substrate can be connected to the nucleic acid by a variety of means that will be apparent to those skilled in the art (see, for example, Hermanson, 1996).

One way in which the nucleic acid molecule may be linked to a ligand or substrate is through biotinylation. This can be done by PCR amplification with a 5'-biotinylation primer such that the biotin and nucleic acid are covalently linked.

The ligand or substrate can be attached to the modified nucleic acid by a variety of means that will be apparent to those of skill in the art (see, for example, Hermanson, 1996). A biotinylated nucleic acid may be coupled to a polystyrene or paramagnetic microbead (0.02 to approx. 5.0 µm in diameter) that is coated with avidin or streptavidin, that sill therefore bind the nucleic acid with very high affinity. This bead can be derivatised with substrate or ligand by any suitable method such as by adding biotinylated substrate or by covalent coupling.

Alternatively, a biotinylated nucleic acid may be coupled to avidin or streptavidin complexed to a large protein molecule such as thyroglobulin (669 Kd) or ferritin (440 Kd). This complex can be derivatised with substrate or ligand, for example by covalent coupling to the ε-amino group of lysines or through a non-covalent interaction such as biotin-avidin.

The substrate may be present in a form unlinked to the genetic element but containing an inactive "tag" that requires a further step to activate it such as photoactivation (e.g. of a "caged" biotin analogue, (Sundberg et al., 1995; Pirrung and Huang, 1996)). The catalyst to be selected then converts the substrate to product. The "tag" is then activated and the "tagged" substrate and/or product bound by a tag-binding molecule (e.g. avidin or streptavidin) complexed with the nucleic acid. The ratio of substrate to product attached to the nucleic acid via the "tag" will therefore reflect the ratio of the substrate and product in solution.

An alternative is to couple the nucleic acid to a product-specific antibody (or other product-specific molecule). In this scenario, the substrate (or one of the substrates) is present in each microcapsule unlinked to the genetic element, but has a molecular "tag" (for example biotin, DIG or DNP or a fluorescent group). When the catalyst to be selected converts the substrate to product, the product retains the "tag" and is then captured in the microcapsule by the product-specific antibody. In this way the genetic element only becomes associated with the "tag" when it encodes or produces an enzyme capable of converting substrate to product.

The terms "isolating", "sorting" and "selecting", as well as variations thereof, are used herein. Isolation, according to the present invention, refers to the process of separating an entity from a heterogeneous population, for example a mixture, such that it is free of at least one substance with which it was associated before the isolation process. In a preferred embodiment, isolation refers to purification of an entity essentially to homogeneity. Sorting of an entity refers to the process of preferentially isolating desired entities over undesired entities. In as far as this relates to isolation of the desired entities, the terms "isolating" and "sorting" are equivalent. The method of the present invention permits the sorting of desired genetic elements from pools (libraries or repertoires) of genetic elements which contain the desired genetic element. Selecting is used to refer to the process (including the sorting process) of isolating an entity according to a particular property thereof.

In a highly preferred application, the method of the present invention is useful for sorting libraries of genetic elements. The invention accordingly provides a method according to preceding aspects of the invention, wherein the genetic elements are isolated from a library of genetic elements encoding a repertoire of gene products. Herein, the terms "library", "repertoire" and "pool" are used according to their ordinary signification in the art, such that a library of genetic elements encodes a repertoire of gene products. In general, libraries are constructed from pools of genetic elements and have properties which facilitate sorting.

Initial selection of a genetic element from a genetic element library using the present invention will in most cases require the screening of a large number of variant genetic elements. Libraries of genetic elements can be created in a variety of different ways, including the following.

Pools of naturally occurring genetic elements can be cloned from genomic DNA or cDNA (Sambrook et al., 1989); for example, phage antibody libraries, made by PCR amplification repertoires of antibody genes from immunised or unimmunised donors have proved very effective sources of functional antibody fragments (Winter et al., 1994; Hoogenboom, 1997). Libraries of genes can also be made by encoding all (see for example Smith, 1985; Parmley and Smith, 1988) or part of genes (see for example Lowman et al., 1991) or pools of genes (see for example Nissim et al., 1994) by a randomised or doped synthetic oligonucleotide. Libraries can also be made by introducing mutations into a genetic element or pool of genetic elements 'randomly' by a variety of techniques in vivo, including; using mutator strains of bacteria such as *E. coli* mutD5 (Liao et al., 1986; Yamagishi et al., 1990; Low et al., 1996); using the antibody hypermutation system of B-lymphocytes (Yelamos et al., 1995). Random mutations can also be introduced both in vivo and in vitro by chemical mutagens, and ionising or UV irradiation (see Friedberg et al., 1995), or incorporation of mutagenic base analogues (Freese, 1959; Zaccolo et al., 1996). Random' mutations can also be introduced into genes in vitro during polymerisation for example by using error-prone polymerases (Leung et al., 1989).

Further diversification can be introduced by using homologous recombination either in vivo (see Kowalczykowski et al., 1994) or in vitro (Stemmer, 1994a; Stemmer, 1994b).

According to a further aspect of the present invention, therefore, there is provided a method of in vitro evolution comprising the steps of:

(a) selecting one or more genetic elements from a genetic element library according to the present invention;

(b) mutating the selected genetic element(s) in order to generate a further library of genetic elements encoding a repertoire to gene products; and (c) iteratively repeating steps (a) and (b) in order to obtain a gene product with enhanced activity.

Mutations may be introduced into the genetic elements(s) as set forth above.

The genetic elements according to the invention advantageously encode enzymes, preferably of pharmacological or industrial interest, activators or inhibitors, especially of biological systems, such as cellular signal transduction mechanisms, antibodies and fragments thereof, and other binding agents (e.g. transcription factors) suitable for diagnostic and therapeutic applications. In a preferred aspect, therefore, the invention permits the identification and isolation of clinically or industrially useful products. In a further aspect of the invention, there is provided a product when isolated by the method of the invention.

The selection of suitable encapsulation conditions is desirable. Depending on the complexity and size of the library to be screened, it may be beneficial to set up the encapsulation procedure such that 1 or less than 1 genetic element is encapsulated per microcapsule. This will provide the greatest power of resolution. Where the library is larger and/or more complex, however, this may be impracticable; it may be preferable to encapsulate several genetic elements together and rely on repeated application of the method of the invention to achieve sorting of the desired activity. A combination of encapsulation procedures may be used to obtain the desired enrichment.

Theoretical studies indicate that the larger the number of genetic element variants created the more likely it is that a molecule will be created with the properties desired (see Perelson and Oster, 1979 for a description of how this applies to repertoires of antibodies). Recently it has also been confirmed practically that larger phage-antibody repertoires do indeed give rise to more antibodies with better binding affinities than smaller repertoires (Griffiths et al., 1994). To ensure that rare variants are generated and thus are capable of being selected, a large library size is desirable. Thus, the use of optimally small microcapsules is beneficial.

The largest repertoire created to date using methods that require an in vivo step (phage-display and LacI systems) has been a $1.6 \times 10^{11}$ clone phage-peptide library which required the fermentation of 15 litres of bacteria (Fisch et al., 1996). SELEX experiments are often carried out on very large numbers of variants (up to $10^{15}$).

Using the present invention, at a preferred microcapsule diameter of 2.6 μm, a repertoire size of at least $10^{11}$ can be selected using 1 ml aqueous phase in a 20 ml emulsion.

In addition to the genetic elements described above, the microcapsules according to the invention will comprise further components required for the sorting process to take place. Other components of the system will for example comprise those necessary for transcription and/or translation of the genetic element. These are selected for the requirements of a specific system from the following; a suitable buffer, an in vitro transcription/replication system and/or an in vitro translation system containing all the necessary ingredients, enzymes and cofactors, RNA polymerase, nucleotides, nucleic acids (natural or synthetic), transfer RNAs, ribosomes and amino acids, and the substrates of the reaction of interest in order to allow selection of the modified gene product.

A suitable buffer will be one in which all of the desired components of the biological system are active and will therefore depend upon the requirements of each specific reaction system. Buffers suitable for biological and/or chemical reactions are known in the art and recipes provided in various laboratory texts, such as Sambrook et al., 1989.

The in vitro translation system will usually comprise a cell extract, typically from bacteria (Zubay, 1973; Zubay, 1980; Lesley et al., 1991; Lesley, 1995), rabbit reticulocytes (Pelham and Jackson, 1976), or wheat germ (Anderson et al., 1983). Many suitable systems are commercially available (for example from Promega) including some which will allow coupled transcription/translation (all the bacterial systems and the reticulocyte and wheat germ TNT™ extract systems from Promega). The mixture of amino acids used may include synthetic amino acids if desired, to increase the possible number or variety of proteins produced in the library. This can be accomplished by charging tRNAs with artificial amino acids and using these tRNAs for the in vitro translation of the proteins to be selected (Ellman et al., 1991; Benner, 1994; Mendel et al., 1995).

After each round of selection the enrichment of the pool of genetic elements for those encoding the molecules of interest can be assayed by non-compartmentalised in vitro transcription/replication or coupled transcription-translation reactions. The selected pool is cloned into a suitable plasmid vector and RNA or recombinant protein is produced from the individual clones for further purification and assay.

In a preferred aspect, the internal environment of a microcapsule may be altered by addition of reagents to the oil phase of the emulsion. The reagents diffuse through the oil phase to the aqueous microcapsule environment. Preferably, the reagents are at least partly water-soluble, such that a proportion thereof is distributed from the oil phase to the aqueous microcapsule environment. Advantageously, the reagents are substantially insoluble in the oil phase. Reagents are preferably mixed into the oil phase by mechanical mixing, for example vortexing.

The reagents which may be added via the oil phase include substrates, buffering components, factors and the like. In particular, the internal pH of microcapsules may be altered in situ by adding acidic or basic components to the oil phase.

The invention moreover relates to a method for producing a gene product, once a genetic element encoding the gene product has been sorted by the method of the invention. Clearly, the genetic element itself may be directly expressed by conventional means to produce the gene product. However, alternative techniques ma be employed, as will be apparent to those skilled in the art. For example, the genetic information incorporated in the gene product may be incorporated into a suitable expression vector, and expressed therefrom.

The invention also describes the use of conventional screening techniques to identify compounds which are capable of interacting with the gene products identified by the first aspect of the invention. In preferred embodiments, gene product encoding nucleic acid is incorporated into a vector, and introduced into suitable host cells to produce transformed cell lines that express the gene product. The resulting cell lines can then be produced for reproducible qualitative and/or quantitative analysis of the effect(s) of potential drugs affecting gene product function. Thus gene product expressing cells may be employed for the identification of compounds, particularly small molecular weight compounds, which modulate (i.e., increase or decrease by at least 10% relative to a sample without a test compound) the function of gene product. Thus host cells expressing gene product are useful for drug screening and it is a further object of the present invention to provide a method for identifying compounds which modulate the activity of the gene product, said method comprising exposing cells containing heterologous DNA encoding gene product, wherein said cells produce functional gene product, to at least one compound or mixture of compounds or signal whose ability to modulate the activity of said gene product is sought to be determined, and thereafter monitoring said cells for changes caused by said modulation. Such an assay enables the identification of modulators, such as agonists, antagonists and allosteric modulators, of the gene product. As used herein, a compound or signal that modulates the activity of gene product refers to a compound that alters the activity of gene product in such a way that the activity of the gene product is different in the presence of the compound or signal (as compared to the absence of said compound or signal).

Cell-based screening assays can be designed by constructing cell lines in which the expression of a reporter protein, i.e. an easily assayable protein, such as β-galactosidase, chloramphenicol acetyltransferase (CAT), green fluorescent protein (GFP) or luciferase, is dependent on gene product. Such an assay enables the detection of compounds that directly modulate gene product function, such as compounds that antagonise gene product, or compounds that inhibit or potentiate other cellular functions required for the activity of gene product.

The present invention also provides a method to exogenously affect gene product dependent processes occurring in cells. Recombinant gene product producing host cells, e.g. mammalian cells, can be contacted with a test compound, and the modulating effect(s) thereof can then be evaluated by comparing the gene product-mediated response in the presence and absence of test compound, or relating the gene product-mediated response of test cells, or control cells (i.e., cells that do not express gene product), to the presence of the compound.

In a further aspect, the invention relates to a method for optimising a production process which involves at least one step which is facilitated by a polypeptide. For example, the step may be a catalytic step, which is facilitated by an enzyme. Thus, the invention provides a method for preparing a compound or compounds comprising the steps of:

(a) providing a synthesis protocol wherein at least one step is facilitated by a polypeptide;

(b) preparing genetic elements encoding variants of the polypeptide which facilitates this step, the expression of which may result, directly or indirectly, in the modification of the optical properties of the genetic elements;

(c) compartmentalising genetic elements into microcapsules;

(d) expressing the genetic elements to produce their respective gene products within the microcapsules;

(e) sorting the genetic elements which produce polypeptide gene product(s) having the desired activity using the changed optical properties of the genetic elements; and (f) preparing the compound or compounds using the polypeptide gene product identified in (g) to facilitate the relevant step of the synthesis.

By means of the invention, enzymes involved in the preparation of a compound may be optimised by selection for optimal activity. The procedure involves the preparation of variants of the polypeptide to be screened, which equate to a library of polypeptides as referred to herein. The variants may be prepared in the same manner as the libraries discussed elsewhere herein.

(B) SELECTION PROCEDURES

The system can be configured to select for RNA, DNA or protein gene product molecules with catalytic, regulatory or binding activity.

(i) Selection for Binding

In the case of selection for a gene product with affinity for a specific ligand the genetic element may be linked to the gene product in the microcapsule via the ligand. Only gene products with affinity for the ligand will therefore bind to the genetic element and only those genetic elements with gene product bound via the ligand will acquire the changed optical properties which enable them to be retained in the selection step. In this embodiment, the genetic element will thus comprise a nucleic acid encoding the gene product linked to a ligand for the gene product.

The change in optical properties of the genetic element after binding of the gene product to the ligand may be induced in a variety of ways, including:

(1) the gene product itself may have distinctive optical properties, for example, it is fluorescent (e.g. green fluorescent protein, (Lorenz et al., 1991)).

(2) the optical properties of the gene product may be modified on binding to the ligand, for example, the fluorescence of the gene product is quenched or enhanced on binding (Guixe et al., 1998; Qi and Grabowski, 1998)

(3) the optical properties of the ligand may be modified on binding of the gene product, for example, the fluorescence of the ligand is quenched or enhanced on binding (Voss, 1993; Masui and Kuramitsu, 1998).

(4) the optical properties of both ligand and gene product are modified on binding, for example, there can be a fluorescence resonance energy transfer (FRET) from ligand to gene product (or vice versa) resulting in emmission at the "acceptor" emmission wavelength when excitation is at the "donor" absorption wavelength (Heim & Tsien, 1996; Mahajan et al., 1998; Miyawaki et al., 1997).

In this embodiment, it is not necessary for binding of the gene product to the genetic element via the ligand to directly induce a change in optical properties. All the gene products to be selected can contain a putative binding domain, which is to be selected for, and a common feature—a tag. The genetic element in each microcapsule is physically linked to the ligand. If the gene product produced from the genetic element has affinity for the ligand, it will bind to it and become physically linked to the same genetic element that encoded it, resulting in the genetic element being 'tagged'. At the end of the reaction, all of the microcapsules are combined, and all genetic elements and gene products pooled together in one environment. Genetic elements encoding gene products exhibiting the desired binding can be selected by adding reagents which specifically bind to, or react specifically with, the "tag" and thereby induce a change in the optical properties of the genetic element allowing there sorting. For example, a fluorescently-labelled anti-"tag" antibody can be used, or an anti-"tag" antibody followed by a second fluorescently labelled antibody which binds the first.

In an alternative embodiment, genetic elements may be sorted on the basis that the gene product, which binds to the ligand, merely hides the ligand from, for example, further binding partners which would otherwise modify the optical properties of the genetic element. In this case genetic elements with unmodified optical properties would be selected.

In an alternative embodiment, the invention provides a method according to the first aspect of the invention, wherein in step (b) the gene products bind to genetic elements encoding them. The gene products together with the attached genetic elements are then sorted as a result of binding of a ligand to gene products having the desired binding activity. For example, all gene products can contain an invariant region which binds covalently or non-covalently to the genetic element, and a second region which is diversified so as to generate the desired binding activity.

In an alternative embodiment, the ligand for the gene product is itself encoded by the genetic element and binds to the genetic element. Stated otherwise, the genetic element encodes two (or indeed more) gene products, at least one of which binds to the genetic element, and which can potentially bind each other. Only when the gene products interact in a microcapsule is the genetic element modified in a way that ultimately results in a change in a change in its optical properties that enables it to be sorted. This embodiment, for example, is used to search gene libraries for pairs of genes encoding pairs of proteins which bind each other.

Fluorescence may be enhanced by the use of Tyramide Signal Amplification (TSA™) amplification to make the genetic elements fluorescent. This involves peroxidase (linked to another protein) binding to the genetic elements and catalysing the conversion of fluorescein-tyramine in to a free radical form which then reacts (locally) with the genetic elements. Methods for performing TSA are known in the art, and kits are available commercially from NEN.

TSA may be configured such that it results in a direct increase in the fluorescence of the genetic element, or such that a ligand is attached to the genetic element which is bound by a second fluorescent molecule, or a sequence of molecules, one or more of which is fluorescent.

(ii) Selection for Catalysis

When selection is for catalysis, the genetic element in each microcapsule may comprise the substrate of the reaction. If the genetic element encodes a gene product capable of acting as a catalyst, the gene product will catalyse the conversion of the substrate into the product. Therefore, at the end of the reaction the genetic element is physically linked to the product of the catalysed reaction.

It may also be desirable, in some cases, for the substrate not to be a component of the genetic element. In this case the substrate would contain an inactive "tag" that requires a further step to activate it such as photoactivation (e.g. of a "caged" biotin analogue, (Sundberg et al., 1995; Pirrung and Huang, 1996)). The catalyst to be selected then converts the substrate to product. The "tag" is then activated and the "tagged" substrate and/or product bound by a tag-binding molecule (e.g. avidin or streptavidin) complexed with the nucleic acid. The ratio of substrate to product attached to the nucleic acid via the "tag" will therefore reflect the ratio of the substrate and product in solution.

The optical properties of genetic elements with product attached and which encode gene products with the desired catalytic activity can be modified by either:

(1) the product-genetic element complex having characteristic optical properties not found in the substrate-genetic element complex, due to, for example;
   (a) the substrate and product having different optical properties (many fluorogenic enzyme substrates are available commercially (see for example Haugland, 1996) including substrates for glycosidases, phosphatases, peptidases and proteases (Craig et al., 1995; Huang et al., 1992; Brynes et al., 1982; Jones et al., 1997; Matayoshi et al., 1990; Wang et al., 1990)), or
   (b) the substrate and product having similar optical properties (i.e., measurable parameters of one or more optical properties are within 5% of each other), but only the product, and not the substrate binds to, or reacts with, the genetic element;
(2) adding reagents which specifically bind to, or react with, the product and which thereby induce a change in the optical properties of the genetic elements allowing their sorting (these reagents can be added before or after breaking the microcapsules and pooling the genetic elements). The reagents;
   (a) bind specifically to, or react specifically with, the product, and not the substrate, if both substrate and product are attached to the genetic element, or
   (b) optionally bind both substrate and product if only the product, and not the substrate binds to, or reacts with, the genetic element.

The pooled genetic elements encoding catalytic molecules can then be enriched by selecting for the genetic elements with modified optical properties.

An alternative is to couple the nucleic acid to a product-specific antibody (or other product-specific molecule). In this scenario, the substrate (or one of the substrates) is present in each microcapsule unlinked to the genetic element, but has a molecular "tag" (for example biotin, DIG or DNP or a fluorescent group). When the catalyst to be selected converts the substrate to product, the product retains the "tag" and is then captured in the microcapsule by the product-specific antibody. In this way the genetic element only becomes associated with the "tag" when it encodes or produces an enzyme capable of converting substrate to product. When all reactions are stopped and the microcapsules are combined, the genetic elements encoding active enzymes will be "tagged" and may already have changed optical properties, for example, if the "tag" was a fluorescent group. Alternatively, a change in optical properties of "tagged" genes can be induced by adding a fluorescently labelled ligand which binds the "tag" (for example fluorescently-labelled avidin/streptavidin, an anti-"tag" antibody which is fluorescent, or a non-fluorescent anti-"tag" antibody which can be detected by a second fluorescently-labelled antibody).

Alternatively, selection may be performed indirectly by coupling a first reaction to subsequent reactions that takes place in the same microcapsule. There are two general ways in which this may be performed. In a first embodiment, the product of the first reaction is reacted with, or bound by, a molecule which does not react with the substrate of the first reaction. A second, coupled reaction will only proceed in the presence of the product of the first reaction. A genetic element encoding a gene product with a desired activity can then be purified by using the properties of the product of the second reaction to induce a change in the optical properties of the genetic element as above.

Alternatively, the product of the reaction being selected may be the substrate or cofactor for a second enzyme-catalysed reaction. The enzyme to catalyse the second reaction can either be translated in situ in the microcapsules or incorporated in the reaction mixture prior to microencapsulation. Only when the first reaction proceeds will the coupled enzyme generate a product which can be used to induce a change in the optical properties of the genetic element as above.

This concept of coupling can be elaborated to incorporate multiple enzymes, each using as a substrate the product of the previous reaction. This allows for selection of enzymes that will not react with an immobilised substrate. It can also be designed to give increased sensitivity by signal amplification if a product of one reaction is a catalyst or a cofactor for a second reaction or series of reactions leading to a selectable product (for example, see Johannsson and Bates, 1988; Johannsson, 1991). Furthermore an enzyme cascade system can be based on the production of an activator for an enzyme or the destruction of an enzyme inhibitor (see Mize et al., 1989). Coupling also has the advantage that a common selection system can be used for a whole group of enzymes which generate the same product and allows for the selection of complicated chemical transformations that cannot be performed in a single step.

Such a method of coupling thus enables the evolution of novel "metabolic pathways" in vitro in a stepwise fashion, selecting and improving first one step and then the next. The selection strategy is based on the final product of the pathway, so that all earlier steps can be evolved independently or sequentially without setting up a new selection system for each step of the reaction.

Expressed in an alternative manner, there is provided a method of isolating one or more genetic elements encoding a gene product having a desired catalytic activity, comprising the steps of:

(1) expressing genetic elements to give their respective gene products;
(2) allowing the gene products to catalyse conversion of a substrate to a product, which may or may not be directly selectable, in accordance with the desired activity;
(3) optionally coupling the first reaction to one or more subsequent reactions, each reaction being modulated by the product of the previous reactions, and leading to the creation of a final, selectable product;
(4) linking the selectable product of catalysis to the genetic elements by either:
   a) coupling a substrate to the genetic elements in such a way that the product remains associated with the genetic elements, or
   b) reacting or binding the selectable product to the genetic elements by way of a suitable molecular "tag" attached to the substrate which remains on the product, or
   c) coupling the selectable product (but not the substrate) to the genetic elements by means of a product-specific reaction or interaction with the product; and
(5) selecting the product of catalysis, together with the genetic element to which it is bound, either by means of its characteristic optical properties, or by adding reagents which specifically bind to, or react specifically with, the product and which thereby induce a change in the optical properties of the genetic elements wherein steps (1) to (4) each genetic element and respective gene product is contained within a microcapsule.

(iii) Selecting for Enzyme Substrate Specificity/Selectivity

Genetic elements encoding enzymes with substrate specificity or selectivity can be specifically enriched by carrying out a positive selection for reaction with one substrate and a negative selection for reaction with another substrate. Such combined positive and negative selection pressure can improve (i.e., increase by at least 10%) the specificity or selectivity of the enzyme for a given substrate, and should be of great importance in isolating regio-selective and stereo-selective enzymes (for example, enzymes that can distinguish between two enantiomers of the same substrate). For example, two substrates (e.g. two different enantiomers) are each labelled with different tags (e.g. two different fluorophores) such that the tags become attached to the genetic element by the enzyme-catalysed reaction. If the two tags confer different optical properties on the genetic element the substrate specificity of the enzyme can be determined from the optical properties of the genetic element and those genetic elements encoding gene products with the wrong (or no) specificity rejected. Tags conferring no change in optical activity can also be used if tag-specific ligands with different optical properties are added (e.g. tag-specific antibodies labelled with different fluorophores).

(iv) Selection for Regulation

A similar system can be used to select for regulatory properties of enzymes.

In the case of selection for a regulator molecule which acts as an activator or inhibitor of a biochemical process, the components of the biochemical process can either be translated in situ in each microcapsule or can be incorporated in the reaction mixture prior to microencapsulation. If the genetic element being selected is to encode an activator, selection can be performed for the product of the regulated reaction, as described above in connection with catalysis. If an inhibitor is desired, selection can be for a chemical property specific to the substrate of the regulated reaction.

There is therefore provided a method of sorting one or more genetic elements coding for a gene product exhibiting a desired regulatory activity, comprising the steps of:

(1) expressing genetic elements to give their respective gene products;
(2) allowing the gene products to activate or inhibit a biochemical reaction, or sequence of coupled reactions, in accordance with the desired activity, in such a way as to allow the generation or survival of a selectable molecule;
(3) linking the selectable molecule to the genetic elements either by
   a) having the selectable molecule, or the substrate from which it derives, attached to the genetic elements, or
   b) reacting or binding the selectable product to the genetic elements, by way of a suitable molecular "tag" attached to the substrate which remains on the product, or
   c) coupling the product of catalysis (but not the substrate) to the genetic elements, by means of a product-specific reaction or interaction with the product;
(4) selecting the selectable product, together with the genetic element to which it is bound, either by means of its characteristic optical properties, or by adding reagents which specifically bind to, or react specifically with, the product and which thereby induce a change in the optical properties of the genetic elements wherein steps (1) to (3) each genetic element and respective gene product is contained within a microcapsule.

(v) Selection for Optical Properties of the Gene Product

It is possible to select for inherent optical properties of gene products if, in the microcapsules, the gene product binds back to the genetic element, for example through a common element of the gene product which binds to a ligand which is part of the genetic element. After pooling the genetic elements they can then be sorted using the optical properties of the bound gene products. This embodiment can be used, for example, to select variants of green fluorescent protein (GFP) (Cormack et al., 1996; Delagrave et al., 1995; Ehrig et al., 1995), with improved fluorescence and/or novel absorption and emmission spectra.

(vi) Flow Sorting of Genetic Elements

In a preferred embodiment of the invention the genetic elements will be sorted by flow cytometry. A variety of optical properties can be used to trigger sorting, including light scattering (Kerker, 1983) and fluorescence polarisation (Rolland et al., 1985). In a highly preferred embodiment the difference in optical properties of the genetic elements will be a difference in fluorescence and the genetic elements will be sorted using a fluorescence activated cell sorter (Norman, 1980; Mackenzie and Pinder, 1986), or similar device. In an especially preferred embodiment the genetic element comprises of a nonfluorescent nonmagnetic (e.g. polystyrene) or paramagnetic microbead (see Fornusek and Vetvicka, 1986), optimally 0.6 to 1.0 µm diameter, to which are attached both the gene and the groups involved in generating a fluorescent signal:

(1) commercially available fluorescence activated cell sorting equipment from established manufacturers (e.g. Becton-Dickinson, Coulter) allows the sorting of up to $10^8$ genetic elements (events) per hour;

(2) the fluorescence signal from each bead corresponds tightly to the number of fluorescent molecules attached to the bead. At present as little as few hundred fluorescent molecules per particle can be quantitatively detected;

(3) the wide dynamic range of the fluorescence detectors (typically 4 log units) allows easy setting of the stringency of the sorting procedure, thus allowing the recovery of the optimal number of genetic elements from the starting pool (the gates can be set to separate beads with small differences in fluorescence or to only separate out beads with large differences in fluorescence, dependant on the selection being performed;

(4) commercially available fluorescence-activated cell sorting equipment can perform simultaneous excitation at up to two different wavelengths and detect fluorescence at up to four different wavelengths (Shapiro, 1983) allowing positive and negative selections to be performed simultaneously by monitoring the labelling of the genetic element with two (or more) different fluorescent markers, for example, if two alternative substrates for an enzyme (e.g. two different enantiomers) are labelled with different fluorescent tags the genetic element can labelled with different fluorophores dependent on the substrate used and only genes encoding enzymes with enantioselectivity selected.

(5) highly uniform derivatised and non-derivatised non-magnetic and paramagnetic microparticles (beads) are commercially available from many sources (e.g. Sigma, and Molecular Probes) (Fornusek and Vetvicka, 1986).

(vii) Multi-Step Procedure

It will be also be appreciated that according to the present invention, it is not necessary for all the processes of transcription/replication and/or translation, and selection to proceed in one single step, with all reactions taking place in one microcapsule. The selection procedure may comprise two or more steps. First, transcription/replication and/or translation of each genetic element of a genetic element library may take place in a first microcapsule. Each gene product is then linked to the genetic element which encoded it (which resides in the same microcapsule), for example via a gene product-specific ligand such as an antibody. The microcapsules are then broken, and the genetic elements attached to their respective gene products optionally purified. Alternatively, genetic elements can be attached to their respective gene products using methods which do not rely on encapsulation. For example phage display (Smith, G. P., 1985), polysome display (Mattheakkis et al., 1994), RNA-peptide fusion (Roberts and Szostak, 1997) or lac repressor peptide fusion (Cull, et al., 1992).

In the second step of the procedure, each purified genetic element attached to its gene product is put into a second microcapsule containing components of the reaction to be selected. This reaction is then initiated. After completion of the reactions, the microcapsules are again broken and the modified genetic elements are selected. In the case of complicated multistep reactions in which many individual components and reaction steps are involved, one or more intervening steps may be performed between the initial step of creation and linking of gene product to genetic element, and the final step of generating the selectable change in the genetic element.

If necessary, release of the gene product from the genetic element within a secondary microcapsule can be achieved in a variety of ways, including by specific competition by a low-molecular weight product for the binding site or cleavage of a linker region joining the binding domain of the gene product from the catalytic domain either enzymatically (using specific proteases) or autocatalytically (using an integrin domain).

(viii) Selection by Activation of Reporter Gene Expression In Situ

The system can be configured such that the desired binding, catalytic or regulatory activity encoded by a genetic element leads, directly or indirectly to the activation of expression of a "reporter gene" that is present in all microcapsules. Only gene products with the desired activity activate expression of the reporter gene. The activity resulting from reporter gene expression allows the selection of the genetic element (or of the compartment containing it) by any of the methods described herein.

For example, activation of the reporter gene may be the result of a binding activity of the gene product in a manner analogous to the "two hybrid system" (Fields and Song, 1989). Activation can also result from the product of a reaction catalysed by a desirable gene product. For example, the reaction product can be a transcriptional inducer of the reporter gene. For example arabinose may be used to induce transcription from the araBAD promoter. The activity of the desirable gene product can also result in the modification of a transcription factor, resulting in expression of the reporter gene. For example, if the desired gene product is a kinase or phosphatase the phosphorylation or dephosphorylation of a transcription factor may lead to activation of reporter gene expression.

(ix) Amplification

According to a further aspect of the present invention the method comprises the further step of amplifying the genetic elements. Selective amplification may be used as a means to enrich for genetic elements encoding the desired gene product.

In all the above configurations, genetic material comprised in the genetic elements may be amplified and the process repeated in iterative steps. Amplification may be by the polymerase chain reaction (Saiki et al., 1988) or by using one of a variety of other gene amplification techniques including; Qb replicase amplification (Cahill, Foster and Mahan, 1991; Chetverin and Spirin, 1995; Katanaev, Kurnasov and Spirin, 1995); the ligase chain reaction (LCR) (Landegren et al., 1988; Barany, 1991); the self-sustained sequence replication system (Fahy, Kwoh and Gingeras, 1991) and strand displacement amplification (Walker et al., 1992).

Various aspects and embodiments of the present invention are illustrated in the following examples. It will be appreciated that modification of detail may be made without departing from the scope of the invention.

All documents mentioned in the text are incorporated by reference.

EXAMPLES

Example 1

Enzymes can be Expressed from Genes in Solution and Genes Attached to Paramagnetic Microbeads with Identical Efficiency

One format for the selection of genetic elements by using a change in their optical properties is one in which the genetic element comprises a microbead to which the gene is attached. Here it is shown how a gene for an enzyme (*E. coli* dihydrofolate reductase) can be linked to a paramagnetic bead and is translated in vitro just as efficiently as in solution.

The *E. coli* folA gene encoding dihydrofolate reductase (DHFR) is PCR-amplified using oligonucleotides EDHFRFo and EDHFRBa. This DNA is then cloned into the pGEM-4Z vector (Promega) digested with HindIII and KpnI downstream of the lac promoter and the T7 RNA polymerase promoter. The oligonucleotide EDHFRBa appends the efficient phage T7 gene 10 translational start site upstream of the DHFR start codon.

DNA sequencing identifies a clone which has the correct nucleotide sequence. Bacteria transformed with this clone (pGEM-folA) are found to over-express active DHFR (driven from the lac promoter) when induced with IPTG.

The folA gene in pQEM-folA plasmid is then PCR-amplified using primers folA-FW and folA-BW, the resulting DNA fragment in HindIII and XhoI digested and subcloned into HindIII/XhoI-digested pET23a expression vector (Novagen) to give construct pET23a/folA. The sequence of PCR-amplified folA gene was verified by sequencing.

pET23a/folA was further amplified with 5'-biotinylated primers pETfor.b and pETrev.b and radio-labelled by including 10 µCi $\alpha^{35}$S-dATP (Amersham Pharmacia Biotech, U.K.) in the PCR mix. The resulting 1765 bp double biotinylated fragment T7-folA was gel purified using a Qiagen kit and quantified spectrophotometrically. The specific activity of the product was 210000 CPM/pmol T7-folA DNA, as measured on the Beckman LS6000SC scintillation counter. 10-nM and 1 nM dilutions of this DNA were made in 1 mg/ml HindIII digested lambda DNA to eliminate non-specific binding to the plastic). This PCR fragment was used thereafter to program a prokaryotic in vitro coupled transcription/translation system designed for linear templates, (Lesley, Brow and Burgess, 1991). A commercial preparation of this system is used (*E. coli* S30 Extract System for Linear Templates; Promega) supplemented with T7 RNA polymerase ($10^3$ units).

The DNA fragment is bound to streptavidin-paramagnetic beads (0.74 µm diameter Sera-Mag beads, biotin-binding capacity 46 mmol/mg, Seradyn, USA), partially precoated with biotinylated protein A. (Sigma). 2 µl of 80 µM biotinylated protein A is added to 100 µl (1 mg) beads, allowed to bind at room temperature for 1 hour, washed once and coated for one hour at room temperature with rabbit IgG (10 µl 1 mg/ml antibody per 1 mg beads in TBS/0.1% Tween-20 (TBST)). Beads were thereafter washed twice with TBS/T before radiolabeled biotinylated T7-folA DNA was added and allowed to bind for 1 hour at room temperature. The amount of bound T7-folA DNA was calculated by counting the radioactivity bound to an aliquot of beads. ~50% of the total DNA was bound.

DNA fragments bound on beads or unbound DNA fragment are added directly to the S30 Extract System. Reactions are incubated for 2 hours at 37° C.

Dihydrofolate reductase activity is assayed by spectrophotometrically monitoring the oxidation of NADPH to NADP at 340 nm over a 10 minute time course as described by (Williams et al., 1979; Ma et al., 1993). 2 µl of each quenched in vitro translation reaction is added to 150 µl Buffer A (100 mM Imidazole, pH 7.0, 10 mM β-mercaptoethanol) and 20 µl 1 mM NADPH. 20 µl dihydrofolate (1 mM)(H$_2$F) is added after 1 minute and the reaction monitored at 340 nm using a ThermoMax microplate reader (Molecular Devices). Activity is calculated by initial velocities under So>>K$_M$ conditions (υmax).

Figure 1:
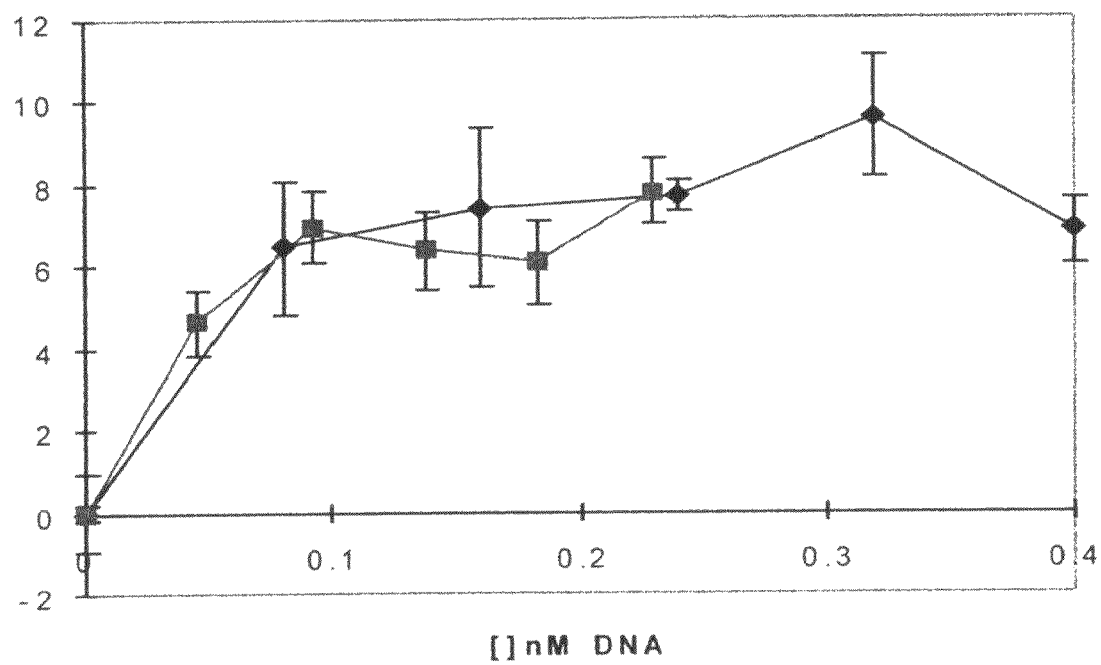
FIG. 1. Dihydrofolate reductase can be expressed from genes in vitro translated in solution and genes attached to paramagnetic beads with identical efficiency. The DHFR activity resulting from in vitro translation of folA genes in solution or folA genes attached to paramagnetic microbeads is determined by monitoring the oxidation of NADPH to NADP spectrophotometrically at 340 nm and activity is calculated by initial velocities under $S_o \gg K_M$ conditions (υmax). (♦), translated from genes in solution; (■), translated from genes attached to microbeads. 2.

There is no significant difference in the amount of active DHFR produced if the DNA is free, or attached via terminal biotins to a streptavidin coated bead (see FIG. 1).

Example 2

A Fluorescent Protein (GFP) can be Translated In Vitro from Genes Attached to Single Microbeads Encapsulated in the Aqueous Compartments of a Water-in-Oil Emulsion and the Translated Gene-Product Bound Back to the Microbeads Making them Fluorescent

One format for the selection of genetic elements is where the genetic element comprises a gene linked to a microbead and the product is coupled back onto the microbead within the microcapsule resulting directly, or indirectly, in a change in the optical properties of the microbead which allows it to be sorted.

Here it is shown that a fluorescent protein (green fluorescent protein or GFP) can be transcribed and translated in vitro from genes attached to single microbeads encapsulated in the aqueous compartments of a water-in-oil emulsion and the translated gene-product bound back the microbeads making them fluorescent.

The GFP in pBS/GFP6 plasmid (Siemering et al., 1996) was PCR-amplified using primers GFP-FW and GFP-BW, the resulting DNA fragment in HindIII and XhoI digested and subcloned into HindIII/XhoI-digested pET23a expression vector (Novagen) to give construct pET23a/GFP. The sequence of PCR-amplified GFP gene was verified by sequencing. pET23a/GFP was further amplified with 5'-biotinylated primers pETfor.b and pETrev.b. The resulting 2038 bp double biotinylated fragment T7-GFP was gel purified using a Qiagen kit and quantified spectrophotometrically. 10 nM and 1 nM dilutions of this DNA were made in 1 mg/ml HindIII digested lambda DNA to eliminate non-specific binding to the plastic). This PCR fragment was used thereafter to program a prokaryotic in vitro coupled transcription/translation system designed for linear templates (Lesley, Brow and Burgess, 1991). A commercial preparation of this system is used (E. coli S30 Extract System for Linear Templates; Promega) supplemented with T7 RNA polymerase ($10^3$ units).

As a control, a biotinylated 1765 bp DNA fragment T7-folA (synthesised by PCR as in example 1) was used to program the synthesis of the non-fluorescent protein DHFR.

150 µl ProActive streptavidin-coated paramagnetic beads (Bangs Laboratories, $2 \times 10^7$ beads/µl) were suspended in 5 mM Tris 7.4/1M NaCl/0.1% Tween20 and split into three aliquots of 50 µl. 0.5 µl of 0.2 µM DNA (T7-folA or T7-GFP) was added to each aliquot of beads, incubated at 43° C. for 15 min, washed three times in 25 mM $NaH_2PO_4$, 125 mM NaCl, 0.1% Tween20, pH 7.0 (PBS/0.1% Tween20), resuspended in 40 µl TBST and 10 µl 80 µM biotinylated protein A (Sigma) was added (to give final concentration of 15 µM). After incubation for 30 minutes at room temperature, the beads were washed three times in PBS/0.1% Tween20 and resuspended in 20 µl 1:10 dilution rabbit anti-GFP polyclonal antibody (Clontech) or 1 mg/ml unimmunised rabbit IgG (Sigma). After incubation for 30 minutes at room temperature, the beads were washed three times in PBS/0.1% Tween0 and resuspended in 15 µl of S30 premix from an E. coli S30 Extract System for Linear Templates (Promega), sonicated for one minute in a sonication bath, then the rest of the S30 in vitro translation mixture was added (on ice) and supplemented with T7 RNA polymerase ($10^3$ units).

The 50 µl ice-cooled in vitro translation reactions were added gradually (in 5 aliquots of 10 µl over ~2 minutes) to 0.95 ml of ice-cooled oil-phase (freshly prepared by dissolving 4.5% (v/v) Span 80 (Fluka) in mineral oil (Sigma, #M-5904) followed by 0.5% (v/v) Tween 80 (SigmaUltra; #P-8074) in a 5 ml Costar Biofreeze Vial (#2051)) whilst stirring with a magnetic bar (8×3 mm with a pivot ring; Scientific Industries International, Loughborough, UK). Stirring (at 1150 rpm) was continued for an additional 3 minutes on ice. Reactions were then incubated 3 h at 32° C.

2 µl of emulsion were spread on a microscope slide beneath a 13 mm round cover slip and visualised using a 20× Neofluar objective on an Axioplan microscope (Zeiss) equipped with an RTEA CCD-1300-Y CCD camera (Princeton Instruments). Standard excitation and emission filters for fluorescein were used and images were processed with IPLab software.

Figure 2:
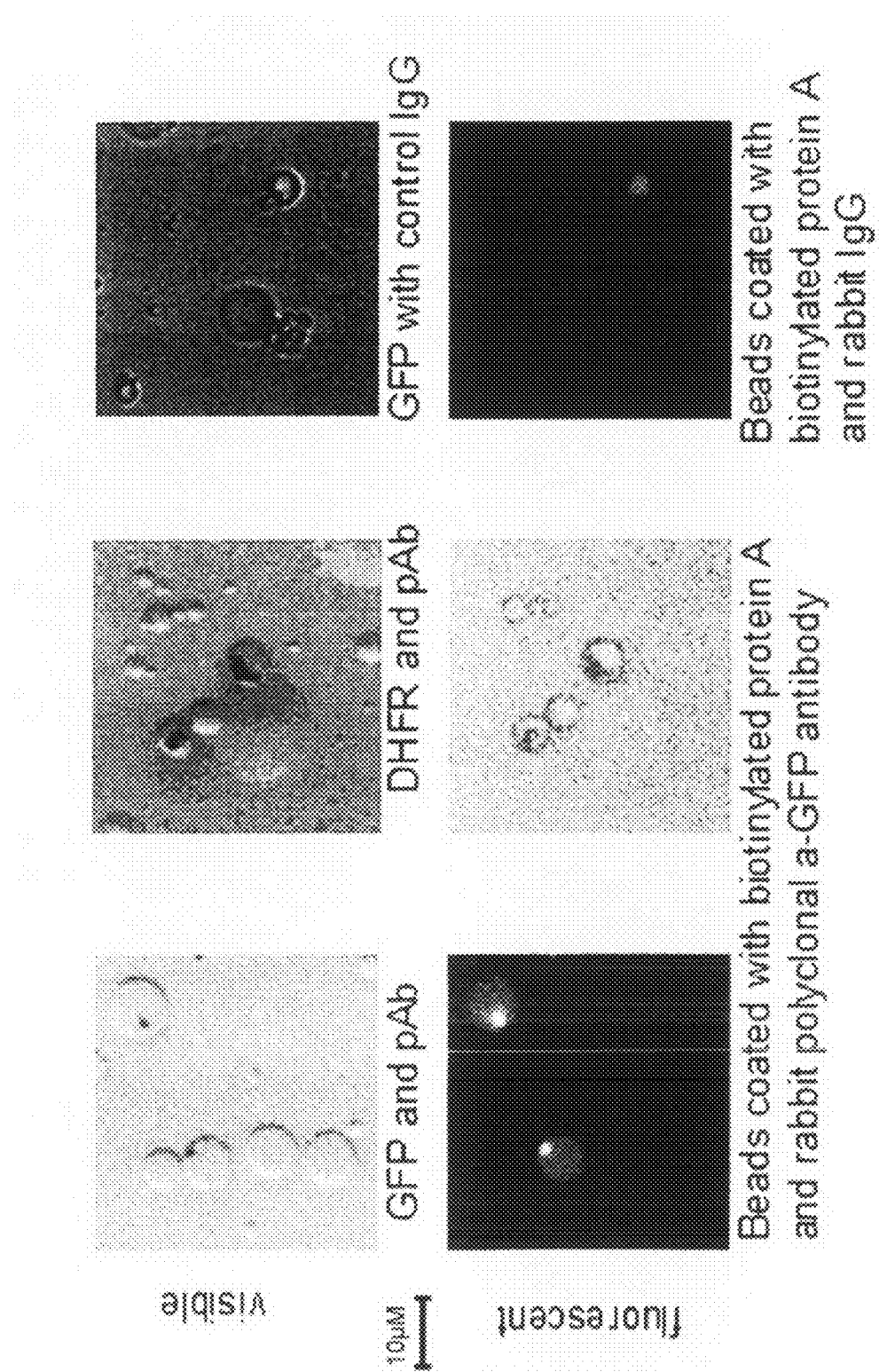
FIG. 2. Epifluorescence microscopy of water-in-oil emulsions demonstrating that GFP can be translated in vitro from genes attached to single microbeads encapsulated in the aqueous compartments of the emulsions and the translated gene-product bound back the microbeads making them fluorescent.

As can be seen from FIG. 2 the GFP translated from genes attached to single microbeads encapsulated in the aqueous compartments of the emulsions is bound to the microbeads in situ when the microbeads are coated with an anti-GFP antibody. This binding is observed as concentration of fluorescence on the beads by epifluorescence microscopy. No bead fluorescence is observed when either the GFP gene or the anti-GFP antibody are missing.

Example 3

A fluorescent protein (GFP) can be translated in vitro from genes attached to single microbeads encapsulated in the aqueous compartments of a water-in-oil emulsion, the translated gene-product bound back the microbeads and the increased fluorescence of the microbeads detected by flow cytometry.

Figure 3:
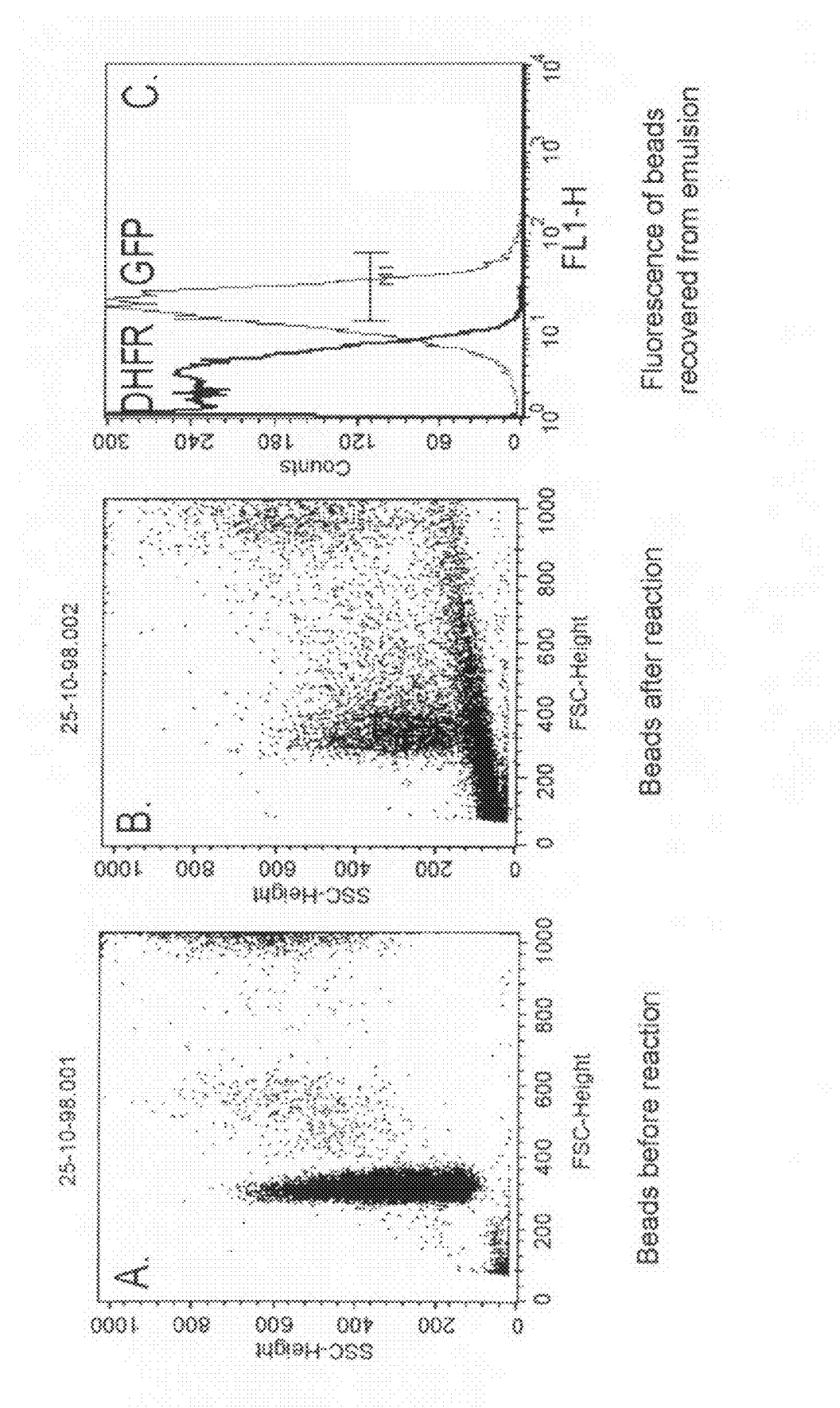
FIG. 3. Flow cytometric analysis of GFP expression in microcapsules and in situ binding to the genetic element (microbeads). A: The light scattering characteristics of the beads before reaction. 75% of beads run as single beads. B: The light scattering characteristics of the beads after in vitro translation reaction. About 50% of beads fall into the gate for single beads. C: Fluorescence from microbeads (gated for single beads only) coated with T7-GFP gene and anti-GFP polyclonal antibody is significantly higher than the signal from the beads where either the GFP gene or the anti-GFP antibody were omitted.

150 µl streptavidin-coated polystyrene beads (diameter 1 µM; Bangs Laboratories, $2 \times 10^7$ beads/µl) were suspended in 5 mM Tris 7.4/1M NaCl/0.1% Tween20 and split into three aliquots of 50 µl. 0.5 µl of 0.2 µM DNA (T7-folA or T7-GFP) was added to each aliquot of beads, incubated at 43° C. for 15 min, washed three times in 25 mM $NaH_2PO_4$, 125 mM NaCl, 0.1% Tween20, pH 7.0 (PBS/0.1% Tween20), resuspended in 40 µl TBST and 10 µl 80 µM biotinylated protein A (Sigma) was added (to give final concentration of 15 µM). After incubation for 30 minutes at room temperature, the beads were washed three times in PBS/0.1% Tween20 and resuspended in 20 µl 1:10 dilution rabbit anti-GFP polyclonal antibody (Clontech) or 1 mg/ml unimmunised rabbit IgG (Sigma). After incubation for 30 minutes at room temperature, the beads were washed three times in PBS/0.1% Tween20 and resuspended in 15 µl of S30 premix from an E. coli S30 Extract System for Linear Templates (Promega), sonicated for one minute in a sonication bath, then the rest of the S30 in vitro translation mixture was added (on ice) and supplemented with T7 RNA polymerase ($10^3$ units). The 50 µl ice-cooled in vitro translation reactions were added gradually (in 5 aliquots of 10 µl over ~2 minutes) to 0.95 ml of ice-cooled oil-phase (freshly prepared by dissolving 4.5% (v/v) Span 80 (Fluka) in mineral oil (Sigma, #M-5904) followed by 0.5% (v/v) Tween 80 (SigmaUltra; #P-8074) in a 5 ml Costar Biofreeze Vial (#2051)) whilst stirring with a magnetic bar (8×3 mm with a pivot ring; Scientific Industries International, Loughborough, UK). Stirring (at 1150 rpm) was continued for an additional 3 minutes on ice. Reactions were then incubated 3 h at 32° C. To recover the reaction mixtures, the emulsions were spun at 3,000 g for 5 minutes and the oil phase removed leaving the concentrated (but still intact) emulsion at the bottom of the vial. PBS and 2 ml of water-saturated ether were added and the mixture was vortexed, centrifuged briefly, and the ether phase removed. Beads were washed twice with PBS and finally resuspended at $10^8$ beads/ml in PBS. $10^4$ beads were analysed using a FACScalibur flow cytometer (Becton Dickinson) using excitation at 488 nm and the fluorescein emission filter. The GFP translated from genes attached to single microbeads encapsulated in the aqueous compartments of the emulsions is bound to the microbeads in situ when the microbeads are coated with an anti-GFP antibody. The binding of GFP to the microbeads makes them fluorescent (FIG. 2), and those beads with GFP bound can be clearly distinguished from those which do not by flow cytometry (FIG. 3).

Example 4

Figure 4:
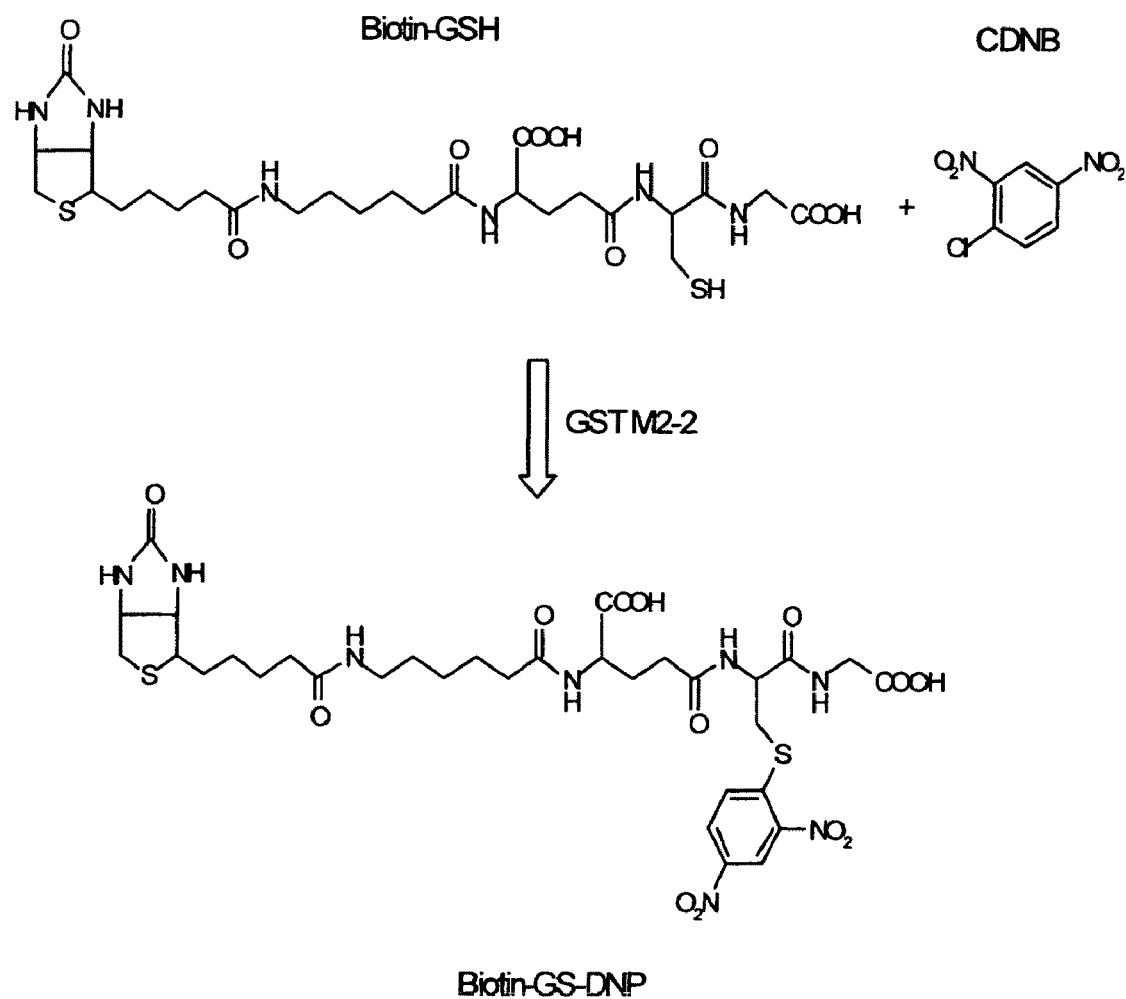
FIG. 4. Synthesis of Biotin-GS-DNP by the human glutathione S-transferase M2-2 (GST M2-2) catalysed reaction of 1-chloro-2,4-dinitrobenzene (CDNB; Sigma) with reduced biotinylated-glutathione (Biotin-GSH).

The Product of an Enzyme Catalysed Reaction can be Captured on Paramagnetic Beads and Beads Derivatised with Product Identified by Flow Cytometry A reaction catalysed by the enzyme human glutathione S-transferase M2-2 (GST M2-2) was performed to generate a biotinylated product (FIG. 4). The two substrates used were 1-chloro-2,4-dinitrobenzene (CDNB; Sigma) and reduced biotinylated-glutathione (Biotin-GSH). The product generated (Biotin-GS-DNP) has biotin at one end to enable coupling to streptavidin-coated paramagnetic microparticles and a 2,4-dinitrophenol (DNP) group which can be bound by an anti-DNP antibody.

Figure 5:
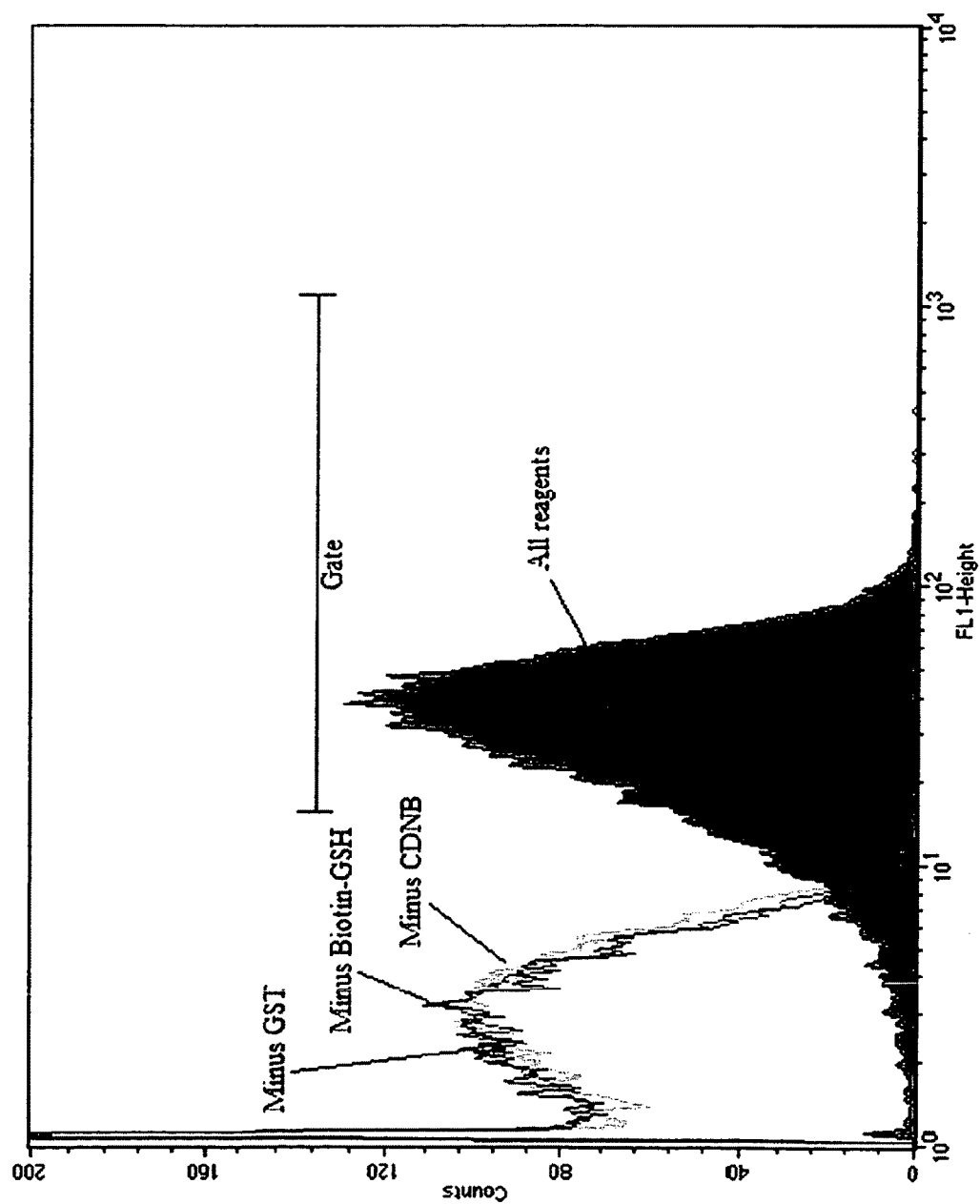
FIG. 5. Detecting paramagnetic beads coated with the product of an enzyme catalysed reaction by flow cytometry. Sera-Mag™ streptavidin-coated magnetic microparticles incubated with Biotin-GS-DNP made by the GST M2-2 catalysed reaction of Biotin-GSH and CDNB. The captured Biotin-GS-DNP was detected by incubation of the microparticles with a mouse anti-dinitrophenol antibody followed by a (FITC)-conjugated F(ab')$_2$ fragment goat anti-mouse IgG, F(ab')$_2$ fragment. After washing, $2 \times 10^5$ microparticles were analysed by flow cytometry. All reagents, no reagents omitted from the enzymatic synthesis of with Biotin-GS-DNP; minus GST, the enzyme GST M2-2 was omitted from the synthesis; minus biotin-GSH, biotin-GSH was omitted from the synthesis; minus CDNB, CDNB was omitted from the synthesis.

Biotin-GSH was synthesised by adding 100 mg biotinamidocaproate N-hydroxysuccinimide ester (biotin-NHS; Sigma) in 1 ml DMF to a solution of oxidised glutathione (Fluka) in 1 ml water, 30 µl 12.5N NaOH plus 1 ml DMF. The biotin-NHS was added, on ice, in 100 µl aliquots over 20 minutes. The pH was then adjusted to 7.0 with 1N NaOH. The syrup-like precipitate which formed during the reaction was dissolved by warming to room temperature, vortexing and adding 300 µl water. Stirring was continued for 2 hours at room temperature, the pH brought back to 7.0 by adding 1N NaOH and stirred overnight at room temperature. NaOH was then used to bring the pH back to 7.5, the reaction stirred a further 30 minutes at room temperature and then incubated 30 minutes more after adding 500 µl 1M DTT. The solvents were evaporated under vacuum and the product purified by reverse-phase HPLC using a C8 column and a gradient of 10-40% Acetonitrile, 0.1% TFA. Biotin-GS-DNP was synthesised enzymatically in a 100 µl reaction containing 1 µg purified recombinant GST M2-2, 500 µM CDNB and 200 µM Biotin-GSH in 0.1 M $KH_2PO_4$, 1 mM EDTA, pH6.5. Incubation was for 1 hour at 25° C. The reaction went essentially to completion as judged by following the increase in absorbance at 340 nm. Control reactions were also performed 1) with no GST, 2) with no CDNB % and 3) with no biotin-GSH. Reactions were diluted 200 times (giving a final concentration of 1 µM biotin) into 5 mM Tris-HCl, 0.5 mM EDTA, 1.0 M NaCl, pH7.4 (B/W buffer). 50 µl of the diluted reactions were mixed with 50 µl B/W buffer containing 29.3 µg ($10^8$ microparticles) 0.737 µm diameter Sera-Mag™ streptavidin-coated magnetic microparticles (MG-SA; Seradyn) and incubated 1 hour at room temperature. Microparticles were separated in a microtitre plate (Falcon 3911) using a magnet (Dynal MPC-96) and washed three times with 10 mM Tris-HCl, 1 mM EDTA, 2.0 M NaCl, pH7.4 (2× B/W buffer), then twice with PBS, 0.1% Tween 20. The microparticles were resuspended in a 1:2500 dilution of the mouse anti-dinitrophenol monoclonal antibody SPE 21-11 (a gift from Prof. Zelig Eshhar) in PBS/0.1% Tween 20 and incubated 45 minutes at room temperature. The microparticles were washed three times in PBS/0.1% Tween 20, resuspended in PBS/0.1% Tween 20 containing 15 µg/ml fluorescein (FITC)-conjugated F(ab')$_2$ fragment goat anti-mouse IgG, F(ab')2 fragment (Jackson; 115-096-006) and incubated 30 minutes at room temperature. The microparticles were washed four times in PBS/0.1% Tween 20, resuspended 1 ml PBS/0.1% Tween 20 and 2×$10^5$ microparticles analysed using a FACScan flow cytometer (Becton Dickinson). As can be seen from FIG. 5, there is no difference in the distribution of fluorescence intensity of beads from all three control reactions (no GST, no CDNB, and no biotin-GSH), where mean fluorescence is ~3. In contrast beads from the enzyme catalysed reaction have a mean fluorescence of 34, over 10 times higher. Indeed, using the gate shown (FIG. 5), 81.1% of beads from the enzyme catalysed reaction (and coated with the biotinylated product) are in the gate whereas in the control reactions no more than 0.06% of beads are in the gate. Hence, beads coated with the product of the GST catalysed reaction can easily be sorted from those which are not.

Example 5

Glutathione S-Transferase M2-2 (GST M2-2) will Use as a Substrate Caged-Biotinylated-Glutathione and the Caged-Biotinylated Product Generated can Subsequently be Uncaged by UV Irradiation Captured on Avidin-Coated Beads and Detected by Flow Cytometry The synthesis of caged-biotin (5) and its derivatives (7) was based on the published protocols (Pirrung & Huang, 1996; Sundberg et al. (1995). However, significant modifications of these protocols were made in several steps of the synthesis as described below.

Figure 6:
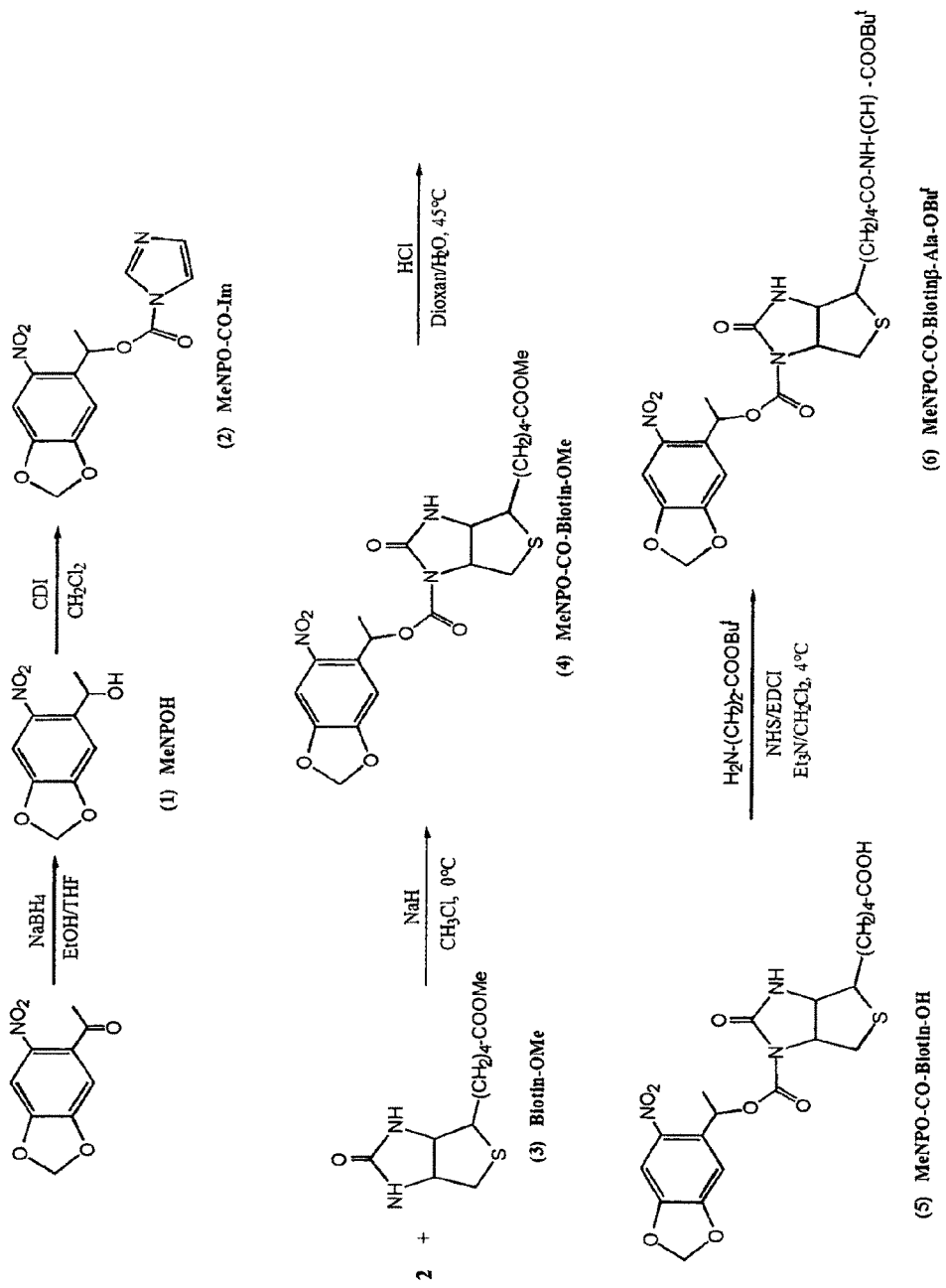
FIG. 6. Synthesis of MeNPO-CO-Biotin-β-Ala-GSH (caged-biotin-βala-GSH). Acetyl chloride (5 ml) was added to anhydrous methanol (80 ml). The stirred solution was allowed to cool down and d-biotin (4 g) was added. After over-night stirring the solvents were evaporated in vacuum to afford a white solid. The solid was triturated with ether, filtered and dried under vacuum (in the presence of phosphorus pentoxide) and stored at −20° C.
Figure 6:
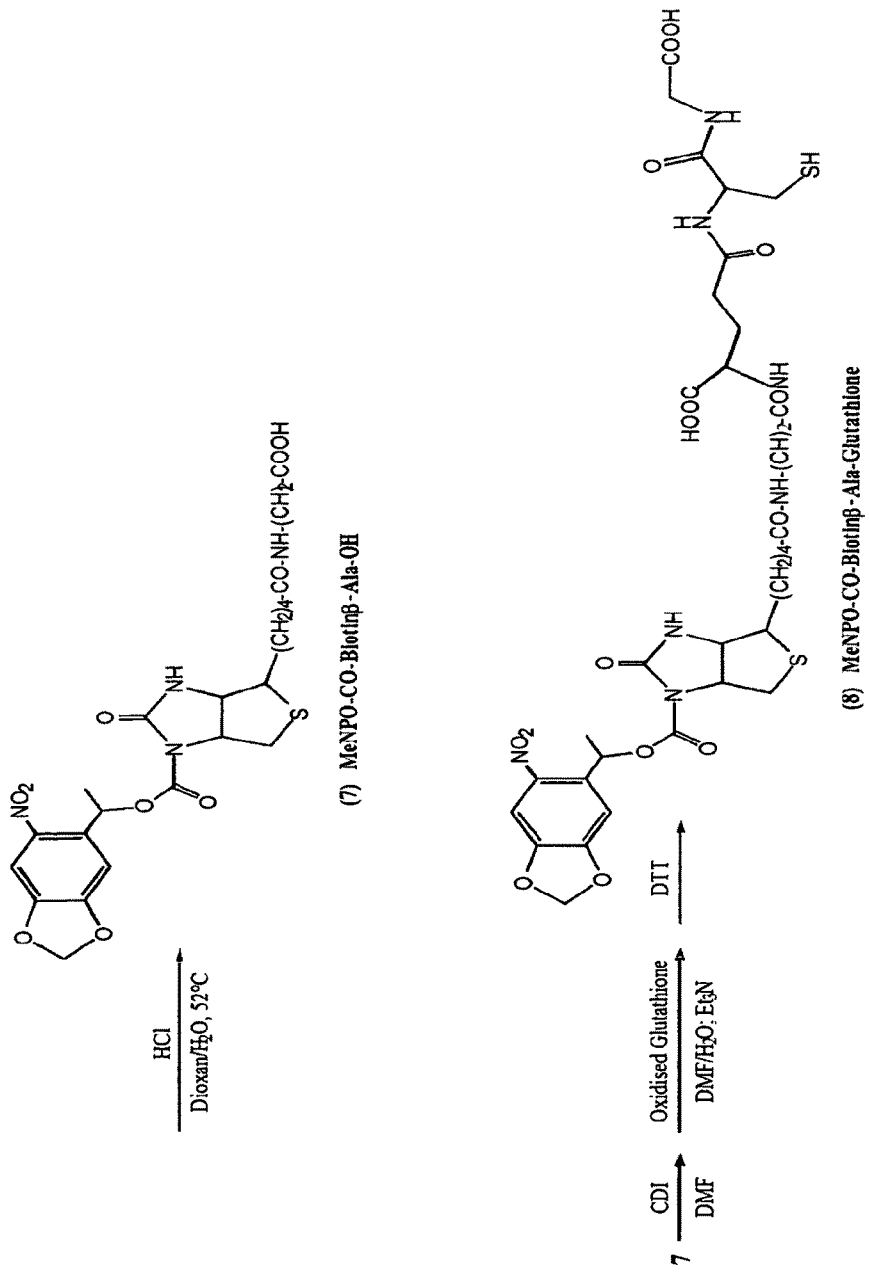

Biotin methyl ester (3, Biotin-OMe) was prepared essentially as described in Sundberg et al. (1995) (see FIG. 6):

Methylnitropiperonyl alcohol (1, MeNPOH). 3',4-(Methylenedioxy)-6'-nitroacetophenone (Lancaster; 6.2 g., 29.6 mmol) was dissolved in a mixture of THF (100 ml) and ethanol (100 ml). Sodium borohydride (1.12 g., 29.6 mmol) was added and the solution stirred for 3 hours at room temperature. TLC (on silica coated plates; solvent—3% methanol in DCM) indicated the full conversion of the starting material (Rf=0.8) to the alcohol (Rf=0.6). Hydrochloric acid (1N) was added slowly until the evolution of hydrogen stopped and the solvents evaporated under vacuum. The residual solid was dissolved in DCM (500 ml) and washed with brine (40 ml). The organic phase was dried (over $MgSO_4$) and the solvent removed under vacuum. Recrystallisation from hot DCM and hexane gave 6.1 g. of 1 (a yellow crystalline solid).

O-Methylnitropiperonyl-carbonylimdazole (2, MeNPO-CO-Im)

Methylnitropiperonyl alcohol (1.69 g, 8 mmol) was added (in several portions during 20 minutes) to a solution of carbonyldiimidazole (CDI, 2.6 g, 16 mmol) in DCM (50 ml). The solution was stirred for 3 hrs after which TLC indicated the complete conversion of the alcohol (Rf=0.6-3% methanol in DCM) into product (Rf=0.45). DCM (100 ml) and water (30 ml) were added and the reaction mixture transferred to a separatory funnel. The mixture was mixed and 1N HCl was added (in 1 ml aliquots) until the pH of the aqueous phase went below 6. The aqueous phase was removed, more water added (30 ml) and acidified to pH 6 while mixed. Finally, the DCM phase was washed with brine, dried (over $MgSO_4$) and the solvent removed under vacuum. The remnant solid was re-crystallised from hot DCM and hexane to give 2.2 g of 2 (a yellow crystalline solid).

N—(O-Methylnitropiperonyl-carbonyl)-Biotin methyl ester (4, MeNPO-CO-Biotin-OMe)

Sodium hydride (60% suspension in oil; 100 mg, 2.5 mmol) was added to a stirred suspension of Biotin-OMe (517 mg, 2 mmol) and MeNPO-CO-Im (305 mg, 1 mmol) in anhydrous DCM (10 ml) on ice. The solution was stirred for 30 minutes on ice and 30 minutes at room temperature. TLC indicated the complete disappearance of the MeNPO-CO-Im (Rf=0.6-5% methanol in DCM) and the appearance of the product (Rf=0.45). Traces of alcohol 1 (Rf=0.7), and a side-product with Rf=0.95 (probably di-MeNPO-carbonate) were also observed (The ratio of product vs. the above side-product varied from one preparation to another; careful drying of the starting materials and performing the reaction on ice gave generally higher yields of the product).

Once the reaction had been completed, DCM was added (100 ml) and the solution extracted three times with 1M $NaH_2PO_4$. The organic phase was dried ($MgSO_4$) and the solvent removed under vacuum. The remnant syrup was dissolved in hot DCM (ca. 5 ml), hexane (ca. 5 ml) was added to the cloud-point and the solution was allowed to stand at 4° C. overnight. This resulted in the precipitation of the excess of the Biotin-OMe as a white crystalline solid (which was washed with ether, dried and used in subsequent reactions). The filtrate was concentrated in vacuum and purified by chromatography on silica (1.5 to 3% methanol in DCM) to give 4 as a yellow foam (with yields up to 385 mg, or 80% based on molar equivalents of 2 as starting material).

N—(O-Methylnitropiperonyl-carbonyl)-Biotin (5, MeNPO-CO-Biotin-OH)

MeNPO-CO-Biotin-OMe (940 mg; 1.73 mmol) was dissolved in 25 ml of 0.5N HCl and dioxane (4:6; flashed with argon). The solution was stirred at 44° C. for 24 hours under argon. The solvents were reduced under vacuum to ca. 1 ml, water was added (10 ml) and the resulting mixture lyophilised. The resulting solid was dissolved in DCM with 2% methanol (20 ml) and charcoal was added. The mixture was boiled for few minutes and filtered. TLC (10% methanol in DCM) indicated the appearance of the product of the hydrolysis (Rf=0.2) and about 5% of starting material (MeNPO-CO-Biotin-OMe; Rf=0.9). The solvents were removed under vacuum to give a yellow solid that was dried under vacuum (860 mg of ca. 95% of 5 plus 5% of 4). Higher concentrations of HCl (e.g., 1N) and higher temperatures (e.g., reflux with THF as a co-solvent) resulted in complete hydrolysis of the methyl ester. However, significant amount of alcohol 1 and biotin were also observed, indicating the hydrolysis of the carbamate under these conditions. It should also be noted that methyl ester 4, and in particular, the product of its hydrolysis (5) were found to be sensitive to oxidation. Warming or even storing solutions of 5 in the presence of air resulted in browning. Similarly, attempts to purify 5 (or derivatives of, e.g., 7) by chromatography on silica led to very high losses due to oxidation.

N—(N—(O-Methylnitropiperonyl-carbonyl)-Biotin)-3-aminopropionic acid tert-butyl ester (6, MeNPO-CO-Biotin-β-Ala-OBu$^t$). MeNPO-CO-Biotin-OH (860 mg containing ~5% of MeNPO-CO-Biotin-Ome; ~1.6 mmol) was dissolved in 20 ml of anhydrous DCM. β-Alanine tert-butyl ester (H-β-Ala-OBu$^t$) hydrochloride salt (Bachem; 362 mg; 2 mmol), N-hydroxysuccinimide (172 mg; 1.5 mmol) and triethylamine (280 µl; 2 mmol) were added. The stirred solution was cooled on ice and EDCI was added (420 mg; 2.2 mmol). The reaction was stirred for 24 hours at 4° C. and 2 hours at room temperature. TLC (5% methanol in DCM) indicated the appearance of the product (Rf=0.3) and the remaining, unreacted MeNPO-CO-Biotin-OMe (Rf=0.45). The reaction was diluted with DCM (30 ml) and extracted three times with 1M NaH$_2$PO$_4$ and once with saturated NaHCO$_3$. The organic phase was dried (Na$_2$SO$_4$) and the solvent removed under vacuum. The remnant syrup was purified by chromatography on silica (3.0-4.5% methanol in DCM) to give 640 mg of 6 (a yellow foam).

N—(N—(O-Methylnitropiperonyl-carbonyl)-Biotin)-3-aminopropionic acid (7, MeNPO-CO-Biotin-β-Ala-OH). Tert-butyl ester 6 (510 mg; 0.84 mmol) was dissolved in 15 ml of 0.5N HCl and dioxane (4:6; flashed with argon). The solution was stirred at 52° C. for 24 hours under argon. Water was added (10 ml) and the resulting solution was freeze-dried to give a solid that contained (as judged by TLC) the product of the hydrolysis (7) and starting material (6; ~10%). This mixture was purified by column chromatography on silica (10% methanol in acetone plus 0.1 acetic acid) to give 60 mg of 7 (the low yields were primarily the result of oxidation of 7 on the silica).

N—(N—(N—(O-Methylnitropiperonyl-carbonyl)-Biotin)-3-aminopropionyl)-glutathione (8, MeNPO-CO-Biotin-β-Ala-GSH). Carbonyldiimidazole (20 mg, 120 µmol) was added to a solution of MeNPO-CO-Biotin-β-Ala-OH (7, 49 mg, 89 µmol) in DMF (1.5 ml). The solution was stirred for 30 minutes at room temperature and was then added, in several aliquots, to a solution of oxidised glutathione (62 mg, 100 µmol) and triethylamine (55 µl, 0.4 mmol), in DMF (2 ml) plus water (0.15 ml), stirred on ice. The solution was stirred on ice for 30 minutes and then at room temperature. Triethylamine was added, until the solution became clear (25 µl), and the reaction was then stirred for another 2 hours at room temperature. DTT was then added (0.25 ml of 1M solution; 0.25 mmol), and the solution was stirred at room temperature for 10 minutes.

The product of the above reaction was purified by reverse-phase HPLC, on an RP-8 preparative column, using a water-acetonitrile gradient in the presence of 0.1% trifluoroacetic acid. The peak corresponding to 8 (retention time=28.6 minutes) was collected. The product was then isolated by freeze-drying and purified again on reverse-phase HPLC (using the same column and solvent system). Analysis of the product after the second HPLC purification, using analytical reverse-phase HPLC, indicated a product (>95%) the UV spectrum of which corresponded to 8 (specifically, $\lambda^{max}$ at 355 nm indicated the presence of the O-methylnitropiperonyl-carbonyl group of the caged-biotin). The concentration of 8 was determined by titrating the free thiol groups (using DTNB, 5,5'-dithiobis (2-nitrobenzoic acid), as Hermanson, 1996) derived from the glutathione, and also by absorbance at 355 nm (corresponding to the caged-biotin). Both these independent measurements gave the same result within experimental error.

The purified 8 was also found to be a substrate for human M2-2 GST in the electrophilic substitution of CDNB (monitored by the change of absorbance at 340 nm; Habig & Jakoby, 1981) with rates that are about 10 fold slower than those observed with glutathione under similar conditions.

Figure 7:
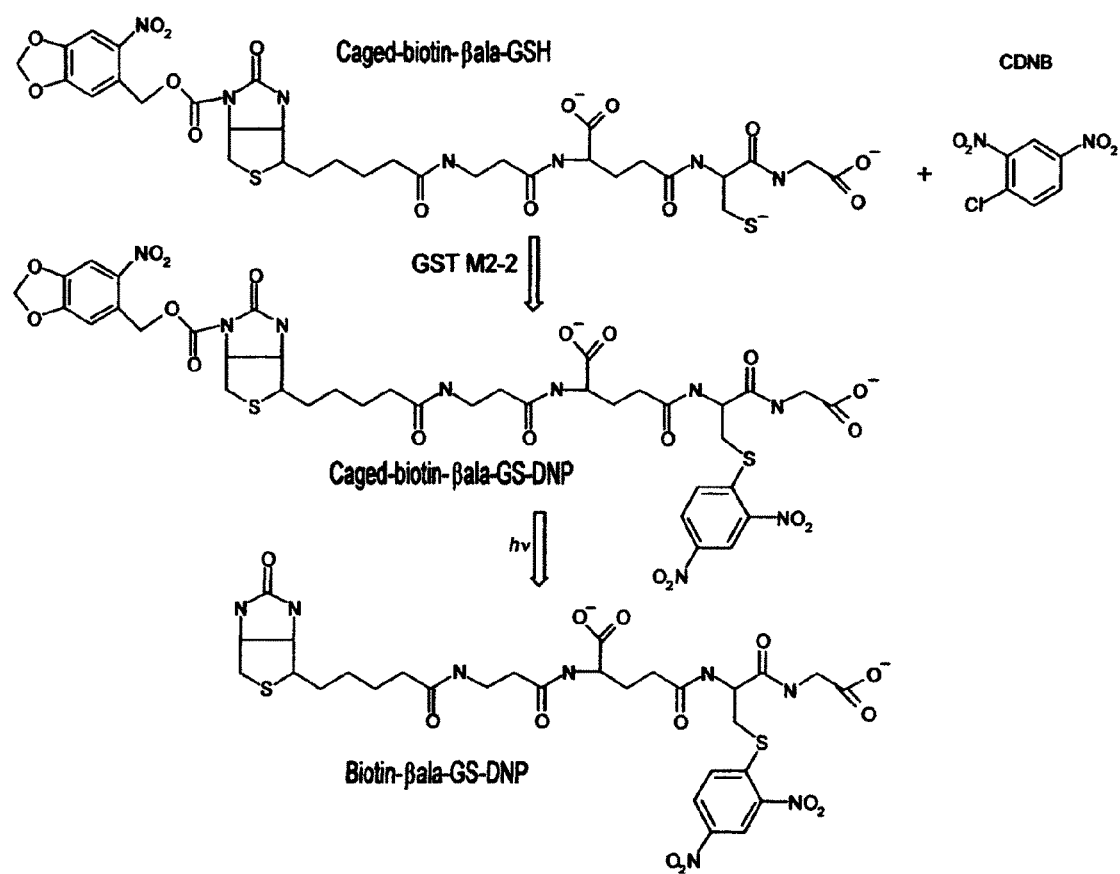
FIG. 7. Reaction of caged-biotin-βala-GSH with 1-chloro-2,4-dinitrobenzene (CDNB) and photochemical uncaging of the biotin group.
Figure 8:
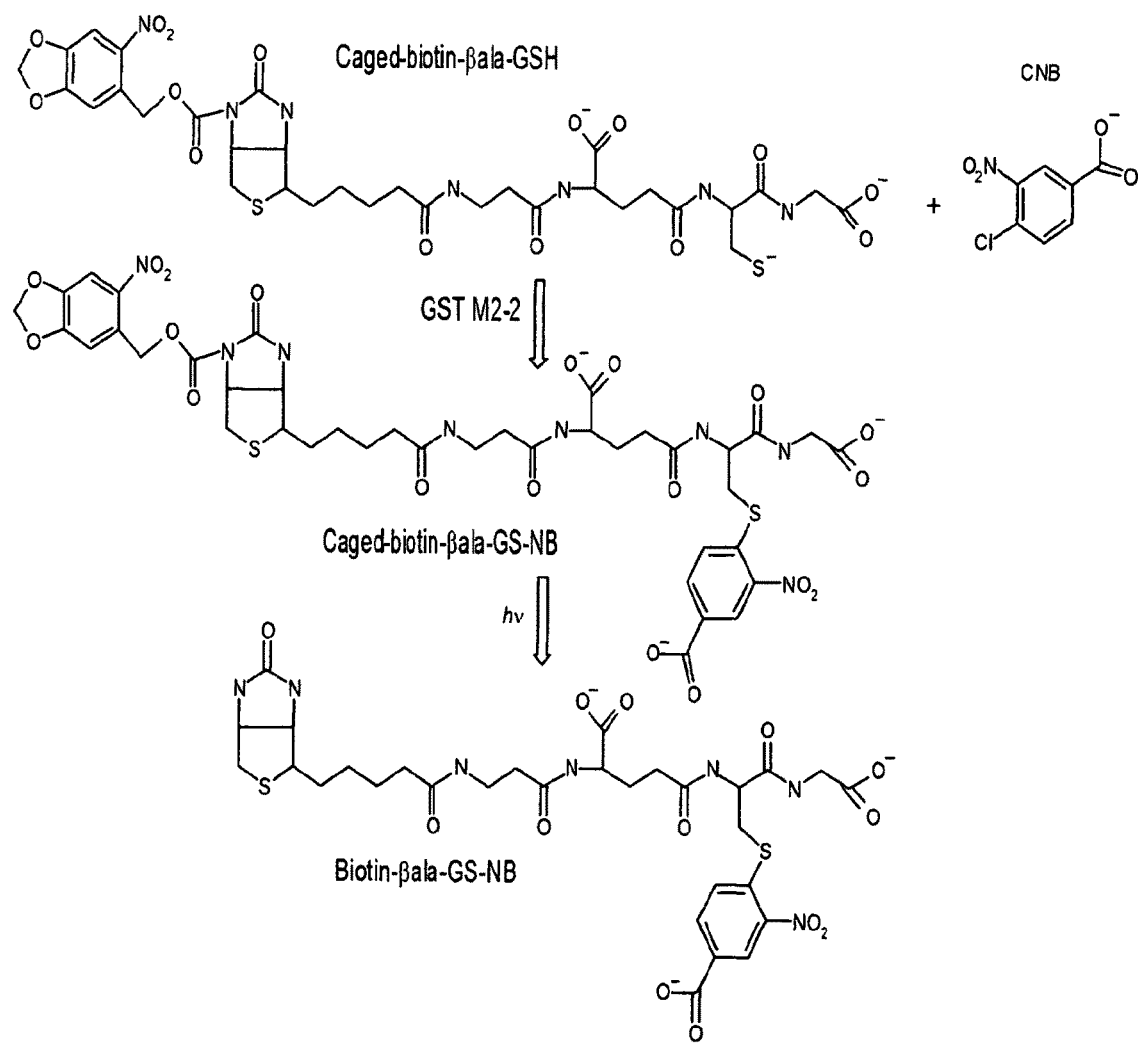
FIG. 8. Reaction of caged-biotin-βala-GSH with 4-chloro-3-nitrobenzoate (CNB) and photochemical uncaging of the biotin group FIG. 9. Human GST M2-2 catalyses the reaction of caged-biotin-βala-GSH with CDNB and CNB in solution and the reaction products can be uncaged by UV irradiation, captured on beads and detected using fluorescently labelled anti-product antibodies and flow cytometry.

The reduced MeNPO-CO-Biotin-β-Ala-GSH (caged-biotin-βala-GSH) was reacted with either 1-chloro-2,4-dinitrobenzene (CDNB; Sigma) or 4-chloro-3-nitrobenzoate (CNB, Acros). The caged product generated does not bind avidin or streptavidin. However, after photochemical uncaging by ultraviolet radiation the product has a biotin at one end which will bind to avidin or streptavidin-coated microparticles and either a 2,4-dinitrophenol (DNP) or a 3-nitrobenzoate group which can be bound by appropriate anti-DNP or anti-3-nitrobenzoate antibodies (see FIGS. 7 & 8)

5 µl (10$^8$ beads) 1.0 µm diameter nonfluorescent neutravidin labelled Microspheres (Molecular Probes, F-8777) were spun in a microfuge at 10,000 g for 3 min. and the supernatant removed. The beads were resuspended in 5 µl 0.1 M KH$_2$PO$_4$, pH 6.5, 1 mM EDTA, 2 mM dithiothreitol, 10 µM caged-biotin-βala-GSH, and either 500 µM CDNB or 500 µM CNB. The 5 µl reaction mixes contained either 0.75 µg purified recombinant human GST M2-2 or no enzyme.

Reactions were incubated for 30 min (CDNB reactions) or 4 hours (CNB reactions) at 25° C., after which time they were stopped by the addition of 35 µl 0.1 M sodium acetate, pH 5.0 and transferred to ice. Each reaction was then split into two aliquots of 20 µl each, one of which was placed as a spot on a layer of parafilm on the surface of an ice-cooled aluminium block. This spot was then irradiated for 2 min with a B 100 AP UV lamp (UVP) held at a distance of ~6 cm. The other aliquot was left un-irradiated. All samples were then incubated 30 mins. at ambient temperature and then washed three times with 200 µl PBS, 0.1% Tween 20 in a 0.45 µm MultiScreen-HV filter plate (Millipore, MAHVN4510), thoroughly resuspending between each wash.

Beads were then resuspend in 200 µl PBS, 0.1% Tween 20 containing 20 ng/µl Alexa-488 labelled rabbit anti-DNP antibody (Dako, #V0401) 20 ng/µl Alexa-488 labelled anti-CNB antisera and incubated for 1 hour at room temperature. The anti-CNB antiserum was elicited in rabbits by immunisation with CNB-CH$_2$-KLH conjugates prepared by adding aliquots of a 200 mM solution of 4-(bromomethyl)-3-nitrobenzoic acid (CNB-CH$_2$Br) in DMF to 5 mg/ml solutions of bovine serum albumin (BSA) or keyhole limpet hemocyanin (KLH) in 50 mM borate pH 8.8 (to give 1.5 to 6 µmole of CNB- CH$_2$Br per mg protein). The reaction mixtures were stirred for 6 hours at room temperature and temperature, and the resulting protein conjugates were dialysed extensively against phosphate buffer saline (PBS) at 4° C. The level of conjugation (hapten density or Hd) was determined by measuring optical densities of the conjugates at 355 nm. These were found to be: 7 to 11 CNB-CH$_2$ groups per BSA molecule and 9.4 to 24.3 per KLH molecule depending on the amount of CNB-CH$_2$Br added to the protein samples. The CNB-CH$_2$-KLH conjugate with Hd of 14.2 was used to immunise rabbits using published protocols (Tawfik et al., 1993; Tawfik et al., 1997) (by Prof. Z Eshhar, Weizmann Institute of Science, Rehovot). Sera were tested by ELISA for binding the conjugate CNB-CH$_2$-BSA (Hd=11) and to BSA. The first bleed from both immunised rabbits (when diluted 50 fold or more) exhibited the desirable selectivity yielding high signal when incubated with the CNB-CH$_2$-BSA conjugate and very low background (<5%) with BSA. The anti-CNB serum was purified using a HiTrap Protein A column (Pharmacia). Both anti-CDNB and anti-CNB antibodies were labelled with an Alexa Fluor 488 protein labelling kit (Molecular Probes) according to the manufacturer's instructions.

The beads were washed three times with 200 µl PBS, 0.1% Tween 20 as above, then resuspended in 1 ml PBS, 0.1% Tween 20 and 10,000 events analysed using a FACScan flow cytometer (Becton Dickinson).

Figure 9:
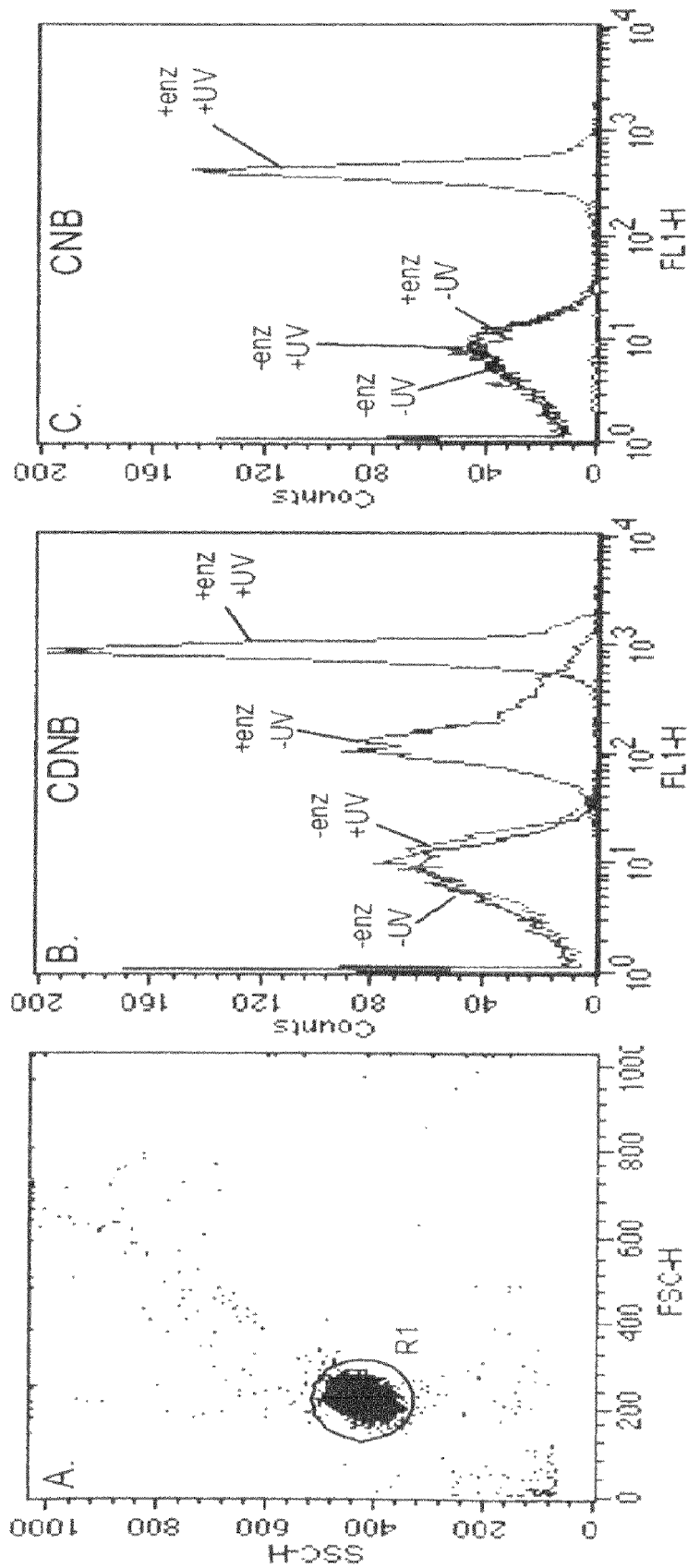

As can be seen from FIG. 9, the caged-biotin moiety is uncaged on UV irradiation and binds to beads. A 19-fold increase in mean bead fluorescence was observed after GST M2-2 catalysed reaction of caged-biotin-βala-GSH with CDNB even in, the absence of UV irradiation. This correlates with the apparent presence of ~4% biotin-βala-GSH in the preparation of caged-biotin-βala-GSH as determined by using fluorimetry to measure the displacement of 2-anilonaphthalene-6-sulphonic acid (2,6-ANS) from avidin (Mock et al., 1985). These results are consistent with the previously observed background immobilisation of caged-biotin to avidin 'in the dark' (i.e., without UV illumination) which was as high as 15% of the signal observed after illumination (Sundberg et al. 1995). The 'dark' signal observed previously was ascribed to either trace contaminants of biotin in the caged-biotin preparation, or to weak interactions between avidin and components of the caged-biotin including the linker (Sundberg et al. 1995). After UV irradiation a large difference in the mean fluorescence of those beads incubated in the presence and absence of GST was observed. The mean bead fluorescence with GST was 84 times and 56 times that observed without GST with CDNB and CNB as substrates respectively (FIG. 9).

Example 6

Glutathione S-Transferase M2-2 (GST M2-2) Compartmentalised in the Aqueous Droplets of a Water-in-Oil Emulsion Catalyses the Reaction of Caged-Biotinylated-Glutathione with 4-Chloro-3-Nitrobenzoate (CNB)

The Caged-Biotinylated Product Generated Remains Compartmentalised and Can Subsequently be Uncaged by UV Irradiation in the Compartments, Captured on an Avidin-Coated Bead in the Same Compartment and the Product-Coated Beads Detected by Flow Cytometry 20 µl aliquots (4×10$^8$ beads) of 1.0 µm diameter nonfluorescent neutravidin labelled microspheres (Molecular Probes, F-8777) or 0.93 µm diameter streptavidin-coated polystyrene beads (Bangs Laboratories) were each spun in a microfuge at 2,600 g (6,500 rpm) for 3 min. The supernatant was removed and the beads resuspended, on ice, in 20 µl 0.1 M KH$_2$PO$_4$, pH 6.5, 1 mM EDTA, 2 mM dithiothreitol, 50 µM caged-biotin-βala-GSH, containing either 3 µg purified recombinant human GST M2-2 or no enzyme.

Six reaction mixtures were then emulsified essentially as Tawfik & Griffiths (1998):
 a) Bangs beads, no GST
 b) Bangs beads, plus GST
 c) Molecular Probes beads, no GST
 d) Molecular probes beads, plus GST
 e) Bangs beads, no GST
 f) Molecular Probes beads, no GST The oil phase was freshly prepared by dissolving 4.5% (v/v) Span 80 (Fluka) in mineral oil (Sigma, #M-5904) followed by 0.5% (v/v) Tureen 80 (SigmaUltra; #P-8074); Ice-cooled reaction mixtures were added gradually (in 5 aliquots of 4 µl over ~2 minutes) to 0.4 ml of ice-cooled oil-phase in a 5 ml Biofreeze Vial (Costar, #2051) whilst stirring with a magnetic bar (8×3 mm with a pivot ring Scientific Industries International, Loughborough, UK). Stirring (at 1150 rpm) was continued for an additional 1 minute on ice.

8 µl of emulsion d) was added to 0.4 ml emulsion e), and 8 µl of emulsion b) was added to 0.4 ml emulsion f) (to give 1:50 dilutions) and the emulsion mixtures vortexed for 5 seconds to mix.

Six reaction mixtures were left non-emulsified:
 a) Bangs beads, no GST
 b) Bangs beads, plus GST
 c) Molecular Probes beads, no GST
 d) Molecular probes beads, plus GST
 e) Bangs beads, no GST
 f) Molecular Probes beads, no GST 0.4 µl of d) was added to 20 µl of e), and 0.4 µl b) was added to 20 µl of f) (to give 1:50 dilutions).

Both emulsions and non-emulsified reactions were incubated for 15 min at 25° C. Then 0.8 µl 500 mM CNB (in absolute ethanol) was added to each 0.4 ml emulsion and the emulsion vortexed for 5 seconds (the CNB is transferred through the mineral oil to the aqueous compartments). 5 µl 5 mM CNB (in 0.1 M KH$_2$PO$_4$, 1 mM EDTA, pH, 6.5) was added to the non-emulsified reactions.

All reactions were incubating for 4 hours at 25° C.

The pH of the aqueous droplets was lowered to quench the GST catalysed reaction by vortexing the emulsions with 200 µl Sigma Mineral Oil for Molecular Biology (M-5904) containing 4.5% Span 80 (Fluka), 0.5% Tween 80 (Sigma Ultra) in Sigma Mineral Oil for Molecular Biology) and 25 mM acetic acid. The non-emulsified reactions were quenched by adding 25 µl 0.5 M acetic acid.

All reactions were transferred to a 24-well flat bottom plate (Corning, #25820) floating on iced water and irradiated for 2 min with a B 100 AP UV lamp (UVP) held at a distance of ~6 cm. All samples were then incubated 30 mins. at ambient temperature.

The emulsions were transferred to 1.5 ml microfuge tubes, spun 1 min. 13.5 k rpm in a microfuge and the oil phase removed leaving the concentrated (but still intact) emulsion at the bottom of the tube. 200 µl 0.1M Na acetate, pH 5.0 were added and the emulsion broken by extracting 4 times with 1 ml hexane, vortexing between each hexane addition. Residual hexane was removed by spinning for 10 min at ambient temperature under vacuum in a Speedvac (Farmingdale, N.Y.).

All samples were then washed three times with 200 µl PBS, 0.1% Tween-20 in a 0.45 µm MultiScreen-HV filter plate (Millipore, MAHVN4510), thoroughly resuspending between each wash. Beads were then resuspend in 200 µl PBS, 0.1% Tween 20. 25 µl (~5×10$^7$ beads) were then added to 200 µl PBS, 0.1% Tween 20 containing 20 ng/µl Alexa-488 labelled anti-DNP antibody or 20 ng/µl Alexa-488 labelled anti-CNB antibody (see Example 5) and incubated for 1 hour at ambient temperature. The beads were washed three times with 200 µl PBS, 0.1% Tween 20 as above, then resuspended in 1 ml PBS, 0.1% Tween 20 and 300,000 events analysed using a FACScan flow cytometer (Becton Dickinson).

In the non-emulsified mixtures, where neither GST nor the product of the GST catalysed reaction, (caged-biotin-βAla-NB) were compartmentalised, all beads have a similarly low fluorescence (FIG. 10, Panels B and D). In contrast, in the emulsion mixtures, where both GST and the product of the GST catalysed reaction, (caged-biotin-βAla-NB) were compartmentalised, two populations of beads, one of low and one of higher fluorescence are clearly visible (FIG. 10, Panels C and E). Gating through R1 and R2 enables the Bangs and Molecular Probes beads to be largely separated on the basis of their slightly different light scattering characteristics (FIG. 10, Panel A). The ratio of Bangs to Molecular Probes beads passing through R1 is 68%:0.1% and the ratio passing through R2 is 0.08%:87%. Using these gates it is clear that the beads with high fluorescence are those which were compartmentalised with the enzyme GST. Hence, compartmentalisation of beads, enzyme and reaction product was obtained by emulsification and those beads present in compartments which contained enzymes can be distinguished from those which do not by their fluorescence characteristics.

Example 7

Human GST M2-2 can be Transcribed and Translated In Vitro in the Aqueous Compartments of a Water-in Oil Emulsion and Catalyses a Reaction which Gives Rise to a Change in the Fluorescence Properties of Co-compartmentalised Microspheres The gene encoding human glutathione S-transferase M2-2 (GST M2-2) is amplified by PCR using oligonucleotides GSTM2-2Fo and GSTM2-2Bc from a human GST M2-2 cDNA clone in pGEM-3Z (Baez et al., 1997). The PCR fragment is cloned into the vector pGEM-4Z (Promega) digested with HindIII and KpnI downstream of the lac promoter and T7 RNA polymerase promoter. The oligonucleotide GSTM2-2Bc appends the efficient phage T7 gene 10 translational start site upstream of the methyltransferase gene start codon. DNA sequencing identifies a clone with the correct nucleotide sequence, termed pGEM-hGSTM2- 2. The pGEM-hGSTM2-2 plasmid described above is amplified by PCR using primers LMB2 and LMB3 as above to create a 826 base pair PCR fragment (GSTM2-2.LMB2-3) which carries the T7 RNA polymerase promoter, the phage T7 gene 10 translational start site and the GST gene. The PCR fragment is purified directly using Wizard PCR Preps (Promega).

60 l aliquots ($1.2 \times 10^9$ beads) of 1.0 µm diameter nonfluorescent neutravidin labelled microspheres (Molecular Probes, F-8777) were spun in a microfuge at 10,000 g for 3 mm. The supernatant was removed and the beads resuspended, on ice, in 60 µl of a prokaryotic in vitro coupled transcription/translation system designed for linear templates (Lesley et al., 1991). A commercial preparation of this system is used (*E. coli* S30 Extract System for Linear Templates; Promega) supplemented with 12.5 mM acetic acid (to lower the pH to ~7.0), T7 RNA polymerase (2,000 units:), 12.5 µg/ml λ DNA-HindIII digest (New England Biolabs), 50 µM caged-biotin-βala-GSH, and, optionally, 5 nM GSTM2-2.LMB2-3 DNA or 5.0 µg of purified recombinant human GST M2-2 per 50 µl (or neither).

A 5 µl aliquot was removed from each reaction mixture and left non-emulsified. 50 µl of the remaining reaction mixture was emulsified essentially as Tawfik & Griffiths (1998).

The oil phase was freshly prepared by dissolving 4.5% (v/v) Span 80 (Fluka) in mineral oil (Sigma, #M-5904) followed by 0.5% (v/v) Tween 80 (SigmaUltra; #P-8074). Ice-cooled reaction mixtures were added gradually (in 5 aliquots of 10 µl over ~2 minutes) to 1.0 ml of ice-cooled oil-phase in a 5 ml Biofreeze Vial (Costar, #2051) whilst stirring with a magnetic bar (8×3 mm with a pivot ring; Scientific Industries International, Loughborough, UK). Stirring (at 1150 rpm) was continued for an additional 1 minute on ice.

Both emulsions and non-emulsified reactions were incubated for 45 min at 25° C. to allow translation to proceed. Then 5 µl 100 mM 1-chloro-2,4-dinitrobenzene (CDNB) (in absolute ethanol) was added to each 1.0 ml emulsion and the emulsion vortexed for 5 seconds (the CDNB is transferred through the mineral oil to the aqueous compartments). 1.0 µl 2.5 mM CDNB (in water) was added to the non-emulsified reactions. CDNB inhibits in vitro translation and adding it in this way, after translation is completed, maximises the yield of GST.

All reactions were incubating for 30 mins at 25° C. The pH of the aqueous droplets was then lowered to quench the reaction by vortexing the emulsions with 500 µl Sigma Mineral Oil for Molecular Biology (M-5904) containing 4.5% Span 80 (Fluka), 0.5% Tween 80 (Sigma Ultra) in Sigma Mineral Oil for Molecular Biology) and 25 mM acetic acid. The non-emulsified reactions were quenched by adding 5 µl 0.5 M acetic acid and 20 µl 0.1M Na acetate, pH 5.0.

All reactions were transferred to a 24-well flat bottom plate (Corning, #25820) floating on iced water and irradiated for 2 min with a B 100 AP UV lamp (UP) held at a distance of ~6 cm. All samples were then incubated 30 mins. at ambient temperature.

The emulsions were transferred to 1.5 ml microfuge tubes, spun 1 min. 13.5 k rpm in a microfuge and the oil phase removed leaving the concentrated (but still intact) emulsion at the bottom of the tube. 200 µl 0.1M Na acetate, pH 5.0 were added and the emulsion broken by extracting 4 times with 1 ml hexane, vortexing between each hexane addition. Residual hexane was removed by spinning for 10 min at ambient temperature under vacuum in a Speedvac (Farmingdale, N.Y.).

Approximately $5 \times 10^7$ beads from the broken emulsions and the non-emulsified reactions were then washed three times with 200 µl PBS, 0.1% Tween 20 in a 0.45 µm Multi-Screen-HV filter plate (Millipore, MAHVN4510), thoroughly resuspending between each wash. Beads were then resuspend 200 µl PBS, 0.1% Tween 20 containing 10 ng/µl Alexa-488 labelled anti-DNP antibody (see Example 5) and incubated for 1 hour at ambient temperature. The beads were washed three times with 200 µl PBS, 0.1% Tween 20 as above, then resuspended in 1 ml PBS, 0.1% Tween 20 and 10,000 events analysed using a FACScan flow cytometer (Becton Dickinson).

As can be seen from FIG. 11, both in emulsified and non-emulsified reactions, the reaction catalysed by in vitro translated GST M2-2 results in an in beads with higher fluorescence than when no enzyme was present. This difference in fluorescence would, however, not be sufficient for efficient fluorescence activated sorting (FACS). However, beads from both emulsified and non-emulsified reactions containing 5.0 µg of purified recombinant GST M2-2 per 50 µl were even more fluorescent than, those containing in vitro translated GST M2-2 enabling efficient enrichment of these beads by FACS from those incubated in the absence of GST. This simulates the situation where a mutant GST of higher activity than wild-type is translated in vitro.

Example 8

Genes Attached to Microbeads are Expressed In Vitro and the Resulting Gene-Product (an Enzyme) Binds to the Microbeads Whilst Retaining Catalytic Activity One format for the selection of genetic elements is where the genetic element comprises a gene linked to a microbead, which is translated in a microcapsule, and the translated gene-product is coupled back onto the microbead within the microcapsule. Thus, compartmentalisation leads to the formation of complexes of gene-products (e.g. proteins or enzymes) attached to the gene encoding them. These complexes could be subsequently selected for binding a ligand (see Example 12), or for enzymatic activity via a second compartmentalised reaction.

Here it is shown, that an enzyme (phosphotriesterase or PTE) can be transcribed and translated in vitro from genes attached to microbeads and the translated enzyme is bound back the microbeads. We also show that the translated enzyme can be modified, assembled or complemented with a cofactor whilst it is bound on the beads—in this example, metal ions are added to the apo-enzyme to give an active metalloenzyme. Moreover, we show here that the catalytic activity of the enzyme is retained whilst it is bound to the microbead together with the gene that encodes it.

The opd gene encoding a phosphotriesterase (PTE; also known as paraoxon hydrolase; Mulbry & Karns, 1989) is amplified from *Flavobacterium* sp. strain ATCC 27551 by PCR using a forward primer that appends stop codons and an EcoRI site (OPD-Fo; see Table 1), and a back primer that appends the phage T7 gene 10 transitional site (RBS) and a HindIII cloning site (OPD-Bc). This DNA is cloned into pGEM-4Z using the HindIII and the EcoRI sites downstream of the T7 RNA polymerise promoter. DNA sequencing identifies a clone which has the correct nucleotide sequence. Bacteria (*E. coli*, TG1) transformed with this clone (Gem-OPD) are found to overexpress active PTE when grown in the presence of cobalt chloride and induced with IPTG (Omburo et al., 1992).

The OPD gene is also cloned with a Flag™ peptide (Met-Asp-Tyr-Lys-Asp-Asp-Asp-Asp-Lys; Sigma-Aldrich) appended to its N-terminus. The OPD gene is amplified *Flavobacterium* sp. strain ATCC 27551 by PCR using a forward primer (N-Flag-OPD-Fo) that appends stop codons and a KpnI site, and a back primer (N-Flag-OPD-Bc) appending an NcoI site, a Flag peptide and a short linker between the Flag peptide and the OPD reading frame. The resulting DNA fragment is cloned into plasmid pGEM-4Z$^{NcoI}$ (using the KpnI and NcoI sites). pGEM-4Z$^{NcoI}$ is a modification of p-GEM-4Z into which, the phage T7 gene 10 transitional site (RBS) and an ATG start codon are appended downstream to the T7 RNA polymerise promoter, to create an NcoI site that allows cloning of reading frames in the context of the RBS and ATG codon. The sequence of the section incorporated into pGEM-4Z (between the HindIII and the KpnI sites downstream to the T7 RNA polymerise promoter), to give pGEM-4Z$^{NcoI}$, is indicated in Scheme I.

The rest of pGEM-4Z, including the KpnI and EcoRI cloning sites, remained intact.

DNA sequencing identifies a clone that has the correct nucleotide sequence. Bacteria transformed with this clone (Gem-N-Flag-OPD) are found to over-express an active PTE when grown in the presence of Cobalt Chloride and induced with IPTG.

The gem-OPD and gem-N-Flag-OPD plastids described above are amplified by PCR, using primers LMB2-biotin and LMB3, to create DNA fragments (OPD.LMB3-2biotin and N-Flag-OPD.LMB3-2biotin, respectively) that carry the T7 RNA polymerise promoter, the phage T7 gene 10 transitional start site and the OPD or the N-Flag-OPD genes and are labelled with biotin at the 3' end. The PCR fragments are purified directly using Wizard PCR Preps (Promega).

Aliquots of a suspension of 0.95 μm non-fluorescent streptavidin labelled microspheres (Bangs, ~2×10$^7$ beads per μl suspension) are spun in a microfuge at 10,000 g (13.500 rpm) for 3 min. The supernatant is removed and the beads resuspended in TNT buffer (0.1M Tris 7.5, 0.15M NaCl, 0.05% Tween-20). An antibody that is capable of binding amino-teimini Flag peptides and is labelled by biotinylation (BioM5, a biotin-labelled anti-Flag antibody; Sigma) is added to the bead suspensions to an average of 4×10$^4$ antibody molecules per bead. The resulting mixture is incubated for several hours with occasional mixing. The beads are rinsed twice by spinning down and resuspending them in TNT buffer. Biotinylated DNA fragments (fragments OPD.LMB3-2biotin, N-Flag-OPD.LMB3-2biotin, or fragments that carry the T7 RNA polymerise promoter, the phage T7 gene 10 transitional start site and a gene encoding a different enzyme that is also tagged with N-Flag peptide, e.g., methyltransferase HaeIII-N-Flag-M.HaeIII.LMB3-2biotin) are added to a suspension of antibody-coated beads and the mixture is incubated overnight at 4° C. The beads are rinsed 3 times by spinning down and resuspending them in TNT buffer.

50 μl aliquots of the above suspension of beads (~10$^9$ beads) are spun in a microfuge at 10,000 g for 3 min. The supernatant is removed and the beads gently resuspended, on ice, in 50 μl of a prokaryotic in vitro coupled transcription/translation system designed for linear templates (Lesley et al., 1991). A commercial preparation of this system is used (*E. coli* S30 Extract System for Linear Templates; Promega) supplemented with T7-RNA polymerise (2,000 units). The reactions are incubated at 25° C. for 1.5 hours and spun in a microfuge at 10,000 g for 3 min. The supernatant is removed and the beads resuspended in 100 μl of 50 mM Tris, 10 mM of Potassium Carbonate, pH 8.0. An aqueous solution of Cobalt Chloride is added to a concentration of 1 mM and the reactions incubated for several hours at room temperature (or overnight at 4° C.). The beads are rinsed 4 times by spinning down and resuspending them in TNT buffer.

Aliquots of the above beads are added to a solution of 0.25 mM Paraoxon in 50 mM Tris pH 8.3. The beads are incubated at 25° C. with occasional stirring for different periods of time. The beads are spun in a microfuge at 10,000 g for 3 min, the supernatant is removed and its optical density measured at 405 nm. A significant change in optical density, relative to the optical density observed under the same conditions in the absence of beads or phosphotriesterase, is not observed when

SCHEME I

```
----- 5'-AAGCTTAATAATTTTGTTTAACTTTAAGAAGGAGATATAGCCATGG. . .
pGEM-4Z-HindIII site           appended RBS, ATG and NcoI cloning site . . . GGTACC-3'--------
     KpnI site of pGEM-4Z
``` beads to which biotinylated DNA fragments OPD.LMB3-2biotin or N-Flag-M.HaeIII.LMB3-2biotin are attached (and are subsequently reacted as described above) are incubated with Paraoxon. However, a significant change in optical density at 405 nm is observed when beads to which biotinylated DNA fragments N-Flag-OPD.LMB3-2biotin are attached (and are subsequently reacted as described above) are incubated with Paraoxon. For example, when biotinylated DNA fragments N-Flag-OPD.LMB3-2biotin are added at a concentration of 1 nM (to a 50 µl suspension of beads (~$10^9$ beads) that is then resuspended in 50 µl in vitro transcription/translation), and reacted as described above, the change in optical density observed after 3 hours corresponds to more than 50% hydrolysis of Paraoxon (at 0.25 mM in a 50 µl reaction volume). Thus, microbeads carrying a gene encoding a protein with the desired catalytic activity (phosphotriesterase in the above example) can be clearly distinguished from microbeads carrying genes that do not encode a protein with the desired catalytic activity (methyltransferase HaeIII in the above example). Moreover, almost no change in optical density at 405 nm is observed when biotinylated DNA fragments N-Flag-OPD.LMB3-2biotin are attached to beads and reacted as described above, except that Cobalt Chloride is not added to the resuspended beads after transcription/translation.

These results show that an enzyme (phosphotriesterase) can be transcribed and translated in vitro from genes that encode this enzyme and are attached to microbeads. When the genes encode a tag—an N-terminus Flag peptide in the above example—the translated enzyme binds back to the microbeads to which the genes are attached. If necessary, the translated enzyme can be then modified whilst it remains attached to the microbeads (together with the gene that encodes it)—in this example, Cobalt ions are added to give a reactive metalloenzyme. These result also indicate that the enzyme is catalytically active whilst it is bound to microbeads together with the gene that encodes it.

Example 9

An Enzyme Catalyses a Reaction with a Caged-Biotinylated Substrate, and the Caged-Biotinylated Product Generated is Uncaged by UV Irradiation and Captured on Streptavidin-Coated Microbeads Subsequently these Beads are Detected by Flow-Cytometry One format for the selection of genetic elements is where the genetic element comprises a gene linked to a microbead, which is translated in a microcapsule, and the translated gene-product is coupled back onto the microbead within the microcapsule. Thus, compartmentalisation leads to the formation of complexes of gene-products (e.g., proteins or enzymes) attached to the gene encoding them. These complexes could be subsequently selected for binding a ligand (see Example 12), or for enzymatic activity via a second compartmentalised reaction.

However, for such complexes to be selected for catalytic activity, a soluble substrate should be available for the immobilised enzyme, and, once the catalytic reaction had been completed, the product of the enzymatic activity that is being selected for should become attached to the gene encoding this enzyme. The resulting complexes could be then sorted or selected by virtue of the product being linked to them, for example by using a fluorescently-labelled antibody that recognises the product. In other compartments, containing complexes of genes and gene-products that do not encode proteins with the desired enzymatic activity, the unreacted substrate should become linked to the gene. These complexes will not be labelled with the product and will therefore be discarded.

Here it is shown that an enzyme (phosphotriesterase or PTE) can react with a caged-biotinylated substrate in the presence of streptavidin-coated beads. The caged-biotinylated product generated can then be uncaged by UV irradiation and captured on avidin-coated beads. Subsequently, these beads are detected by flow cytometry and are clearly distinguished from beads incubated with a caged-biotinylated substrate in the presence of other enzymes or proteins that do not exhibit phosphotriesterase activity.

A caged-biotinylated substrate for PTE (EtNP-Bz-Glu-cagedBiotin; FIG. 12) is synthesised as follows:

Boc-5-aminopentanol: Di-tert-butyl dicarbonate (20.8 g; 0.095 mol) is added to stirred solution of 5-aminopentanol (10.37 g; 0.1 mol) in dicholoromethane (DCM) (200 ml) on ice. Following addition, the solution becomes turbid and a syrup separates. Triethylamine is added (13.8 ml; 0.1 mol) drop-wise, and the resulting solution is stirred for 10 minutes on ice and then overnight at room temperature. The solvents are removed under vacuum, the resulting syrup is dissolved in ethyl acetate (500 ml), extracted 3 times with 1M $Na_2HPO_4$ (pH 4), once with saturated $NaHCO_3$, and finally with brine, and then dried over $MgSO_4$. The solvents are removed under vacuum and the resulting syrup (after extensive drying under vacuum in the presence of potassium hydroxide), comprised primarily of Boc-5-aminopentanol, is used without further purification.

(11) Triethylamine (3 ml; 22 mmol) is added drop-wise to a stirred solution of p-nitrophenyl phoshphodichloridate (5.15 g; 20 mmol) and ethanol (1.15 ml, 20 mmol) cooled on dry-ice in acetone, with in 30 minutes. The solution is allowed to slowly warm up to room temperature and is stirred for an additional 90 minutes. A solution of Boc-5-aminopentanol (4.3 g; ca. 20 mmol) and trietheylamine (3 ml; 22 mmol) in DCM (20 ml) is then added drop-wise. The reaction is allowed to stir at room temperature for 10 minutes, 1H-tetrazole is added (0.35 g; 5 mmol) and the reaction stirred for another 2 hours. DCM is added (100 ml) and the solution extracted 3 times with 1M $Na_2HPO_4$ (pH 4), saturated $NaHCO_3$, and finally with brine, and then dried over $MgSO_4$. The solvents are removed under vacuum to give a syrup that is purified by column chromatography on silica (solvent: 1% to 2% methanol in DCM) to give 3.52 g of 11 (a syrup).

4-N-Boc-aminomethylbenzoic acid N-hydroxy succinimide ester: Dicyclohecyldicarbodiimide (DCC; 5.15 g; 25 mmol) is added to a stirred suspension of 4-N-Boc-aminomethylbenzoic acid (Tiger, Monmouth N.J.; 5.2 g; 25 mmol) and N-hydroxy succinimide (2.88 g; 25 mmol) in DCM (200 ml) plus acetonitrile (20 ml). The reaction is stirred overnight at 4° C. and then 3 hours at room temperature. The dicyclohexyl urea precipitate is removed by filtration, and the filtrate concentrated under vacuum to give a syrup. The syrup is dissolved in chloroform and DCM and treated with activated charcoal. Addition of ether gives a white crystalline solid. Recrystallisation from DCM and petroleum ether gives 6.2 g of the N-hydroxy succinimide ester of 4-N-Boc-aminomethylbenzoic acid.

(12) Trifluoroacetic acid (TFA; 4 ml) is added to a solution of 11 (900 mg; 2.07 mmol) in DCM (5 ml). The solution is left at room temperature for 45 minutes and the solvents are removed under vacuum. The residual syrup is triturated by dissolving it DCM and methanol and adding ether. The resulting 12 (as TFA salt; syrup) is dried over vacuum in the presence of potassium hydroxide, and then reacted immediately without further purification (see below).

(13) 4-N-Boc-aminomethylbenzoic acid N-hydroxy succinimide ester (670 mg; 2.2 mmol) and triethylamine (0.345 ml; 2.5 mmol) are added to 12 (see above) in DCM (15 ml). The solution is stirred for 30 minutes, triethylamine (0.1 ml; 0.72 mmol) is added, and the solution stirred for additional 3 hours. DCM is added (20 ml), and the solution extracted twice with 1M $Na_2HPO_4$ (pH 4), once with saturated $NaHCO_3$, and finally with brine, and then dried over $MgSO_4$. The solvents are removed under vacuum to give a syrup that is purified by column chromatography on silica (solvent: 5% methanol in DCM) to give 0.86 g of 13 (a syrup).

(14) 0.84 g 13 of 14 (1.6 mmol) is treated with TFA as described above to give 14 (as TFA salt; syrup) which is reacted immediately as described below.

(15) Boc-Glu(OSu)-OBu$^t$ (Bachem; 641 mg; 1.6 mmol) and triethylamine (0.235 ml; 1.7 mmol) are added to 14 (see above) in DCM (15 ml). The solution is stirred for 1 hour, triethylamine (60 µL; 0.43 mmol) is added, and the solution stirred for 1 hour. DCM is added (20 ml), and the solution extracted twice with 1M $Na_2HPO_4$ (pH 4), once with saturated $NaHCO_3$, and finally with brine, and then dried over $MgSO_4$. The solvents are removed under vacuum to give a syrup that is purified by column chromatography on silica (solvent: 7% methanol in DCM) to give 0.8 g of 15 (a white crystalline solid).

EtNP-Bz-Glu (16) 0.4 g of 15 (0.56 mmol) are dissolved in DCM (5 ml) and TFA (5 ml). The solution is stirred for 1 hour at room temperature, and the solvents are removed under vacuum. The residual syrup is crystallised by dissolving it methanol and adding ether. Recrystallisation (in methanol and ether) gives 200 mg of 16 (as TFA salt; white solid).

EtNP-Bz-Glu-cagedBiotin (17) Carbonyldiimidazole (6 mg, 37.5 µmol) is added to a solution of MeNPO-CO-Biotin-OH (5, 17 mg, 35 µmol) in DMF (1 ml). The solution is stirred for 60 minutes at room temperature and added to 16 (20 mg, 30 µmol). Triethylamine (5.5 µl, 40 µmol), DMF (1 ml) and water (0.5 ml) are added to the stirred reaction mixture until it became clear. The solution is stirred for 2 hours at room temperature and stored at −20° C.

The product of the above reaction is purified by reverse-phase HPLC on a C8 preparative column using a water-acetonitrile gradient in the presence of 0.1% trifluoroacetic acid. The peak corresponding to 17 (retention time=23.1 minutes) is collected. The product is isolated by freeze-drying as a yellow solid. Analysis of the product after the HPLC purification using analytical reverse-phase HPLC indicated a major product (>80%), the UV spectrum of which corresponded to 17. Specifically, $\lambda^{max}$ at 355 nm indicates the presence of the O-methylnitropiperonyl-carbonyl group of the caged-biotin (Pirrung & Huang, 1996), and a 'shoulder' at 277 nm, absent in caged-biotin, indicates the presence of the p-nitrophenyl phosphate ester of 17. The concentration of 17 is verified by hydrolysing the p-nitrophenyl phosphate ester in 0.1M potassium hydroxide and determining the amount of p-nitrophenol released (optical density at 405 nm).

The purified 17 is also found to be a substrate for PTE leading to the release of p-nitrophenol (FIG. 13; monitored by the change in optical density at 405 nm) with rates that are only about 6 fold slower than those observed with Paraoxon. Notably, unlike the base-catalysed hydrolysis of 17 which proceeds to completion (and the PTE-catalysed hydrolysis of Paraoxon), the PTE-catalysed hydrolysis of 17 proceeds with significant rates only until half of the substrate has been hydrolysed. The second half of the substrate could also be hydrolysed, but only in the presence of much higher quantities of PTE and after long incubations (several hours to overnight). This is probably due to the fact that there 17 is comprised of two diastereomers (corresponding to two enantiomers with regard to the chiral phosphotriester), only one of which is an effective substrate for the enzyme. Indeed, stereoselectivity was previously observed with PTE and other chiral phosphotriesters (Hong & Raushel, 1999).

Antibodies are generated that would recognise ethyl-phosphodiesters that are the products of hydrolysis of the corresponding p-nitrophenyl phosphotriesters. To this end, a suitable ethylphosphodiester derivative is synthesised and conjugated to carrier proteins as described below (FIG. 14).

EtNPBG (18) (Glutaric anhydride (180 mg; 1.6 mmol) and triethylamine (0.22 ml; 1.6 mmol) are added to 12 (prepared by de-protection of 1.6 mmol of 11, as described above) in DCM (15 ml). The solution is stirred for 20 minutes, triethylamine (0.12 ml; 0.85 mmol) is added, and the solution stirred for an additional 1 hour. DCM is added (20 ml), and the solution extracted twice with 1M $Na_2HPO_4$ (pH 4) and then dried over $MgSO_4$. The solvents are removed under vacuum to give a syrup that is purified by column chromatography on silica (solvent: 12.5% methanol in DCM plus 0.1% acetic acid) to give 445 mg of 18 (a syrup).

Substrate conjugates EtNPBG-KLH and EtNPBG-KLH. Carbonyldiimidazole (CDI; 32 mg, 200 µmol) is added to a solution of 18 (60 mg, 134 µmol) in DMF (1 ml). The solution is stirred for 60 minutes at room temperature. Aliquots of the activated 18 are then added to 5 mg/ml solutions of bovine serum albumin (BSA) or keyhole limpet hemocyanin (KLH) in 0.1M phosphate pH 8.0 (at 0.5 to 4 µmole of 18 per mg protein). The reactions are stirred for 1 hour at room temperature, and the resulting protein conjugates are dialysed extensively against phosphate buffer saline (PBS) at 4° C. The level of conjugation (hapten density or Hd) is determined by hydrolysing a sample of the dialysed conjugates in 0.1M potassium hydroxide and monitoring the amount of released p-nitrophenol (at 405 nm). These are found to be: 8.5 to 24 EtNPBG molecules per BSA molecule and 14 to 63 per KLH molecule depending on the amount of activated 18 added to the protein samples.

Product conjugates EtBG-KLH and EtBG-KLH. The EtNPBG-KLH and EtNPBG-KLH conjugates described above are dialysed against 0.1M carbonate pH 11.8 for 44 hours at room temperature, and then extensively against PBS (at 4° C.).

Anti-EtBG antibodies were elicited in rabbits by immunisation with EtBG-KLH (Hd=14) using published protocols (Tawfik et al., 1993; Tawfik et al., 1997) (gift of Prof. Z Eshhar, Weizmann Institute of Science, Rehovot). Sera are tested by ELISA for binding to both the substrate conjugate EtNPBG-BSA (Hd=8.5) and the corresponding product conjugate (EtBG-BSA; Hd=8.5). The first bleed from one of the immunised rabbits (when diluted 500 fold or more) exhibits the desirable selectivity, yielding high signal when incubated with the product conjugate and a low background (<20%) with the substrate conjugate. Diluting the sera in COVAp buffer (2M NaCl, 10 g, 1 $MgSO_4 7H_2O$, 0.04% Tween-20, 10 mM phosphate, 0.1 mM p-nitrophenol, pH 6.5) further increases selectivity, with background levels going below 5%. The anti-EtBG serum is purified using a HiTrap Protein A column (Pharmacia). The purified rabbit antibodies are labelled with an Alexa Fluor 488 protein labelling kit (Molecular Probes) according to the manufacturer's instructions.

10 µl (~$2 \times 10^8$ beads) of 0.95 µm streptavidin-coated microbeads (Bangs, ~$2 \times 10^7$ beads per µl suspension) are spun in a microfuge at 10,000 g for 3 min. and the supernatant removed. The beads are resuspended in 10 µl of 50 mM Tris pH 8.3 containing EtNP-Bz-Glu-cagedBiotin (17) to give a final concentration of 10 µM, 20 µM or 30 µM. PTE is expressed in vitro by transcription/translation of OPD.LMB3-2biotin DNA fragments (at 5 nM). A commercial preparation is used (*E. coli* S30 Extract System for Linear Templates; Promega) supplemented with T7 RNA polymerise (2,000 units) and the reactions are incubated at 25° C. for 1.5 hours. The PTE is then assembled by the addition of Potassium Carbonate (10 mM) and Cobalt Chloride (1 mM) in Tris buffer (10 mM pH 8.0) and incubating for overnight at 4° C. Another enzyme, that does not exhibit phosphotriesterase activity, methyltransferase HaeIII, is also expressed in vitro by transcription/translation from M.HaeIII.LMB3-2biotin DNA fragments (at 5 nM), and then treated with carbonate and cobalt as with the PTE. 5 µl aliquot of the above reaction mixtures are added to the bead suspensions and the reactions are incubated for 1 hour at 25° C. in the dark. The reaction is stopped by the addition of 15 µl 0.1 M sodium acetate, pH 5.0 and transferred to ice. Each reaction is then split into two aliquots of 15 µl each, one of which is placed as a spot on a layer of parafilm on the surface of an ice-cooled aluminium block. This aliquot is then irradiated for 2 min with a B 100 AP UV lamp (UVP) held at a distance of ~6 cm. The other aliquot is left in the dark. All bead samples are then incubated for 30 minutes at ambient temperature and washed three times with 200 µl PBS. 0.1% Tween 20 in a 0.45 µm MultiScreen-HV filter plate (Millipore, MAHVN4510), thoroughly resuspending between each wash. Beads (~$2 \times 10^7$) are then resuspended in 200 µl COVAp containing 100 ng/µl Alexa-488 labelled rabbit anti-EtBG antibodies and incubated for 1 hour at room temperature and then 1 hour at 4° C. The beads were washed three times with 200 µl PBS, 0.1% Tween 20 as above, then resuspended in 1 ml PBS, 0.1% Tween 20 and 10,000 events analysed using a FACScan flow-cytometer (Becton Dickinson).

As can be seen in FIG. 15, up to 20-fold increase in mean bead fluorescence is observed following the PTE catalysed hydrolysis of EtNP-Bz-Glu-cagedBiotin in the presence of streptavidin-coated beads and after UV irradiation. This is increase is observed relative to beads treated essentially the same but in the presence of another enzyme (M.HaeIII), with no phosphotriesterase activity. Notably, the differences in fluorescence signal are observed when both the PTE and the M.HaeIII, are expressed in vitro from the corresponding genes and are added together with the entire content of the in vitro transcription/translation reaction mixture.

At high substrate concentrations the observed mean fluorescence is lower than observed at 20 µM. In addition, at substrate concentrations above 20 µM, there is essentially no difference in the fluorescence signal between reactions kept in the dark and those UV irradiated (data not shown). Since the beads, under the reaction conditions described above, start to exhibit saturation of binding signal at concentrations above 10 µM (of product as detected by the subsequent addition of fluorescently-labelled anti-EtBG antibodies), these results may be explained by the presence of a contamination of ETNP-Bz-Glu-Biotin in the preparation of EtNP-Bz-Glu-cagedBiotin. These results are also consistent with the previously observed background immobilisation of caged-biotin to avidin 'in the dark' (i.e., without UV illumination) which was as high as 15% of the signal observed after illumination (Sundberg et al. 1995). The 'dark' signal observed previously was ascribed to either trace contaminants of biotin in the caged-biotin preparation, or to weak interactions between avidin and components of the caged-biotin including the linker (Sundberg et al. 1995). Both mechanisms may account for the fact that at high concentrations of caged-biotinylated substrate (and above the binding capacity of the beads), the 'dark' signal becomes significant. Nevertheless, at substrate concentrations of 20 µM, or lower, the 'dark' signal constitutes only 25%, or even less than 10% (e.g., at 10 µM EtNP-Bz-Glu-cagedBiotin) of the illuminated signal. This indicates that most of the PTE-catalysed hydrolysis of EtNP-Bz-Glu-cagedBiotin takes place whilst the substrate is in solution and not attached to the beads, and that the resulting product (Et-Bz-Glu-cagedBiotin), after illumination with UV light, is un-caged and becomes immobilised onto the microbeads.

Example 10

Genes Attached to Beads are Expressed In Vitro and the Resulting Gene-Products (Enzymes) Become Immobilised to the Microbeads Whilst Retaining Catalytic Activity The Immobilised Enzyme Catalyses a Reaction with a Caged-Biotinylated Substrate, and the Resulting Caged-Biotinylated Product is Subsequently Uncaged by UV Irradiation and Becomes Attached to these Beads Together with the Gene Encoding the Enzyme that LED to its Formation. Subsequently, these Beads are Detected by Flow-Cytometry One format for the selection of genetic elements is where the genetic element comprises a gene linked to a microbead, which is translated in a microcapsule, and the translated gene-product is coupled back onto the microbead within the microcapsule. Thus, compartmentalisation leads to the formation of complexes of gene-products (e.g., proteins or enzymes) attached to the gene encoding them. These complexes could be subsequently selected for binding a ligand (see Example 12), or for enzymatic activity via a second compartmentalised reaction.

For such complexes to be selected for catalytic activity, a soluble substrate should be available for the immobilised enzyme, and, once the catalytic reaction had been completed, the product of the enzymatic activity that is being selected for should become attached to the gene encoding this enzyme. The resulting complexes could be then sorted or selected by virtue of the product being linked to them, for example by using a fluorescently-labelled antibody that recognises the product. In other compartments, containing complexes of genes and gene-products that do not exhibit the desired enzymatic activity, the unreacted substrate would become linked to the gene. These complexes will not be labelled with the product and will therefore be discarded.

Here it is shown that an enzyme (phosphotriesterase or PTE) can be transcribed and translated in vitro from genes attached to microbeads and the translated enzyme is bound back to the microbeads. The translated enzyme can be then modified to incorporate the active-site Cobalt, and its catalytic activity is retained whilst it is bound to the microbead together the gene that encodes it. The immobilised PTE subsequently reacts with a caged-biotinylated substrate, and the caged-biotinylated product generated is uncaged by UV irradiation and captured onto the same avidin-coated beads to which the gene encoding the PTE is attached. Subsequently these beads are detected by flow-cytometry and are clearly distinguished from beads carrying a gene encoding a protein that does not exhibit phosphotriesterase activity.

Aliquots of a suspension of 0.95 µm streptavidin-coated microspheres (Bangs, ~$2 \times 10^7$ beads per µl suspension) are spun in a microfuge at 10,000 g for 3 min. The supernatant is removed and the beads resuspended in TNT buffer (0.1M Tris 7.5, 0.15M NaCl, 0.05% Tween-20). An antibody, capable of binding the Flag peptide and biotinylated (BioM5, a biotin-labelled anti-Flag antibody; Sigma) is added to the bead suspensions to give an average of $10^4$ antibody molecules per bead and the mixture is incubated for several hours. The beads are rinsed by spinning down and resuspending them in TNT buffer to the original volume. Biotinylated DNA fragments N-Flag-OPD.LMB3-2biotin, or fragments that carry the T7 RNA polymerise promoter, the phase T7 gene 10 transitional start site and a gene encoding a different enzyme (also tagged with N-Flag peptide), e.g., methyltransferase HaeIII-N-Flag-M.HaeIII.LMB3-2biotin) are added to the suspension of antibody-coated beads at 1.6 nM concentration and the mixture is incubated overnight at 4° C. The beads are rinsed 3 times by spinning down and resuspending them in TNT buffer.

50 μl aliquots of the above suspension of beads (~$10^9$ beads) are spun in a microfuge at 10,000 g for 3 min. The supernatant is removed and the beads gently resuspended, on ice, in 50 μl of a prokaryotic in vitro coupled transcription/translation system designed for linear templates (Lesley et al., 1991). A commercial preparation of this system is used (*E. coli* S30 Extract System for Linear Templates; Promega) supplemented with T7 RNA polymerise (2,000 units). The reactions are incubated at 25° C. for 1.5 hours and spun in a microfuge at 10,000 g for 3 min. The supernatant is removed and the beads resuspended in 100 μl of 50 mM Tris, 10 mM of potassium carbonate, pH 8.0. An aqueous solution of Cobalt Chloride is added to a concentration of 1 mM and the reactions incubated for 2 hours at room temperature. The beads are rinsed 4 times by spinning down and resuspending them in TNT buffer. Finally, beads are resuspended in TNT buffer to the original volume.

Aliquots of the above beads are added to solutions of 0.25 mM Paraoxon in 50 mM Tris pH 8.3. The beads are incubated at 25° C. with occasional stirring for different periods of time. The beads are spun in a microfuge at 10,000 g for 3 min, the supernatant is removed and its optical density measured at 405 nm. A significant change in optical density at 405 nm is observed when beads to which biotinylated DNA fragments N-Flag-OPD.LMB3-2biotin are attached (and are subsequently reacted as described above) in contrast to reactions conducted under the same conditions but in the absence of beads or phosphotriesterase, or with beads to which N-Flag-M.HaeIII.LMB3-2biotin DNA fragments are attached and are subsequently reacted as described above.

Next, 10 μl (~$2 \times 10^8$ beads) of the above beads are spun in a microfuge at 10,000 g for 3 min. and the supernatant removed. The beads are resuspended in 10 μl of 12.5 or 25 μM EtNP-Bz-Glu-cagedBiotin in 50 mM Tris pH 8.3. The bead suspensions are incubated for 1.5 hour at 25° C. in the dark. The reaction is stopped by the addition of 10 μl 0.1 M sodium acetate, pH 5.0 and transferred to ice and irradiated for 2 min with a B 100 AP UV lamp (UVP) held at a distance of ~6 cm. All bead samples are then incubated for 30 minutes at ambient temperature and then washed three times with 200 μl PBS, 0.1% Tween 20 in a 0.45 μm MultiScreen-HV filter plate (Millipore, MAHVN4510), thoroughly resuspending between each wash. Beads (~$7 \times 10^7$) are then resuspended in 125 μl of a rabbit anti-EtBG serum diluted 1:125 in COVAp and incubated for overnight at 4° C. The beads are washed once with 200 μl COVAp and then 3 times with 200 μl PBS, 0.1% Tween 20 as above and are resuspended in 200 μl PBS, 0.1% Tween 20. 70 μl of the above bead suspensions (~$2 \times 10^7$) are added to 50 μl of 40 ng/μl FITC-labelled goat anti rabbit Fab (Jackson 115-095-006) in PBS, 0.1% Tween 20 and incubated 1 hour at room temperature. The beads are washed 3 times with 200 μl PBS, 0.1% Tween 20 as above, then resuspended in 1 ml PBS, 0.1% Tween 20 and 10,000 events analysed using a FACScan flow cytometer (Becton Dickinson).

Consequently, as seen in FIG. 16, beads to which genes encoding the phosphotriesterase tagged with the Flag peptide were attached (along with an antibody that binds the Flag peptide) could be clearly distinguished from genes to which other genes, encoding enzymes with no phosphotriesterase activity (e.g., N-Flag-M.HaeIII), were attached.

Example 11

*E. coli* BirA Transcribed and Translated In Vitro Catalyses a Reaction which Gives Rise to a Change in the Fluorescence Properties of Substrate-Labelled Microspheres in the Aqueous Compartments of a Water-in Oil Emulsion The gene encoding a peptide from *Propionibacterium shermanii* which is biotinylated in vivo in *E. coli* is amplified using oligonucleotides BCCP5 and BCCP3 from the vector Pinpoint Xa-1 (Promega). The PCR fragment is cloned into the vector pET-23d(FLAG) digested with BamHI and HindIII, downstream of a T7 RNA polymerase promoter and the phage T7 gene 10 translational start site, and in frame with an N-terminal FLAG peptide-coding region; this vector is termed pET-23d(FLAG-BCCP). The vector pET-23d(FLAG) is identical to the vector pET-23d (Novagen) except for the region between the unique NcoI and BamHI sites, which has been modified to include an N-terminal FLAG peptide-coding region as shown below in Scheme 2. (SEQ ID 1 and 2) In order to append a hexahistidine tag to the C-terminus of the protein, the two oligonucleotides BCCPHis+ and BCCPHis- were annealed and then ligated into the vector pET-23d (FLAG-BCCP) digested with SacI and NotI, yielding the vector pET-(FLAG-BCCP-His). The protein FLAG-BCCP-His (termed FBH) is overexpressed in strain C41(DE3) (Miroux & Walker, 1996), harvested and purified with Ni-NTA agarose (Qiagen) under native conditions, following the manufacturer's protocol. Biotinylated protein is depleted by incubation with an equal volume of avidin-agarose (Sigma), pre-equilibrated with a wash buffer (50 mM $NaH_2PO_4$, pH 8.0; 300 mM NaCl; 20 mM imidazole) for 1 hour at 4° C. The suspension is then centrifuged at 10,000 g for 2 minutes and the supernatant retained, aliquoted and stored in liquid nitrogen (long-term) or at 4° C.

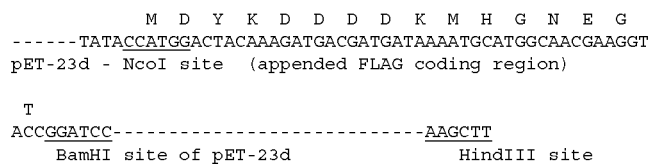

SCHEME 2

The gene encoding E. coli BirA was amplified by PCR using oligonucleotides BirA5 and BirA3 from a pBluescript 2SK+ vector containing the E. coli BirA gene (gift from P. Wang, unpublished). The PCR fragment is cloned into the vector pGEM-4Z(K2) digested with KpnI and XhoI downstream of the lac promoter, T7 RNA polymerase promoter and the efficient phage T7 gene 10 translational start site. The vector pGEM-4Z(K2) is identical to the vector pGEM-4Z$^{NcoI}$ (see Example 8, Scheme 1), except for the region between the unique NcoI and KpnI sites, which has been modified according to Scheme 3 (SEQ ID 3 and 4) shown below to contain a unique XhoI site downstream of the NcoI site.

SCHEME 3

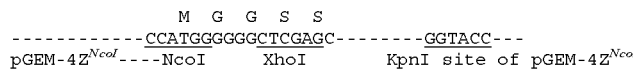

```
            M  G  G  S  S
------------CCATGGGGGGCTCGAGC--------GGTACC---
pGEM-4Z^NcoI----NcoI    XhoI        KpnI site of pGEM-4Z^NcoI
```

DNA sequencing identifies a clone with the correct nucleotide sequence, termed pGEM-BirA. The pGEM-BirA plasmid described above is amplified by PCR using primers LMB2 and LMB3 as above to create a 1139 base pair PCR fragment (BirA_LMB2-3) which carries the T7 RNA polymerase promoter, the phage T7 gene 10 translational start site and the BirA gene. The PCR fragment is purified directly using Wizard PCR Preps (Promega).

60 μL aliquots ($1.2 \times 10^9$ beads) of 1.0 μm diameter non-fluorescent goat anti-mouse IgG labelled microspheres (Bangs Laboratories, CP03N) were spun in a microfuge at approximately 2,600 g (6,000 rpm) for 3 minutes. The supernatant was removed and the beads resuspended in 60 μL 0.1 M Tris-HCl, pH 7.5, 0.15 M NaCl, 0.05% Tween-20, 0.5%-BSA. The beads were spun again, resuspended in 60 μL M5 anti-FLAG antibody (Sigma F4042) and incubated overnight at 4° C. The beads were spun again (2,600 g) for 3 minutes, the supernatant was removed, and the beads were resuspended in a mixture of 30 μL 0.1 M Tris-HCl, pH 7.5, 0.15 M NaCl, 0.05% Tween-20, 0.5% BSA and 30 μL of FBH protein obtained as above (final protein concentration approx. 4 mg/ml) and incubated for 1 hour at room temperature.

Meanwhile, 60 μL aliquots of a prokaryotic in vitro coupled transcription/translation system designed for linear templates (Lesley et al., 1991) was prepared, using a commercial kit (E. coli S30 Extract System for Linear Templates; Promega), supplemented with T7 RNA polymerase (2,000 units), 10 nM BirA_LMB2-3 DNA (or no DNA at all). These aliquots were incubated at 25° C. for 1 hour to allow translation.

The 60 μL aliquots of beads were spun at 2,600 g (6,000 rpm) in a microfuge for 3 minutes and the supernatant removed. They were resuspended in 60 μL of 0.1 M Tris-HCl, pH 7.5, 0.15 M NaCl, 0.05% Tween-20, 0.5% BSA, respun and the supernatant removed. Finally they were resuspended on ice in a 54 μL aliquot of the prokaryotic in vitro coupled transcription/translation reactions described above, supplemented with 3 μL of 2 mM d-biotin and 3 μL of 0.2 M ATP.

A 5 μl aliquot was removed from each reaction mixture and left non-emulsified. 50 μl of the remaining reaction mixture was emulsified essentially as Tawfik & Griffiths (1998).

The oil phase was freshly prepared by dissolving 4.5% (v/v) Span 80 (Fluka) in mineral oil (Sigma, #M-5904) followed by 0.5% (v/v) Tween 80 (SigmaUltra; #P-8074). Ice-cooled reaction mixtures were added gradually (in 5 aliquots of 10 μl over ~2 minutes) to 1.0 ml of ice-cooled oil-phase in a 5 ml Biofreeze Vial (Costar, #2051) whilst stirring with a magnetic bar (8×3 mm with a pivot ring; Scientific Industries International, Loughborough, UK). Stirring (at 1150 rpm) was continued for an additional 1 minute on ice.

All reactions were incubated for 4 hours at 37° C. to allow the biotinylation reaction to proceed.

The emulsions were transferred to 1.5 ml microfuge tubes, spun 1 min. 13.5 k rpm in a microfuge and the oil phase removed leaving the concentrated (but still intact) emulsion at the bottom of the tube. 200 μl 0.1 M Tris-HCl, pH 7.5, 0.15 M NaCl, 0.05% Tween-20, 0.5% BSA were added and the emulsion broken by extracting 4 times with 1 ml hexane, vortexing between each hexane addition. Residual hexane was removed by spinning for 10 ruin at ambient temperature under vacuum in a Speedvac (Farmingdale, N.Y.).

Approximately $1 \times 10^8$ beads from the broken emulsions and the non-emulsified reactions were then washed twice with 100 μl TNT/BSA in a 0.45 μm MultiScreen-HV filter plate (Millipore, MAHVN4510), thoroughly resuspending between each wash. Beads were then resuspend in 50 μl 0.1 M Tris-HCl, pH 7.5, 0.15 M NaCl, 0.05% Tween-20, 0.5% BSA containing 1 μL of a streptavidin-HRP solution (provided with the NEN TSA™-Direct kit) and incubated for 30 minutes at ambient temperature. The beads were washed twice with 100 μl 0.2 M Tris, 10 mM imidazole, pH 8.8, as above, then resuspended in 50 μL 0.2 M Tris, 10 mM imidazole, pH 8.8, 0.01% $H_2O_2$. 1 μL of a fluorescein tyramide stock solution (made up according to the manufacturer's instructions (NEN TSA™-Direct kit)) was added, and the reaction left to proceed for ten minutes. The beads were washed twice with PBS, as above, and finally resuspended in a total of 500 μL PBS, transferred to a 5 ml polystyrene round-bottomed tube (Falcon) and 10,000 events analysed using a FACScan flow cytometer (Becton Dickinson).

As can be seen from FIG. 17, both in emulsified and non-emulsified reactions, the reaction catalysed by in vitro translated BirA results in beads with higher fluorescence than when no enzyme was present. It appears that beads which have been incubated in an emulsion with in vitro translated BirA are more fluorescent than beads which have not been incubated in emulsions.

Example 12

A Change in Fluorescence of Genetic Elements can be Used to Selectively Enrich Genetic Elements Encoding Peptides with a Binding Activity The Fluorescently Labelled Genetic Elements are Isolated by Flow Cytometric Sorting One format for the selection of genetic elements is where the genetic element comprises a gene linked to a microbead, which is translated in a microcapsule, and the translated gene-product is coupled back onto the microbead within the microcapsule. Thus, compartmentalisation leads to the formation of complexes of gene-products attached to the gene encoding them. These complexes can subsequently be selected for binding to a ligand by flow cytometric sorting if the binding interaction results in a change in microbead fluorescence.

pET-23d(FLAG) vector encodes N-terminal FLAG-peptide fused to the polylinker region of pET23d (Novagen). pET23d was digested with Nco I/BamH I, gel purified and redissolved in water. Two synthetic phosphorylated oligonucleotides (Vh Bio Ltd, Newcastle upon Tyne, U.K.), FLAG and FLAGas, were mixed at 1 µM concentration each in water, heated for 3 min at 94° C. and allowed to cool to room temperature before being added to, the digested vector in the ligation mix. The ligation reaction was used unpurified to transform E. coli TG-1. Clones containing the insert were identified by Kpn I digest and verified by sequencing (Oswel Research Product Ltd, Southampton, U.K.). The polylinker region of pET-23d(FLAG) is as follows: (SEQ ID 5 and 6)

```
NcoI                                          KpnI
        10        20        30        40        50
CCATGGACTACAAAGATGACGATGATAAAATGCATGGCAACGAAGGTACC

GGTACCTGATGTTTCTACTGCTACTATTTTACGTACCGTTGCTTCCATGG
    M  D  Y  K  D  D  D  D  K
    <      FLAG-peptide tag       >

BamHI EcoRI SacI    SalI   HindIII Not I XhoI
         60        70        80        90
GGATCCGAATTCGAGCTCCGTCGACAAGCTTGCGCCCGCACTCGAGCA

CCTAGGCTTAAGCTCGAGGCAGCTGTTCGAACGCCGGCGTGAGCTCGT
```

Biotinylated FLAG-HA expression construct was prepared from the pET-23d(FLAG) vector by PCR. The peptide sequence YPYDVPDYA (SEQ. ID No. from the influenza hemagglutinin was appended to the FLAG-tag in pET-23d (FLAG) using the primer FLAGHA and the 5'-biotinylated primer pETrev.b. The amplification product is 903 bases long and the coding region of the construct is: SEQ ID 7 and 8

The competitor construct in the selection process is E. coli folA gene encoding dihydrofolate reductase amplified from pET23a/folA using primers pETfor and pETrev.b.

PCR fragments were gel-purified using QIAquick Gel Extraction kit (Qiagen). DNA concentration was measured by UV spectrophotometry. Dilutions of PCR-prepared expression constructs were made in 0.5 mg/ml carrier DNA prepared from Hind III digested lambda phage DNA (40 min at 80° C., followed by ethanol-precipitation and dissolution in water).

$2 \times 10^9$ streptavidin-coated 0.95 µm polystyrene beads in a 100 µl aliquot of 1% suspension (Bangs Laboratories, Inc. CP01N) were spun in a microfuge at approximately 2,600 g (6,000 rpm) for 3 minutes. The supernatant was removed and the beads resuspended in 100 µL 0.1 M Tris-HCl, pH 7.5, 0.15 M NaCl, 0.05% Tween-20, 0.5% BSA (TNTB). 7 µl of 2 mg/ml biotinylated anti-FLAG monoclonal antibody M5 (Sigma) was added to the resuspended beads and the mix was incubated at room temperature for two hours. Following coating with the antibody, the beads were washed for three times with 200 µl TNTB, resuspended in 100 µl TNTB and split into 10 µl aliquots 1 and 2 and 40 µl aliquots 3 and 4. 0.7 nM stock solution of either, (#1) pure FLAG-HA DNA, (#2) pure folA DNA, or (#3 and #4) pure FLAG-HA DNA diluted in a 1000 fold excess of folA DNA were prepared in Hind III-digested lambda DNA and applied to the bead aliquots. The binding reaction was allowed to proceed overnight at 4° C. The maximum number of genes per bead was 2 in aliquots 1-3 and 0.2 in aliquot 4. The beads coated with FLAG-HA construct served as positive control and the beads coated with folA as negative control.

```
        10        20        30        40        50
ATGGACTACAAAGATGACGATGATAAAATGCATGGCAACGAAGGTACCGG

TACCTGATGTTTCTACTGCTACTATTTTACGTACCGTTGCTTCCATGGCC
       M  D  Y  K  D  D  D  D  K  M  H  G  N  E  G  T  G

<      FLAG-peptide tag       >

60        70        80        90       100
ATCCGGAGGAGGATATCCGTATGATGTGCCGGATTATGCGGGAGGAGGATCCTAA

TAGGCCTCCTCCTATAGGCATACTACACGGCCTAATACGCCCTCCTCCTAGGATT
         S  G  G  G  Y  P  Y  D  V  P  D  Y  A  G  G  G  S
*
                <      HA-peptide tag       >
```

| # | DNA | Ratio folA: FLAG-HA | Beads | DNA (nM) | DNA (μl) | Molecules of DNA/bead | S30 (μl) | Emulsion (ml) |
|---|---|---|---|---|---|---|---|---|
| 1 | FLAG-HA | — | $2 \times 10^8$ | 0.7 | 1 | 2 | 25 | 0.5 |
| 2 | folA | — | $2 \times 10^8$ | 0.7 | 1 | 2 | 25 | 0.5 |
| 3 | folA:HA | 1000:1 | $8 \times 10^8$ | 0.7 | 4 | 2 | 50 | $2 \times 0.5$ |
| 4 | folA:HA | 1000:1 | $8 \times 10^8$ | 0.7 | 0.4 | 0.2 | 50 | $2 \times 0.5$ |

After overnight incubation at 4° C., the beads were washed twice in TNTB and resuspended in S30 in vitro translation mixture (S30 Extract System for Linear Templates, Promega) supplemented with T7 RNA polymerase (20 units/μl).

The ice-cooled in vitro translation reactions were added gradually (in 5 aliquots of 10 μl over ~2 minutes) to 0.5 ml of ice-cooled oil-phase (freshly prepared by dissolving 4.5% (v/v) Span 80 (Fluka) in mineral oil (Sigma, #M-5904) followed by 0.5% (v/v) Tween 80 (SigmaUltra; #P-8074) in a 5 ml Costar BiofreezeVial (#2051)) whilst stirring with a magnetic bar (8×3 mm with a pivot ring; Scientific Industries International, Loughborough, UK). Stirring (at 1150 rpm) was continued for an additional 3 minutes on ice. Reactions were then incubated 90 min at 30° C.

The emulsions were transferred to 1.5 ml microfuge tubes, spun 8 min. 6.5 k rpm in a microfuge and the oil phase removed leaving the concentrated (but still intact) emulsion at the bottom of the tube. 200 μl 0.1 M Tris-HCl, pH 7.5, 0.15 M NaCl, 0.05% Tween-20 (TNT) were added and the emulsion broken by extracting 4 times with 1 ml hexane, vortexing between each hexane addition. Residual hexane was removed by bubbling air through the suspension of beads for 1-2 min at ambient temperature.

Beads from the broken emulsions were then washed twice with 100 μl TNT in a 0.45 μm MultiScreen-HV filter plate (Millipore, MAHVN4510), thoroughly resuspending between each wash. Beads were then resuspend in TNTB at $10^6$ beads/μl and containing 100 mU/ml rat anti-HA-Peroxidase, High Affinity (3F10) conjugate (Boehringer Mannheim).

The beads were incubated with the antibody for 30 minutes at ambient temperature and washed three times with 200 μl TNT before being resuspended in 2 ml of 0.2 M Tris, 10 mM imidazole, pH 8.8. The suspended beads were sonicated for 1 min on ice using Heat Systems sonicator at power 1, 95% cycle, 3.4 mm tip. The sonicated beads were resuspended at $10^8$ beads/ml in 0.2 M Tris, 10 mM imidazole, pH 8.8. To this suspension of beads an equal volume of tyramine signal amplification (TSA) buffer 0.2 M Tris, 10 mM imidazole, pH 8.8, 0.004% $H_2O_2$, 5 μg/ml fluorescein tyramine was added.

Fluorescein tyramine was synthesised as described by Hopman et al. (Anthon H. N. Hopman, Frans C. S. Ramaekers, Ernst J. M. Speel, The Journal of Histochemistry and Cytochemistry vol 46 (6), 771-777, 1998).

The reaction is left to proceed for five minutes at room temperature and stopped by addition of $\frac{1}{10}^{th}$ of volume of 10% bovine serum albumin in PBS (BSA, Sigma). The beads were spun down in 2 ml aliquots of the labelling reaction and washed 2 times in TNTB and once in PBS. Finally the beads were resuspended in 2 ml of PBS and sonicated as above.

The beads coated with genes encoding folA, FLAG-HA or 1001-fold dilution of FLAG-HA in folA were analysed on a Becton Dickinson FACScan flow cytometer.

In FIG. 18, low resolution histogram A demonstrates that the beads carrying FLAG-HA DNA (sample #1) are significantly more fluorescently labelled than the negative control folA (sample #2). The spiked mixtures #3 and #4 run predominantly identically to negative control sample except for a small number of highly fluorescent beads (panel B). 0.04% of beads in sample #3 and 0.02% of beads in sample #4 fell into the region M1 that covers 95% of positive events.

The beads in samples #3 and #4 that fell into region M1 were sorted using a MoFlo fluorescence-activated cell sorter. Two sets of sorted beads were acquired for both samples #3 and #4. In set one 500 beads were collected into a single tube. In set two 96 beads were collected individually into the wells of a 96-well plate. Both sets of beads were subjected to 35-cycle PCR using primers pETrev.b and FLAGrev1.

The amplification products were analysed by gel electrophoresis (FIG. 19). The product sizes are 903 bases for FLAG-HA and 1390 bp for folA.

The gel electrophoretic analysis of the amplification reaction products suggests significant enrichment during the course of sorting. In panel A there are no FLAG-HA bands visible on the lanes of the products amplified from unsorted reactions #3 and #4 whereas the FLAG-HA band in the samples from the sorted beads is strongly visible. Definitive data regarding the nature of the amplified DNA were obtained from the analysis of DNA amplified from single beads. In total 22 beads out of 96 yielded a DNA product for reaction #3 and 50% of these were pure FLAG-HA. For reaction #4 9 beads yielded products and 8 were FLAG-HA.

Single-bead data for reaction #3 suggests that at the concentration applied, nominally 2 DNA molecules/bead, most of the beads in fact have only one gene attached allowing unambiguous linkage between the gene and its product. Relatively high number of positively labelled beads meant however that about 50% of the beads recovered were false positives. In sample #4 where there were only 0.1 genes/bead the purity of the recovered DNA approached 90%, indicating nearly 1000-fold enrichment in one step.

```
Oligonucleotides
EDHFR-Fo      5'-CGA GCT AGA GGT ACC TTA TTA CCG CCG CTC CAG AAT CTC AAA
              GCA ATA G-3'

EDHFR-Ba      5'-GCA TCT GAC AAG CTT AAT AAT TTT GTT TAA CTT TAA GAA GGA
              GAT ATA CAT ATG ATC AGT CTG ATT GCG GCG TTA GCG GTA G-3'

LMB2-Biotin   5'-Biotin-GTA AAA CGA CGG CCA GT-3' folA-FW       5'-GCG CGA AGC TTC GAT CAG TCT GAT TGC GGC G-3'
```

-continued

| | |
|---|---|
| folA-BW | 5'-GCG CCT CGA GTT CCG CCG CTC CAG AAT CTC-3' |
| pETfor.b | 5'-Biotin-GAC TCC AAC GTC AAA GGG CG-3' |
| pETrev.b | 5'-Biotin-GGT TTT CAC CGT CAT CAC CG-3' |
| GFP-FW | 5'-GCG CGA AGC T TCG AGT AAA GGA GAA GAA CTT TTC-3' |
| GFP-BW | 5'-GCG CCT CGA GTT TTG TAT AGT TCA TCC ATG CCA TG-3' |
| GSTM2-2Fo | 5'-TGA TGC CGG TAC CTT ATT ACT TGT TGC CCC AGA CAG CC-3' |
| GSTM2-2Ba | 5'-AGT TAA GTC TAA GCT TAA TAA TTT TGT TTA ACT TTA AGA AGG AGA TAT ACA TAT GCC CAT GAC ACT GGG GTA C-3' |
| LMB2 | 5'-GTA AAA CGA CGG CCA GT-3' |
| LMB3 | 5'-CAG GAA ACA GCT ATG AC-3' |
| N-Flag-OPD-Fo | 5'-TCG ATA CGT CGG TAC CTT ATT ATG ACG CCC GCA AGG TCG GTG-3' |
| N-Flag-OPD-Bc | 5'-CAT TGC CAA GCC ATG GAC TAC AAA GAT GAC GAT GAT AAA ATC ACC AAC AGC GGC GAT CGG ATC AAT ACC G-3' |
| BCCP5 | 5'-CTA GGT CAT GGA TCC ATG AAA CTG AAG GTA ACA GTC AAC GGC-3' |
| BCCP3 | 5'-CAG ATA GCT AAG CTT TTA TTA TTC GAT GAG CTC GAG ATC CCC-3' |
| BCCPHis+ | 5'-CAT CGA AGG TGG CAG CTC TGC-3' |
| BCCPHis- | 5'-GGC CGC AGA GCT GCC ACC TTC GAT GAG CT-3' |
| BirA5 | 5'-ATC GTA GCA CTC GAG CAT GAA GGA TAA CAC CGT GCC A-3' |
| BirA3 | 5'-GTC ATG ACT GGT ACC TTA TTA TTT TTC TGC ACT ACG CAG-3' |
| FLAG | 5'-CAT GGA CTA CAA AGA TGA CGA TGA TAA AAT GCA TGG CAA CGA AGG TAC CG-3' |
| FLAGas | 5'-GAT CCG GTA CCT TCG TTG CAT GCA TTT TAT CAT CGT CAT CTT TGT AGT C-3' |
| FLAGHA | 5'-AAC TCA GCT TCC TTT CGG GCT TTG TTA GGA TCC TCC TCC CGC ATA ATC CGG CAC ATC ATA CGG ATA TCC TCC TCC GGA TCC GGT ACC TTC GTT GCC-3' |
| pETrev.b | 5'-biotin-GGT TTT CAC CGT CAT CAC CG-3' |
| pETfor | 5'-GAC TCC AAC GTC AAA GGG CG-3' |
| FLAGrev1 | 5'-AAC TCA GCT TCC TTT CGG GC-3' |

REFERENCES

Anderson, C. W., Straus, J. W. and Dudock, B. S. (1983) Methods Enzymol, 101, 635-44.

Anderson, J. E. (1993) Curr. Op. Struct. Biol., 3, 24-30. Ash, M. and Ash, I. (1993) Handbook of industrial surfactants. Gower, Aldershot.

Atwell, S. & Wells, J. A. (1999). *Proc. Natl. Acad. Sci. USA* 96, 9497-9502.

Baccanari, D. P., Averett, D., Briggs, C. and Burchall, J. (1977) Biochemistry, 16, 3566-72. Barany, F. (1991) PCR Methods Applic., 1, 5-16.

Baez. S., Segura-Aguilar, J., Widersten, M., Johansson, A.-S. & Mannervik, B. (1997) *Biochem. J.* 324, 25-28.

Bass, S., Greene, R. and Wells, J. A. (1990) Proteins, 8, 309-14.

Becher, P. (1957) Emulsions: theory and practice. Reinhold, New York. Benita, S., Ed. (1996). Microencapsulation: methods and industrial applications. Drugs and pharmaceutical sciences. Edited by Swarbrick, J. New York: Marcel Dekker.

Benner, S. A. (1994) Trends Biotechnol, 12, 158-63.

Berman, J., Eisenberg, S. and Tye, B. K. (1987) Methods Enzymol, 155, 528-37.

Betlach, L., Hershfield, V., Chow, L., Brown, W., Goodman, H. M. & Boyer, H. W. (1976). A restriction endonuclease analysis of the bacterial plasmid controlling the EcoRI restriction and modification of DNA. *Federation Proceedings* 35, 2037-2043.

Blattner, F. R. and Dahlberg, J. E. (1972) Nature New Biol, 237, 227-32.

Bougueleret, L., Schwarzstein, M., Tsugita, A. & Zabeau, M. (1984). Characterization of the genes coding for the Eco RV restriction and modification system of *Escherichia coli*. *Nucleic Acids Res* 12 (8), 3659-76.

Bru, R. & Walde, P. (1991). Product inhibition of alpha-chymotrypsin in reverse micelles. *Eur J Biochem* 199 (1), 95-103. Bru, R. & Walde, P. (1993). Catalytic activity of elastase in reverse micelles. *Biochem Mol Biol Int* 31 (4), 685-92.

Brynes, P. J., Andrade, P. & Gordon D. (1982). Sensitive fluorogenic substrates for the detection of trypsin-like proteases and pancreatic elastase. *Anal. Biochem.* 126, 447.

Cahill, P., Foster, K. and Mahan, D. E. (1991) Clin Chem, 37, 1482-5.

Chakrabarti, A. C., Breaker, R. R., Joyce, G. F. & Deamer, D. W. (1994). Production of RNA by a polymerase protein encapsulated within phospholipid vesicles. *J Mol Evol* 39 (6), 555-9.

Chamberlin, M. and Ring, J. (1973) J Biol Chem, 248, 2235-2244.

Chang, T. M. (1987). Recycling of NAD(P) by multienzyme systems immobilized by microencapsulation in artificial cells. *Methods Enzymol* 136 (67), 67-82.

Chang, T. M. S. (1992). Recent advances in artificial cells based on microencapsulation. In *Microcapsules and nanoparticles in medicine and pharmacy* (Donbrow, M., ed.), pp. 323-339. CRC Press, Boca Raton, Fla.

Chapman, K. B. and Szostak, J. W. (1994) Curr. op. Struct. Biol., 4, 618-622.

Chetverin, A. B. and Spirin, A. S. (1995) Prog Nucleic Acid Res Mol Biol, 51, 225-70.

Clackson, T. and Wells, J. A. (1994) Trends Biotechnol, 12, 173-84.

Cormack, B. P., Valdivia, R. H. & Falkow, S. (1996). FACS-optimized mutants of the green fluorescent protein (GFP). *Gene* (33).

Craig, D. et al. (1995). Fluorescence-based enzymatic assay by capillary electrophoresis laser-induced fluorescence detection for the determination of a few β-galactosidase molecules. *Anal. Biochem.* 226, 147.

Creagh, A. L., Prausnitz, J. M. & Blanch, H. W. (1993). Structural and catalytic properties of enzymes in reverse micelles. *Enzyme Microb Technol* 15 (5), 383-92.

Cull, M. G., Miller, J. F. and Schatz, P. J. (1992) Proc Natl Acad Sci USA, 89, 1865-9.

Delagrave, S., Hawtin, R. E., Silva, C. M., Yang, M. M. & Youvan, D. C. (1995). Red-shifted excitation mutants of the green fluorescent protein. *Biotechnology N Y* 13 (2), 151-4.

Demartis, S., Huber, A., Viti, F., Lozzi, L., Giovannoni, L., Neri, P., Winter, G. & Neri, D. (1999). *J. Mol. Biol.* 286, 617-633.

Dickinson, E. (1994) In Wedlock, D. J. (ed.), Emulsions and droplet size control. Butterworth-Heine-mann, Oxford, Vol. pp. 191-257.

Ehrig, T., O'Kane, D. J. & Prendergast, F. G. (1995). Green-fluorescent protein mutants with altered fluorescence excitation spectra. *Febs Lett* 367 (2), 163-6.

Ellington, A. D. and Szostak, J. W. (1990) Nature, 346, 81822.

Ellman, J., Mendel, D., Anthony, C. S., Noren, C. J. and Schultz, P. G. (1991) Methods Enzymol, 202, 301-36.

Fahy, E., Kwoh, D. Y. and Gingeras, T. R. (1991) PCR Methods Appl, 1, 25-33.

Fields, S. & Song, O. (1989) A novel genetic system to detect protein-protein interactions. *Nature* 340, 245-6.

Finch, C. A. (1993). Encapsulation and controlled release. *Spec. Publ.-R. Soc. Chem.* 138, 35., Fisch, I., Kontermann, R. E., Finnern, R., Hartley, O., Soler, G. A., Griffiths, A. D. and Winter, G. (1996) Proc Natl Acad Sci USA, 93, 7761-6.

Fornusek, L. and Vetvicka, V. (1986). Polymeric microspheres as diagnostic tools for cell surface marker tracing. *Crit. Rev. Ther. Drug Carrier Syst.* 2, 137-74

Freese, E. (1959) J. Mol. Biol., 1, 87.

Friedberg, E. C., Walker, G. C. and Siede, W. (1995) DNA repair and mutagenesis. ASM Press, Washington D. C.

Gold, L., Polisky, B., Uhlenbeck, 0. and Yarus, M. (1995) Annu Rev Biochem, 64, 763-97.

Green, R. and Szostak, J. W. (1992) Science, 258, 1910-5.

Gregoriadis, G. (1976) Methods Enzymol, 44, 21 8-27.

Griffiths, A. D., Williams, S. C., Hartley, O., Tomlinson, I. M., Waterhouse, P., Crosby, W. L., Kontermann, R. E., Jones, P. T., Low, N. M., Allison, T. J. and et al. (1994) Embo J, 13, 3245-60.

Guixe, V., Rodriguez, P. H. & Babul, J. (1998). Ligand-induced conformational transitions in *Escherichia coli* phosphofructokinase 2. *Biochemistry* 37, 13269-75.

Haber, J., Maslakiewicz, P., Rodakiewicz, N. J. & Walde, P. (1993). Activity and spectroscopic properties of bovine liver catalase in sodium bis(2-ethylhexyl)sulfosuccinate/isooctane reverse micelles. *Eur J Biochem* 217 (2), 567-73.

Habig, W. H. & Jakoby, W. B. (1981). *Methods in Enzymology*, 77, 398-405.

Hanes, J. & Pluckthun, A. (1997). In vitro selection and evolution of functional proteins by using ribosome display. *Proc. Natl. Acad. Sci. USA* 94, 4937-4942.

Haugland, R. H. (ed.). (1996). Handbook of Fluorescent Probes and Research Chemicals, Sixth Edition, Molecular Probes, pp 201-250.

Heim, R. & Tsien, R. Y. (1996). Engineering green fluorescent protein for improved brightness, longer wavelengths and fluorescence resonance energy transfer. *Curr Biol* 6 (2), 178-82.

Hermanson, G. T. (1996) Bioconjugate techniques. Academic Press, San Diego.

Hochuli, E., Dobeli, H. and Schacher, A. (1987) J Chromatogr, 411, 177-84.

Hong, S.-B. & Raushel, F. M. (1999). *Biochemistry*, 38, 1159-1165.

Hoogenboom, H. R. (1997). Designing and optimizing library selection strategies for generating high-affinity antibodies. *Trends Biotechnol.* 15, 62-70.

Hoogenboom, H. R., et al., (1991) Nucl. Acids Res., 91, 4133-4137.

Huang, Z. et al. (1992). A sensitive competitive ELISA for 2,4-dinitrophenol using 3,6-fluorescein diphosphate as a fluorogenic substrate. *J. Immunol. Meth.* 149, 261.

Janda, K. D., Lo, L.-C., Lo, C.-H. L., Sim, M., -M., Wang, R., Wong, C.-H. and Lerner, R. A. (1997) Science, 275, 945-948.

Jestin, J.-L., Kristensen, P. & Winter, G. (1999). *Angew. Chem. Int. Ed. Engl.* 38, 1124-1127.

Johannsson, A. (1991) In Price, C. P. and Newman, D. J. (ed.), Heterogeneous enzyme immunoassays. Stockton Press, New York, Vol. pp. 295-325.

Johannsson, A. and Bates, D. L. (1988) In Kemeny, D. M. and Challacombe, S. i. (ed.) Amplification by second enzymes. John Wiley, Chichester, Vol. pp. 85-106.

Jones, L. J. et al. (1997). Quenched BODIPY dye-labeled casein substrates for the assay of protease activity by direct fluorescence measurement. *Anal. Biochem.* 251, 144.

Joyce, G. F. (1994) *Curr. op. Structural Biol.*, 4, 331-336.

Kadir, F. H. and Moore, G. R. (1990) Febs Lett, 276, 81-4.

Kallen, R. G. & Jencks, W. P. (1966). The mechanism of the condensation of formaldehyde with tetrahydrofolic acid. *J. Biol. Chem.* 241, 5851-5863.

Katanaev, V. L., Kurnasov, O. V. and Spirin, A. S. (1995) Febs Lett, 359, 89-92.

Keij, J. F., Groenewegen, A. C. & Visser, J. W. M. (1994) High-speed photodamage cell sorting: An evaluation of the ZAPPER prototype. *Methods in cell biology* 42, 371-358.

Kerker, M. (1983) Elastic and inelastic light scattering in flow cytometry. *Cytometry* 4, 1-10

Klug, A. (1995) Ann N Y Acad Sci, 758, 143-60.

Klug, A. and Schwabe, J. W. (1995) Faseb T, 9, 597-604.

Kolb, V. A., Makeyev, E. V., Kommer, A. and Spirin, A. S. (1995) Biochem Cell Biol, 73, 1217-20.

Kowalczykowski, S. C., Dixon, D. A., Eggleston, A. K., Lauder, S. D. and Rehrauer, W. M. (1994) Microbiol Rev, 58, 401-65.

Krumdiek, C. L. & Baugh, C. M. (1980) Solid-phase synthesis of pteroylpolyglutamates. Methods Enzymol. pp. 524-529

Kumar, A., Kumar, A. & Katiyar, S. S. (1989). Activity and kinetic characteristics of glutathione reductase in vitro in reverse micellar waterpool. *Biochim Biophys Acta* 996 (1-2), 1-6.

Landegren, U., Kaiser, R., Sanders, J. and Hood, L. (1988) Science, 241, 1077-80.

Lesley, S. A., Brow, M. A. & Burgess, R. R. (1991). Use of in vitro protein synthesis from polymerase chain reaction-generated templates to study interaction of *Escherichia coli* transcription factors with core RNA polymerase and for epitope mapping of monoclonal antibodies. *J Biol Chem* 266 (4), 2632-8.

Lesley, S. A. (1995) Methods Mol Biol, 37, 265-78.

Leung, D. W., Chen, E. and Goeddel, D. V. (1989) Technique, 1, 11-15.

Liao, H., McKenzie, T. and Hageman, R. (1986) Proc Natl Acad Sci USA, 83, 576-80.

Lim, F. & Sun, A. M. (1980). Microencapsulated islets as bioartificial endocrine pancreas. *Science* 210 (4472), 908-10.

Lim, F., Ed. (1984). Biomedical applications of microencapsulation. Boca Raton, Fla.: CRC Press.

Lissant, K. J., ed *Emulsions and emulsion technology*. Surfactant Science New York: Marcel Dekker, 1974.

Lissant, K. J., ed. *Emulsions and emulsion technology*. Surfactant Science New York: Marcel Dekker, 1984.

Lorenz, W. W., McCann, R. O., Longiaru, M. & Cormier, M. J. (1991). Isolation and expression of a cDNA encoding *Renilla reniformis* luciferase. *Proc Natl Acad Sci USA* 88 (10), 4438-42.

Low, N. M., Holliger, P. H. and Winter, G. (1996) J Mol Biol, 260, 359-68.

Lowman, H. B., Bass, S. H., Simpson, N. and Wells, J. A. (1991) Biochemistry, 30, 10832-8.

Luisi, P. L. & B., S.-H. (1987). Activity and conformation of enzymes in reverse micellar solutions. *Methods Enzymol* 136 (188), 188-216.

Ma, C., Kudlicki, W., Odom, O. W., Kramer, G. and Hardesty, B. (1993) Biochemistry, 32, 7939-45.

Mackenzie, N. M. & Pinder, A. C. (1986). The application of flow microfluorimetry to biomedical research and diagnosis: a review. *Dev. Biol. Stand.* 64, 181-193.

Magdassi, S., Frenkel, M., Carti, N. and Cazan, R. (1984) 97, 377-379.

Mahajan, N. P., Linder, K., Berry, G., Gordon, G. W., Heim, R. & Herman, B. (1998). Bcl-2 and Bax interactions in mitochondria probed with green fluorescent protein and fluorescence resonance energy transfer. *Nat Biotechnol* 16 (6), 547-52.

Manley, J. L., Fire, A., Samuels, M. and Sharp, P. A. (1983) Methods Enzymol, 101, 568-82.

Mao, Q. & Walde, P. (1991). Substrate effects on the enzymatic activity of alpha-chymotrypsin in reverse micelles. *Biochem Biophys Res Commun* 178 (3), 1105-12.

Mao, Q., Walde, P. & Luisi, P. L. (1992). Kinetic behaviour of alpha chymotrypsin in reverse micelles. A stopped-flow study. *Eur J Biochem* 208 (1), 165-70.

Masui, R. & Kuramitsu, S. (1998). Probing of DNA-binding sites of *Escherichia coli* RecA protein utilizing 1-anilinonaphthalene-8-sulfonic acid. *Biochemistry* 37, 12133-12143.

Matayoshi, E. D. et al. (1990). Novel fluorogenic substrates for assaying retroviral proteases by resonance energy transfer. *Science* 247, 954.

Mattheakis, L. C., Bhatt, R. R. and Dower, W. J. (1994) Proc Natl Acad Sci USA, 91, 9022-6.

McCafferty, J., Griffiths, A. D., Winter, G. and Chiswell, D. J. (1990) Nature, 348, 552-4.

Melton, D. A., Krieg, P. A., Rebagliati, M. R., Maniatis, T., Zinn, K. and Green, M. R. (1984) Nucleic Acids Res, 12, 703556.

Mendel, D., Cornish, V. W. and Schultz, P. G. (1995) Annu Rev Biophys Biomol Struct, 24, 435-62.

Menger, F. M. & Yamada, K. (1979). *J. Am. Chem. Soc.* 101, 6731-6734.

Miele, E. A., Mills, D. R. and Kramer, F. R. (1983) J Mol Biol, 171, 281-95.

Miroux, B., Walker, J. E. (1996) *Journal of Molecular Biology*, 260, 289-298

Miyawaki, A., Llopis, J., Heim, R., McCaffery, J. M., Adams, J. A., Ikura, M. & Tsien, R. Y. (1997). Fluorescent indicators for Ca2+ based on green fluorescent proteins and calmodulin. *Nature* 388 (6645), 882-7.

Mize, P. D., Hoke, R. A., Linn, C. P., Reardon, J. E. and Schulte, T. H. (1989) Anal Biochem, 179, 229-35.

Mock, D. M., Langford, G., DuBois, D., Criscimagna, N. & Horowitz, P. (1985) *Anal. Biochem.* 151, 178-181.

Montigiani, S., Neri, G., Neri, P. and Neri, D. (1996) J Mol Biol, 258, 6-13.

Moore, M. J. (1995) Nature, 374, 766-7.

Mulbry, W. W. & Karns, J. S. (1989) *Journal of Bacteriology*, 171, 6740-6746.

Nemoto, N., Miyamoto-Sato, E., Husimi, Y. and Yanagawa, H. (1997). In vitro virus: Bonding of mRNA bearing puromycin at the 3'-terminal end to the C-terminal end of its encoded protein on the ribosome in vitro. *FEBS Letters* 414, 405-408.

New, R. R. C., Ed. (1990). Liposomes: a practical approach. The practical approach series. Edited by Rickwood, D. & Hames, B. D. Oxford: Oxford University Press.

Nissim, A., Hoogenboom, H. R. I Tomlinson, I. M., Flynn, G., Midgley, C., Lane, D. and Winter, G. (1994) Embo J, 13, 692-8.

Norman, S. O. (1980). Flow cytometry. *Med. Phys.* 7, 609-615.

Oberholzer, T., Albrizio, M. & Luisi, P. L. (1995a). Polymerase chain reaction in liposomes. *Chemistry and Biology* 2, 677-682.

Oberholzer, T., Wick, R., Luisi, P. L. & Biebricher, C. K. (1995b). Enzymatic RNA replication in self-reproducing vesicles: an approach to a minimal cell. *Biochem Biophys Res Commun.* 207 (1), 250-7.

Omburo, G. A., Kuo, J. M., Mullins, L. S. and Raushel, F. M. (1992) *Journal of Biological Chemistry*, 267, 13278-13283.

Parmley, S. F. and Smith, G. P. (1988) Gene, 73, 305-18.

Pederson, H., Holder, S., Sutherlin, D. P., Schwitter, U., King, D. S. & Schultz, P. G. (1998). *Proc. Natl. Acad. Sci. USA* 95, 10523-10528.

Pelham, H. R. and Jackson, R. J. (1976) Eur J Biochem, 67, 247-56.

Perelson, A. S. and Oster, G. F. (1979) J Theor Biol, 81, 64570.

Perez, G. M., Sanchez, F. A. & Garcia, C. F. (1992). Application of active-phase plot to the kinetic analysis of lipoxygenase in reverse micelles. *Biochem J.*

Pirrung & Huang (1996) *Bioconjugate Chemistry*, 7, 317-321.

Posner, B. A., Li, L., Bethell, R., Tsuji, T. and Benkovic, S. J. (1996) Biochemistry, 35, 1653-63.

Qi-X; Grabowski-G A. (1998). Acid beta-glucosidase: intrinsic fluorescence and conformational changes induced by phospholipids and saposin C. *Biochemistry* 37, 11544-115554.

Roberts, B. E., Gorecki, M., Mulligan, R. C., Danna, K. J., Rozenblatt, S. and Rich, A. (1975) Proc Natl Acad Sci USA, 72, 1922-6.

Roberts, J. W. (1969) Nature, 224, 1168-74.

Roberts, R. W. & Szostak, J. W. (1997). RNA-peptide fusions for the in vitro selection of peptides and proteins. *Proc. Natl. Acad. Sci. USA* 94, 12297-12302.

Rolland, J. M., Dimitropoulos, K., Bishop, A., Hocking, G. R. and Nairn R. C. 1985 Fluorescence polarization assay by flow cytometry. *J. Immunol. Methods* 76, 1-10.

Rosenberg, M., Weissman, S. and decrombrugghe, B. (1975) J Biol Chem, 250, 4755-64.

Saiki, R. K., Gelfand, D. H., Stoffel, S., Scharf, S. J., Higuchi, R., Horn, G. T., Mullis, K. B. and Erlich, H. A. (1988) Science, 239, 487-91.

Sambrook, J., Fritsch, E. F. and Maniatis, T. (1989) Molecular cloning: a laboratory manual. Cold Spring Harbor Laboratory Press, New York.

Savage, M. D., Mattson, G., Desai, S., Nielander, G. W., Morgensen, S. and Conklin, E. J. (1994) Avidin-biotin chemistry: a handbook. Pierce Chemical Company, Rockford.

Schick, M. J. (1966) Nonionic surfactants. Marcel Dekker, New York.

Shapiro, H. M. (1983). Multistation multiparameter flow cytometry: a critical review and rationale. *Cytometry* 3, 227-243.

Sherman, P. (1968) Emulsion science. Academic Press, London.

Siemering, K. R., Golbik, R., sever, R. and Haselhof, J. (1996). Mutations that suppress the thermosensitivity of green fluorescent protein. *Current Biology* 6, 1653-1663.

Smith, G. P. (1985) Science, 228, 1315-7.

Soumillion, P., Jaspers, L., Bouchet, M., Marchand, B. J., Winter, G. and Fastrez, J. (1994) J Mol Biol, 237, 415-22.

Stemmer, W. P. (1994a) Nature, 370, 389-91.

Stemmer, W. P. (1994b) Proc Natl Acad Sci USA, 91, 10747-51.

Stofko, H. R., Carr, D. W. and Scott, J. D. (1992) Febs Lett, 302, 274-8.

Sun, A. M., Vasek, I. & Tai, I. (1992). Microencapsulation of living cells and tissues. In *Microencapsulation and nanoparticles in medicine and pharmacy* (Donbrow, M., ed.), pp. 315-322. CRC Press, Boca Raton, Fla.

Sundberg et al. (1995) *J. Am. Chem. Soc.*, 117, 12050-12057.

Tawfik, D. S., Green, B. S., Chap, R., Sela, M. & Eshhar, Z. (1993). catELISA: a facile general route to catalytic antibodies. *Proc Natl Acad Sci USA* 90 (2), 373-7.

Tawfik, D. S., Lindner, A. B., Chap, R., Kim, S.-H., Green, B. S. & Eshhar, Z. (1997). In *Immunology Methods Manual*. pp. 553-559, Ed., I. Lefkovits. Academic Press, London.

Tawfik, D. S. & Griffiths, A. D. (1998). Man-made cell-like compartments for molecular evolution. *Nature Biotechnology* 16, 652-656.

Tokatlidis, K., Friguet, B., Deville, B. D., Baleux, F., Fedorov, A. N., Navon, A., Djavadi, O. L. and Goldberg, M. E. (1995) Philos Trans R Soc Lond B Biol Sci, 348, 89-95.

Tripet, B., Yu, L., Bautista, D. L., Wong, W. Y., Irvin, R. T. and Hodges, R. S. (1996) Protein Engng., 9, 1029-1042.

Tuerk, C. and Gold, L. (1990) Science, 249, 505-10.

van Hal, D. A., Bouwstra, J. A. & Junginger, H. E. (1996). Nonionic surfactant vesicles containing estradiol for topical application. In *Microencapsulation: methods and industrial applications* (Benita, S., ed.), pp. 329-347. Marcel Dekker, New York.

Voss, E. W. 1993. Kinetic measurements of molecular interactions by spectrofluorometry. *J. Mol. Recognit.* 6, 51-58.

Walde, P. Goto, A., Monnard, P.-A., Wessicken, M. & Luisi, P. L. (1994). Oparin's reactions revisited: enzymatic synthesis of poly(adenylic acid) in micelles and self-reproducing vesicles. *J. Am. Chem. Soc.* 116, 7541-7547.

Walde, P., Han, D. & Luisi, P. L. (1993). Spectroscopic and kinetic studies of lipases solubilized in reverse micelles. *Biochemistry* 32 (15), 4029-34.

Walde, P., Peng, Q., Fadnavis, N. W., Battistel, E. & Luisi, P. L. (1988). Structure and activity of trypsin in reverse micelles. *Eur J Biochem* 173 (2), 401-9.

Walker, G. T., Fraiser, M. S., Schram, J. L., Little, M. C., Nadeau, J. G. and Malinowski, D. P. (1992) Nucleic Acids Res, 20, 1691-6.

Wang, G. T. et al. (1990). Design and synthesis of new fluorogenic HIV protease substrates based on resonance energy transfer. *Tetrahedron Lett.* 31, 6493.

Weil, P. A., Luse, D. S., Segall, J. and Roeder, R. G. (1979) Cell, 18, 469-84.

Whateley, T. L. (1996). Microcapsules: preparation by interfacial polymerisation and interfacial complexation and their applications. In *Microencapsulation: methods and industrial applications* (Benita, S., ed.), pp. 349-375. Marcel Dekker, New York.

Wick, R. & Luisi, P. L. (1996). Enzyme-containing liposomes can endogenously produce membrane-constituting lipids. *Chem Biol* 3 (4), 277-85.

Widersten, M. and Mannervik, B. (1995) J Mol Biol, 250, 115-22.

Williams, J. W., Morrison, J. F. and Duggleby, R. G. (1979) Biochemistry, 18, 2567-73.

Winter, G., Griffiths, A. D., Hawkins, R. E. and Hoogenboom, H. R. (1994) Annu Rev Immunol, 12, 433-55.

Wyatt, J. R. 1 Chastain, M. and Puglisi, J. D. (1991) Biotechniques, 11, 764-9.

Yamagishi, J., Kawashima, H., Matsuo, N., Ohue, M., Yamayoshi, M., Fukui, T., Kotani, H., Furuta, R., Nakano, K. and Yamada, M. (1990) Protein Eng, 3, 713-9.

Yelamos, J., Klix, N., Goyenechea, B., Lozano, F., Chui, Y. L., Gonzalez, F. A., Pannell, R., Neuberger, M. S. and Milstein, C. (1995) Nature, 376, 225-9.

Zaccolo, M., Williams, D. M., Brown, D. M. and Gherardi, E. (1996) J Mol Biol, 255, 589-603.

Zakrzewski, S. F. (1980) Preparation of tritiated dihydrofolic acid of high specific activity. Methods Enzymol. pp. 539-.

Zaug, A. J. and Cech, T. R. (1986) Biochemistry, 25, 4478-82.

Zaug, A. J. and Cech, T. R. (1986) Science, 231, 470-5.

Zaug, A. J., Been, M. D. and Cech, T. R. (1986) Nature, 324, 429-33.

Zubay, G. (1973) Annu Rev Genet, 7, 267-87.

Zubay, G. (1980) Methods Enzymol, 65, 856-77.

The invention claimed is:

1. A method for isolating one or more genetic elements encoding a gene product having a desired activity the expression of which results, directly or indirectly, in the modification of an optical property of a genetic element encoding the gene product, comprising the steps of:
   (a) expressing the genetic elements to produce their respective gene products such that the gene products are linked to the genes encoding them;
   (b) compartmentalising genetic elements into microcapsules; and
   (c) sorting the genetic elements which produce the gene product(s) having the desired activity according to a change in the optical properties of the genetic elements.

2. The method according to claim 1, wherein the activity of the desired gene product results, directly or indirectly, in the modification of the genetic element encoding the gene product to enable the isolation of the genetic element.

3. The method according to claim 2, wherein in the modification of the genetic element induces a change in its optical properties.

4. The method according to claim 2, wherein the modification of the genetic element enables it to be further modified outside the microcapsule so as to induce a change in its optical properties.

5. The method according to claim 2, wherein a part of the genetic element is a ligand and the desired gene product binds, directly or indirectly, to said ligand to enable the isolation of the genetic element.

6. The method according to claim 5, wherein the ligand is also encoded by the genetic element.

7. The method according to claim 2, wherein a part of the genetic element is a substrate and the activity of the desired gene product results, directly or indirectly, in the conversion of said substrate into a product which remains part of the genetic element and enables its isolation.

8. The method according to claim 2, wherein the activity of the desired gene product produces a first product that results, directly or indirectly, in the generation of a second product which is subsequently complexed with the genetic element and enables its isolation.

9. The method according to claim 1 wherein the activity of the desired gene product results, directly or indirectly, in the alteration of the expression of a second gene within the microcapsule and the activity of the product of the said second gene enables the isolation of the genetic element using a change in the optical properties of the genetic element.

10. The method according to claim 1, wherein step (a) comprises: expressing the genetic elements to produce their respective gene products, linking the gene products to the genetic elements encoding them and isolating the complexes thereby formed.

11. The method according to claim 10, wherein in step (c) the complexes are directly sorted based on their changed optical properties to isolate genetic elements encoding a gene product having the desired activity.

12. The method according to claim 10, wherein in step (c) the complexes are further reacted to induce a conditional change in optical properties of the genetic element dependent on the presence of gene products with the desired activity in the complex.

13. The method according to claim 10, wherein the complexes are subjected to a further compartmentalisation step in order to isolate the genetic elements encoding a gene product having the desired activity.

14. The method according to claim 1, wherein the change in optical properties of the genetic element is due to binding of a gene product with distinctive optical properties to the genetic element.

15. The method according to claim 1, wherein the change in optical properties of the genetic element is due to binding of a ligand with distinctive optical properties by the gene product.

16. The method according to claim 1, wherein the change in optical properties of the genetic element is due to a change in the optical properties of the gene product when bound to ligand.

17. The method according to claim 1, wherein the change in optical properties of the genetic element is due to a change in the optical properties of a ligand when bound by the gene product.

18. A method according to claim 1, wherein the change in optical properties of the genetic element is due to a change in the optical properties of both a ligand and gene product on binding.

19. The method according to claim 1, wherein the change in optical properties of the genetic element results from a detectable difference in the optical properties of the substrate and product of a reaction catalyzed by a gene product of said genetic element.

20. The method according to claim 1, wherein said gene product is an enzyme and both the substrate and product of the reaction catalyzed by said enzyme have similar optical properties, but only the product, and not the substrate of the reaction being selected binds to, or reacts with, the genetic element, thereby changing the optical properties of the genetic element.

21. The method according to claim 1, wherein further reagents specifically bind to, or specifically react with, the gene product linked to the genetic element, thereby altering the optical properties of the genetic element.

22. The method according to claim 1, wherein a non-desired activity of a gene product results in a change in the optical properties of the genetic element which is distinct from that resulting from the desired activity.

23. The method according to claim 22, wherein the optical change resulting from the non-desired activity is used to negatively select the genetic elements.

24. The method according to claim 22, wherein negative selection against a non-desired activity is combined with positive selection for a desired activity to isolate genetic elements encoding gene products with improved reaction specificity.

25. The method according to claim 24, wherein the improved reaction specificity is an improvement in binding specificity.

26. The method according to claim 24, wherein the improved reaction specificity is an improvement in regio- and/or stereo-selectivity for substrate and/or product.

27. The method according to claim 1, wherein the genetic elements are isolated from a library of genetic elements encoding a repertoire of gene products.

28. The method according to claim 1, wherein each genetic element encodes two or more genes and each gene product must have a desired activity in order for the optical properties of the genetic element to be modified to enable them to be sorted.

29. The method according to claim 1, wherein each genetic element encodes two or more genes and the gene products must bind to each other in order for the optical properties of the genetic element to be modified and the genetic elements sorted.

30. The method according to claim 1 further comprising the additional step of:
(d) introducing one or more mutations into the genetic element(s) isolated in step (c).

31. The method according to claim 30 further comprising iteratively repeating one or more of steps (a) to (d).

32. The method according to claim 1 further comprising amplifying the genetic elements.

33. The method according to claim 1, wherein microencapsulation is achieved by forming a water-in-oil emulsion of an aqueous solution in an oil-based medium.

34. The method according to claim 1, wherein the genetic element comprises a gene attached to a microbead.

35. The method according to claim 34, wherein the microbead is nonmagnetic, magnetic or paramagnetic.

36. The method according to claim 1, wherein the genetic elements are sorted by detection of a change in their fluorescence.

37. The method according to claim 36, wherein the sorting of genetic elements is performed using a fluorescence activated cell sorter (FACS).

38. The method according to claim 36, wherein said change in fluorescence is due to fluorescence resonance energy transfer (FRET).

39. The method according to claim 33, wherein the internal environment of the microcapsules is modified by the addition of one or more reagents to the oil phase.

40. A method for preparing a gene product, comprising the steps of:
(a) preparing a plurality of genetic elements encoding gene products;
(b) expressing the genetic elements to produce their respective gene products;
(c) compartmentalising genetic elements into microcapsules,
(d) sorting the genetic elements which produce the gene product(s) having the desired activity using a change in the optical properties of the gene products or the genetic elements; and
(e) expressing the gene product having the desired activity.

41. A method for screening a compound or compounds capable of modulating the activity of a gene product, comprising the steps of:
(a) preparing a plurality of genetic elements encoding gene products;
(b) expressing the genetic elements to produce their respective gene products;
(c) compartmentalising genetic elements into microcapsules;
(d) sorting the genetic elements which produce the gene product(s) having the desired activity using a change in the optical properties of the gene products or the genetic elements; and
(e) contacting a gene product having the desired activity with the compound or compounds and monitoring the modulation of an activity of the gene product by the compound or compounds.

42. A method for preparing a compound or compounds comprising the steps of:
(a) providing a synthesis protocol wherein at least one step is facilitated by a polypeptide;
(b) preparing genetic elements encoding variants of the polypeptide which facilitates this step;
(c) expressing the genetic elements to produce their respective gene products;
(d) compartmentalising the genetic elements into microcapsules;
(e) sorting the genetic elements which produce polypeptide gene product(s) having the desired activity using a change in the optical properties of the gene products or the genetic elements; and
(f) preparing the compound or compounds using the polypeptide gene product identified in (e) to facilitate the relevant step of the synthesis.

* * * * *

SEQUENCE LISTING

<160> NUMBER OF SEQ ID NOS: 40

<210> SEQ ID NO 1
<211> LENGTH: 61
<212> TYPE: DNA
<213> ORGANISM: Artificial sequence
<220> FEATURE:
<223> OTHER INFORMATION: Sequence about the NcoI site of vector pET-23d
<220> FEATURE:
<221> NAME/KEY: CDS
<222> LOCATION: (7)..(51)
<223> OTHER INFORMATION: Appended FLAG coding Region
<220> FEATURE:
<221> NAME/KEY: misc_feature
<222> LOCATION: (5)..(10)
<223> OTHER INFORMATION: NcoI site
<220> FEATURE:
<221> NAME/KEY: misc_feature
<222> LOCATION: (56)..(61)
<223> OTHER INFORMATION: BamHI site

<400> SEQUENCE: 1 tatacc atg gac tac aaa gat gac gat gat aaa atg cat ggc aac gaa       48
       Met Asp Tyr Lys Asp Asp Asp Asp Lys Met His Gly Asn Glu
       1               5                   10 ggt taccggatcc                                                        61
Gly
15

<210> SEQ ID NO 2
<211> LENGTH: 15
<212> TYPE: PRT
<213> ORGANISM: Artificial sequence
<220> FEATURE:
<223> OTHER INFORMATION: Sequence encoded about the NcoI site of
      vector pET-23d
<220> FEATURE:
<221> NAME/KEY: misc_feature
<222> LOCATION: (5)..(10)
<223> OTHER INFORMATION: NcoI site
<220> FEATURE:
<221> NAME/KEY: misc_feature
<222> LOCATION: (56)..(61)
<223> OTHER INFORMATION: BamHI site

<400> SEQUENCE: 2

Met Asp Tyr Lys Asp Asp Asp Asp Lys Met His Gly Asn Glu Gly
1               5                   10                  15

<210> SEQ ID NO 3
<211> LENGTH: 17
<212> TYPE: DNA
<213> ORGANISM: Artificial sequence
<220> FEATURE:
<223> OTHER INFORMATION: Sequence about the NcoI site of vector
      pGEM-4ZNcoI
<220> FEATURE:
<221> NAME/KEY: CDS
<222> LOCATION: (3)..(17)
<223> OTHER INFORMATION:
<220> FEATURE:
<221> NAME/KEY: misc_feature
<222> LOCATION: (1)..(6)
<223> OTHER INFORMATION: NcoI site
<220> FEATURE:
<221> NAME/KEY: misc_feature
<222> LOCATION: (11)..(16)
<223> OTHER INFORMATION: XhoI site -continued

```
<400> SEQUENCE: 3 cc atg ggg ggc tcg agc                                              17
   Met Gly Gly Ser Ser
   1               5

<210> SEQ ID NO 4
<211> LENGTH: 5
<212> TYPE: PRT
<213> ORGANISM: Artificial sequence
<220> FEATURE:
<223> OTHER INFORMATION: Peptide sequence encoded about the NcoI site
      of vector pGEM-4ZNcoI
<220> FEATURE:
<221> NAME/KEY: misc_feature
<222> LOCATION: (1)..(6)
<223> OTHER INFORMATION: NcoI site
<220> FEATURE:
<221> NAME/KEY: misc_feature
<222> LOCATION: (11)..(16)
<223> OTHER INFORMATION: XhoI site

<400> SEQUENCE: 4

Met Gly Gly Ser Ser
1               5

<210> SEQ ID NO 5
<211> LENGTH: 98
<212> TYPE: DNA
<213> ORGANISM: Artificial sequence
<220> FEATURE:
<223> OTHER INFORMATION: Polylinker region of plasmid pET-23d(FLAG),
      including FLAG encoding region
<220> FEATURE:
<221> NAME/KEY: CDS
<222> LOCATION: (3)..(29)
<223> OTHER INFORMATION: Flag-peptide tag
<220> FEATURE:
<221> NAME/KEY: misc_feature
<222> LOCATION: (1)..(98)
<223> OTHER INFORMATION: Polylinker

<400> SEQUENCE: 5 cc atg gac tac aaa gat gac gat gat aaa atgcatggca acgaaggtac        49
   Met Asp Tyr Lys Asp Asp Asp Asp Lys
   1               5 cggatccgaa ttcgagctcc gtcgacaagc ttgcggccgc actcgagca               98

<210> SEQ ID NO 6
<211> LENGTH: 9
<212> TYPE: PRT
<213> ORGANISM: Artificial sequence
<220> FEATURE:
<223> OTHER INFORMATION: FLAG epitope tag encoded by plasmid
      pET-23d(FLAG)
<220> FEATURE:
<221> NAME/KEY: misc_feature
<222> LOCATION: (1)..(98)
<223> OTHER INFORMATION: Polylinker

<400> SEQUENCE: 6

Met Asp Tyr Lys Asp Asp Asp Asp Lys
1               5

<210> SEQ ID NO 7
<211> LENGTH: 105
<212> TYPE: DNA
<213> ORGANISM: Artificial sequence
```

```
<220> FEATURE:
<223> OTHER INFORMATION: Sequence encoding FLAG, HA epitope tag
      peptide encoded by plasmid pET-23d(FLAGHA)
<220> FEATURE:
<221> NAME/KEY: CDS
<222> LOCATION: (1)..(105)
<223> OTHER INFORMATION: FLAG HA  peptide

<400> SEQUENCE: 7 atg gac tac aaa gat gac gat gat aaa atg cat ggc aac gaa ggt acc        48
Met Asp Tyr Lys Asp Asp Asp Asp Lys Met His Gly Asn Glu Gly Thr
1               5                   10                  15 gga tcc gga gga gga tat ccg tat gat gtg ccg gat tat gcg gga gga        96
Gly Ser Gly Gly Gly Tyr Pro Tyr Asp Val Pro Asp Tyr Ala Gly Gly
            20                  25                  30 gga tcc taa                                                            105
Gly Ser <210> SEQ ID NO 8
<211> LENGTH: 34
<212> TYPE: PRT
<213> ORGANISM: Artificial sequence
<220> FEATURE:
<223> OTHER INFORMATION: FLAG, HA epitope tag peptide encoded by
      plasmid pET-23d(FLAGHA)

<400> SEQUENCE: 8

Met Asp Tyr Lys Asp Asp Asp Asp Lys Met His Gly Asn Glu Gly Thr
1               5                   10                  15

Gly Ser Gly Gly Gly Tyr Pro Tyr Asp Val Pro Asp Tyr Ala Gly Gly
            20                  25                  30

Gly Ser

<210> SEQ ID NO 9
<211> LENGTH: 49
<212> TYPE: DNA
<213> ORGANISM: Artificial Sequence
<220> FEATURE:
<223> OTHER INFORMATION: Oligonucleotide EDHFR-Fo

<400> SEQUENCE: 9
cgagctagag gtaccttatt accgccgctc cagaatctca aagcaatag                  49

<210> SEQ ID NO 10
<211> LENGTH: 82
<212> TYPE: DNA
<213> ORGANISM: Artificial Sequence
<220> FEATURE:
<223> OTHER INFORMATION: Oligonucleotide EDHFR-Ba

<400> SEQUENCE: 10
gcatctgaca agcttaataa ttttgtttaa ctttaagaag gagatataca tatgatcagt      60
ctgattgcgg cgttagcggt ag                                               82

<210> SEQ ID NO 11
<211> LENGTH: 17
<212> TYPE: DNA
<213> ORGANISM: Artificial Sequence
<220> FEATURE:
<223> OTHER INFORMATION: Biotynylated Oligonucleotide LMB2-Biotin

<400> SEQUENCE: 11
gtaaaacgac ggccagt                                                     17
```

<210> SEQ ID NO 12
<211> LENGTH: 30
<212> TYPE: DNA
<213> ORGANISM: Artificial Sequence
<220> FEATURE:
<223> OTHER INFORMATION: Oligonucleotide folA-FW

<400> SEQUENCE: 12
gcgcgaagct tcgatcagtc tgattgcggc                                     30

<210> SEQ ID NO 13
<211> LENGTH: 30
<212> TYPE: DNA
<213> ORGANISM: Artificial Sequence
<220> FEATURE:
<223> OTHER INFORMATION: Oligonucleotide folA-BW

<400> SEQUENCE: 13
gcgcctcgag ttccgccgct ccagaatctc                                     30

<210> SEQ ID NO 14
<211> LENGTH: 25
<212> TYPE: DNA
<213> ORGANISM: Artificial Sequence
<220> FEATURE:
<223> OTHER INFORMATION: Biotinylated Oligonucleotide pETfor.b

<400> SEQUENCE: 14
gactccaacg tcaaagggcg artca                                          25

<210> SEQ ID NO 15
<211> LENGTH: 20
<212> TYPE: DNA
<213> ORGANISM: Artificial Sequence
<220> FEATURE:
<223> OTHER INFORMATION: Biotinylated oligonucleotide pETrev.b

<400> SEQUENCE: 15
ggttttcacc gtcatcaccg                                                20

<210> SEQ ID NO 16
<211> LENGTH: 34
<212> TYPE: DNA
<213> ORGANISM: Artificial Sequence
<220> FEATURE:
<223> OTHER INFORMATION: oligonucleotide GFP-FW

<400> SEQUENCE: 16
gcgcgaagct tcgagtaaag gagaagaact tttc                                34

<210> SEQ ID NO 17
<211> LENGTH: 35
<212> TYPE: DNA
<213> ORGANISM: Artificial Sequence
<220> FEATURE:
<223> OTHER INFORMATION: Oligonucleotide GFP-BW

<400> SEQUENCE: 17
gcgcctcgag ttttgtatag ttcatccatg ccatg                               35

<210> SEQ ID NO 18
<211> LENGTH: 38
<212> TYPE: DNA
<213> ORGANISM: Artificial Sequence
<220> FEATURE:
<223> OTHER INFORMATION: oligonucleotide GSTM2-2Fo -continued

```
<400> SEQUENCE: 18
tgatgccggt accttattac ttgttgcccc agacagcc                              38

<210> SEQ ID NO 19
<211> LENGTH: 73
<212> TYPE: DNA
<213> ORGANISM: Artificial Sequence
<220> FEATURE:
<223> OTHER INFORMATION: Oligonucleotide GSTM2-2Ba

<400> SEQUENCE: 19
agttaagtct aagcttaata attttgttta actttaagaa ggagatatac atatgcccat      60
gacactgggg tac                                                         73

<210> SEQ ID NO 20
<211> LENGTH: 17
<212> TYPE: DNA
<213> ORGANISM: Artificial Sequence
<220> FEATURE:
<223> OTHER INFORMATION: olidonucleotide LMB2

<400> SEQUENCE: 20
gtaaaacgac ggccagt                                                     17

<210> SEQ ID NO 21
<211> LENGTH: 17
<212> TYPE: DNA
<213> ORGANISM: Artificial Sequence
<220> FEATURE:
<223> OTHER INFORMATION: Oligonucleotide LMB3

<400> SEQUENCE: 21
caggaaacag ctatgac                                                     17

<210> SEQ ID NO 22
<211> LENGTH: 42
<212> TYPE: DNA
<213> ORGANISM: Artificial Sequence
<220> FEATURE:
<223> OTHER INFORMATION: Oligonucleotide N-Flag-OPD-Bc

<400> SEQUENCE: 22
tcgatacgtc ggtaccttat tatgacgccc gcaaggtcgg tg                         42

<210> SEQ ID NO 23
<211> LENGTH: 70
<212> TYPE: DNA
<213> ORGANISM: Artificial Sequence
<220> FEATURE:
<223> OTHER INFORMATION: Oligonucleotide N-Flag-OPD-Bc

<400> SEQUENCE: 23
cattgccaag ccatggacta caaagatgac gatgataaaa tcaccaacag cggcgatcgg      60
atcaataccg                                                             70

<210> SEQ ID NO 24
<211> LENGTH: 42
<212> TYPE: DNA
<213> ORGANISM: Artificial Sequence
<220> FEATURE:
<223> OTHER INFORMATION: Oligonucleotide BCCP5

<400> SEQUENCE: 24
ctaggtcatg gatccatgaa actgaaggta acagtcaacg gc                         42
```

<210> SEQ ID NO 25
<211> LENGTH: 42
<212> TYPE: DNA
<213> ORGANISM: Artificial Sequence
<220> FEATURE:
<223> OTHER INFORMATION: Oligonucleotide BCCP3

<400> SEQUENCE: 25
cagatagcta agcttttatt attcgatgag ctcgagatcc cc         42

<210> SEQ ID NO 26
<211> LENGTH: 21
<212> TYPE: DNA
<213> ORGANISM: Artificial Sequence
<220> FEATURE:
<223> OTHER INFORMATION: Oligonucleotide BCCPHis+

<400> SEQUENCE: 26
catcgaaggt ggcagctctg c                                21

<210> SEQ ID NO 27
<211> LENGTH: 29
<212> TYPE: DNA
<213> ORGANISM: Artificial Sequence
<220> FEATURE:
<223> OTHER INFORMATION: OligonucleotideBCCPHis-

<400> SEQUENCE: 27
ggccgcagag ctgccacctt cgatgagct                        29

<210> SEQ ID NO 28
<211> LENGTH: 37
<212> TYPE: DNA
<213> ORGANISM: Artificial Sequence
<220> FEATURE:
<223> OTHER INFORMATION: Oligonucleotide BirA5

<400> SEQUENCE: 28
atcgtagcac tcgagcatga aggataacac cgtgcca                37

<210> SEQ ID NO 29
<211> LENGTH: 39
<212> TYPE: DNA
<213> ORGANISM: Artificial Sequence
<220> FEATURE:
<223> OTHER INFORMATION: Oligonucleotide BirA3

<400> SEQUENCE: 29
gtcatgactg gtaccttatt attttctgc actacgcag               39

<210> SEQ ID NO 30
<211> LENGTH: 50
<212> TYPE: DNA
<213> ORGANISM: Artificial Sequence
<220> FEATURE:
<223> OTHER INFORMATION: Oligonucleotide FLAG

<400> SEQUENCE: 30
catggactac aaagatgacg atgataaaat gcatggcaac gaaggtaccg   50

<210> SEQ ID NO 31
<211> LENGTH: 49
<212> TYPE: DNA
<213> ORGANISM: Artificial Sequence
<220> FEATURE:
<223> OTHER INFORMATION: Oligonucleotide FLAGas

<400> SEQUENCE: 31
gatccggtac cttcgttgca tgcattttat catcgtcatc tttgtagtc          49

<210> SEQ ID NO 32
<211> LENGTH: 96
<212> TYPE: DNA
<213> ORGANISM: Artificial Sequence
<220> FEATURE:
<223> OTHER INFORMATION: Oligonucleotide FLAGHA

<400> SEQUENCE: 32
aactcagctt cctttcgggc tttgttagga tcctcctccc gcataatccg gcacatcata    60
cggatatcct cctccggatc cggtaccttc gttgcc                              96

<210> SEQ ID NO 33
<211> LENGTH: 20
<212> TYPE: DNA
<213> ORGANISM: Artificial Sequence
<220> FEATURE:
<223> OTHER INFORMATION: Oligonucleotide pETrev.b

<400> SEQUENCE: 33
ggttttcacc gtcatcaccg                                                20

<210> SEQ ID NO 34
<211> LENGTH: 20
<212> TYPE: DNA
<213> ORGANISM: Artificial Sequence
<220> FEATURE:
<223> OTHER INFORMATION: Oligonucleotide pETfor

<400> SEQUENCE: 34
gactccaacg tcaaagggcg                                                20

<210> SEQ ID NO 35
<211> LENGTH: 20
<212> TYPE: DNA
<213> ORGANISM: Artificial Sequence
<220> FEATURE:
<223> OTHER INFORMATION: Oligonucleotide FLAGrev1

<400> SEQUENCE: 35
aactcagctt cctttcgggc                                                20

<210> SEQ ID NO 36
<211> LENGTH: 98
<212> TYPE: DNA
<213> ORGANISM: plasmid pET-23d(FLAG)

<400> SEQUENCE: 36
ggtacctgat gtttctactg ctactatttt acgtaccgtt gcttccatgg cctaggctta    60
agctcgaggc agctgttcga acgccggcgt gagctcgt                            98

<210> SEQ ID NO 37
<211> LENGTH: 9
<212> TYPE: PRT
<213> ORGANISM: Influenza virus

<400> SEQUENCE: 37

Tyr Pro Tyr Asp Val Pro Asp Tyr Ala
1               5

```
<210> SEQ ID NO 38
<211> LENGTH: 105
<212> TYPE: DNA
<213> ORGANISM: plasmid pET-23d(FLAGHA)

<400> SEQUENCE: 38
tacctgatgt ttctactgct actattttac gtaccgttgc ttccatggcc taggcctcct     60
cctataggca tactacacgg cctaatacgc cctcctccta ggatt                    105

<210> SEQ ID NO 39
<211> LENGTH: 9
<212> TYPE: PRT
<213> ORGANISM: Artificial Sequence
<220> FEATURE:
<223> OTHER INFORMATION: Flag peptide

<400> SEQUENCE: 39

Met Asp Tyr Lys Asp Asp Asp Asp Lys
1               5

<210> SEQ ID NO 40
<211> LENGTH: 52
<212> TYPE: DNA
<213> ORGANISM: Artificial sequence
<220> FEATURE:
<223> OTHER INFORMATION: pGEM -4Z plasmid

<400> SEQUENCE: 40
aagcttaata attttgttta actttaagaa ggagatatag ccatggggta cc              52
```